United States Patent
Kageyama

(10) Patent No.: US 9,590,182 B2
(45) Date of Patent: Mar. 7, 2017

(54) BENZOFLUORENE COMPOUND, MATERIAL FOR LUMINESCENT LAYER USING SAID COMPOUND AND ORGANIC ELECTROLUMINESCENT DEVICE

(71) Applicant: JNC CORPORATION, Tokyo (JP)

(72) Inventor: Akiko Kageyama, Chiba (JP)

(73) Assignee: JNC CORPORATION, Tokyo (JP)

( * ) Notice: Subject to any disclaimer, the term of this patent is extended or adjusted under 35 U.S.C. 154(b) by 283 days.

(21) Appl. No.: 14/359,795

(22) PCT Filed: Oct. 26, 2012

(86) PCT No.: PCT/JP2012/077693
§ 371 (c)(1),
(2) Date: May 21, 2014

(87) PCT Pub. No.: WO2013/077141
PCT Pub. Date: May 30, 2013

(65) Prior Publication Data
US 2014/0319510 A1    Oct. 30, 2014

(30) Foreign Application Priority Data

Nov. 25, 2011 (JP) .................................. 2011-257145

(51) Int. Cl.
*H01L 51/00* (2006.01)
*C07C 211/61* (2006.01)
(Continued)

(52) U.S. Cl.
CPC ........ *H01L 51/0058* (2013.01); *C07C 211/61* (2013.01); *C07F 7/0818* (2013.01);
(Continued)

(58) Field of Classification Search
None
See application file for complete search history.

(56) References Cited

U.S. PATENT DOCUMENTS 6,455,579 B1    9/2002    Satsuki et al.
2003/0143422 A1    7/2003    Chen
(Continued)

FOREIGN PATENT DOCUMENTS

CN    101421226    4/2009
JP    1-245087    9/1989
(Continued)

OTHER PUBLICATIONS

Machine English translation of JP 2011-219461. May 10, 2016.*
(Continued)

*Primary Examiner* — J. L. Yang
(74) *Attorney, Agent, or Firm* — Wenderoth, Lind & Ponack, L.L.P.

(57) ABSTRACT

The present invention is capable of providing a light emitting device with excellent device lifetime while maintaining low driving voltage and good color purity by using a benzofluorene compound which is substituted with a diaryl amino group having a naphthyl and a phenyl or a heteroaryl and which is represented by general formula (1) as a material
(Continued)

for luminescent layers of an organic electroluminescent device, for example. (In the formula, Ar is a phenyl, a heteroaryl, etc., $R^1$ and $R^2$ are fluorine or a substituted silyl, etc., n1 and n2 are an integer of 0-5, and $R^3$ is an alkyl, etc.)

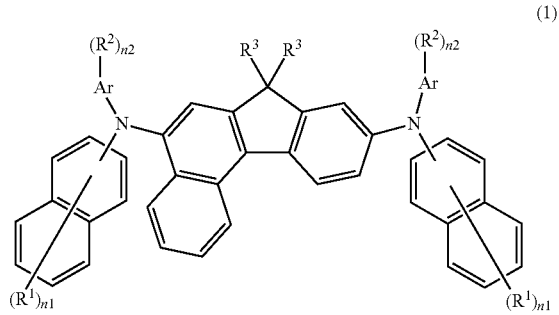

(1)

14 Claims, 1 Drawing Sheet

(51) Int. Cl.
*C09K 11/06* (2006.01)
*H01L 51/50* (2006.01)
*C07F 7/08* (2006.01)
*C09B 57/00* (2006.01)
*C09B 69/00* (2006.01)

(52) U.S. Cl.
CPC .......... *C09B 57/008* (2013.01); *C09B 69/008* (2013.01); *C09K 11/06* (2013.01); *H01L 51/006* (2013.01); *H01L 51/0054* (2013.01); *H01L 51/5012* (2013.01); *C09K 2211/1011* (2013.01); *C09K 2211/1014* (2013.01); *C09K 2211/1029* (2013.01); *H01L 51/0077* (2013.01); *H01L 51/0094* (2013.01); *H01L 2251/308* (2013.01)

(56) References Cited

U.S. PATENT DOCUMENTS

| | | | |
|---|---|---|---|
| 2003/0152800 | A1 | 8/2003 | Tamao et al. |
| 2003/0214227 | A1 | 11/2003 | Tsuchiya |
| 2005/0063175 | A1 | 3/2005 | Mizusaki et al. |
| 2005/0089718 | A1 | 4/2005 | Yamagata et al. |
| 2005/0121667 | A1 | 6/2005 | Kuehl et al. |
| 2005/0139810 | A1 | 6/2005 | Kuehl et al. |
| 2006/0073359 | A1 | 4/2006 | Ise et al. |
| 2006/0073360 | A1 | 4/2006 | Ise et al. |
| 2006/0158102 | A1 | 7/2006 | Kawamura et al. |
| 2006/0210828 | A1 | 9/2006 | Nakayama et al. |
| 2006/0264625 | A1 | 11/2006 | Nakayama et al. |
| 2007/0184304 | A1 | 8/2007 | Yamagata et al. |
| 2008/0160347 | A1 | 7/2008 | Wang et al. |
| 2008/0233429 | A1 | 9/2008 | Oguma et al. |
| 2009/0184312 | A1 | 7/2009 | Nishiyama et al. |
| 2009/0309490 | A1 | 12/2009 | Ise et al. |

FOREIGN PATENT DOCUMENTS

| | | |
|---|---|---|
| JP | 2-247278 | 10/1990 |
| JP | 6-298758 | 10/1994 |
| JP | 10-335066 | 12/1998 |
| JP | 11-97178 | 4/1999 |
| JP | 2000-26324 | 1/2000 |
| JP | 2000-34234 | 2/2000 |
| JP | 2000-133457 | 5/2000 |
| JP | 2001-52869 | 2/2001 |
| JP | 2001-76876 | 3/2001 |
| JP | 2001-81090 | 3/2001 |
| JP | 2001-217077 | 8/2001 |
| JP | 2001-220577 | 8/2001 |
| JP | 2001-267075 | 9/2001 |
| JP | 2001-267076 | 9/2001 |
| JP | 2001-267078 | 9/2001 |
| JP | 2001-267079 | 9/2001 |
| JP | 2001-307884 | 11/2001 |
| JP | 2002-234892 | 8/2002 |
| JP | 2003-257621 | 9/2003 |
| JP | 2003/277741 | 10/2003 |
| JP | 2003-321546 | 11/2003 |
| JP | 2003-347056 | 12/2003 |
| JP | 2004-43646 | 2/2004 |
| JP | 2004-111379 | 4/2004 |
| JP | 2004-119211 | 4/2004 |
| JP | 2004-281086 | 10/2004 |
| JP | 2004-331508 | 11/2004 |
| JP | 2004-335122 | 11/2004 |
| JP | 2005-97263 | 4/2005 |
| JP | 2005-97283 | 4/2005 |
| JP | 2005-51373 | 5/2005 |
| JP | 2005-126399 | 5/2005 |
| JP | 2005-167175 | 6/2005 |
| JP | 2005-298483 | 10/2005 |
| JP | 2006-80419 | 3/2006 |
| JP | 2006-89398 | 4/2006 |
| JP | 2006-93542 | 4/2006 |
| JP | 2006/512395 | 4/2006 |
| JP | 2006-128634 | 5/2006 |
| JP | 2006-156888 | 6/2006 |
| JP | 2006-190718 | 7/2006 |
| JP | 2007-27587 | 2/2007 |
| JP | 2008-214271 | 9/2008 |
| JP | 2008-291006 | 12/2008 |
| JP | 2011-37838 | 2/2011 |
| JP | 2011-219461 | 11/2011 |
| KR | 10-2010-0112903 | 10/2010 |
| KR | 10-2011-0000006 | 1/2011 |
| WO | 00/40586 | 7/2000 |
| WO | 03/051092 | 6/2003 |
| WO | 2004/061048 | 7/2004 |
| WO | 2005/056633 | 6/2005 |
| WO | 2010/016405 | 2/2010 |
| WO | 2010/059837 | 5/2010 |

OTHER PUBLICATIONS

Office Action issued Oct. 19, 2015 in corresponding Chinese Application No. 201280036456.2, with English abstract.
Office Action issued Jan. 11, 2016 in corresponding Taiwanese Application No. 101139772, with English abstract.
International Search Report issued Jan. 15, 2013 in International (PCT) Application No. PCT/JP2012/077693.
Office Action issued Oct. 21, 2014 in corresponding Japanese Application No. 2011-047369, with English Abstract.
Office Action issued Apr. 21, 2015 in corresponding Japanese Application No. 2011-047369, with English Abstract.
Notice of Allowance issued Sep. 15, 2015 in corresponding Japanese Application No. 2011-047369, with English Abstract.
"The Fifth Series of Experimental Chemistry 14, Synthesis of Organic Compounds II—Alcohol and Amine", the $2^{nd}$ issue, Maruzen Co. Ltd., Apr. 15, 2007, pp. 363-364, with English Abstract.
Office Action issued Apr. 13, 2016 in corresponding Chinese Application No. 201280036456.2.
Notice of Allowance dated Dec. 5, 2016 issued in corresponding Taiwanese Patent Application No. 101139772.

* cited by examiner

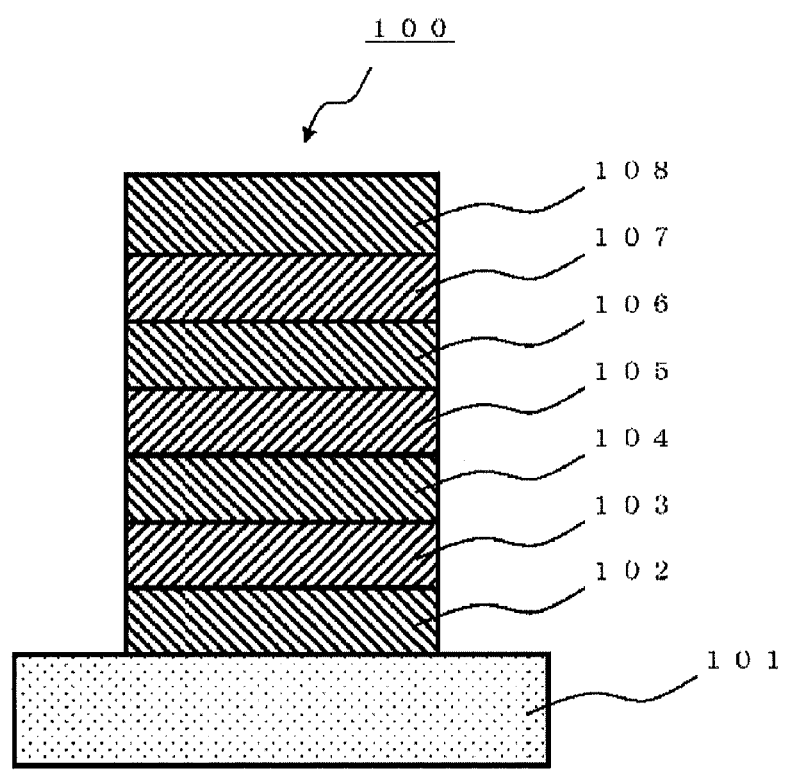

BENZOFLUORENE COMPOUND, MATERIAL FOR LUMINESCENT LAYER USING SAID COMPOUND AND ORGANIC ELECTROLUMINESCENT DEVICE

TECHNICAL FIELD

The present invention relates to a benzofluorene compound, a material for a luminescent layer using the compound and an organic electroluminescent device.

BACKGROUND ART

Organic electroluminescent devices are self-luminescent type luminescent devices, and are expected as luminescent devices for displays or lighting devices. Conventionally, various display devices using luminescent devices that emit light by electroluminescence have been studied since they can save electrical power and can be made thinner, and organic electroluminescent devices formed of organic materials have been actively considered since weight saving and increasing in size are easy. Especially, the development of organic materials having luminescence properties including blue, which is one of the three primary colors of light, and the development of organic materials having charge transportability for holes, electrons and the like (they have possibilities to be semiconductors or superconductors) have been actively studied until now regardless of polymer compounds or low-molecular-weight compounds.

An organic electroluminescent device has a structure formed of a pair of electrodes formed of an anode and a cathode, and one or plural layer(s) containing an organic compound, which is/are disposed between the pair of electrodes. The layers containing an organic compound include luminescent layers, and charge transport/injection layers that transport or inject electrical charges such as holes and electrons, and as the organic compound, various organic materials have been developed (for example, WO 2004/061048 A (JP 2006-512395 A), WO 2005/056633 A: see Patent Literatures 1 and 2). However, the Examples of these patent documents disclose only polymer compounds of benzofluorene.

Furthermore, for example, WO 2003/051092 A (JP 2005-513713 A) shows a dibenzofluorene compound having an aryl-substituted amino (see Patent Literature 3). However, the document discloses only the structural formula thereof, and does not report the specific properties thereof. In addition, JP 2008-214271 A shows a benzofluorene compound having an aryl-substituted amino (see Patent Literature 4), and WO 2010/59837A shows a chrysene compound having an aryl-substituted amino (see Patent Literature 5).

CITATION LIST

Patent Literatures

Patent Literature 1: WO 2004/061048 A (JP 2006-512395 A)
Patent Literature 2: WO 2005/056633 A
Patent Literature 3: WO 2003/051092 A (JP 2005-513713 A)
Patent Literature 4: JP 2008-214271 A
Patent Literature 5: WO 2010/59837 A

SUMMARY OF INVENTION

Technical Problem

However, an organic electroluminescent device having sufficient performances with respect to device lifetime and the like has not been obtained yet even the above-mentioned organic materials were used. Furthermore, materials that can be driven at low voltages, and materials by which blue luminescence with a high color purity can be obtained for improving an NTSC ratio have been required. Under such circumstances, the development of an organic electroluminescent device having fine performances in device lifetime, driving voltage and color purity, and the like, that is, a compound from which such device can be obtained, is desired.

Solution to Problem

The present inventors intensively studied so as to solve the above-mentioned problems, and consequently found a benzofluorene compound represented by the following general formula (1) and succeeded in the production thereof. Furthermore, they found that an organic electroluminescent device having improved properties in device lifetime and the like can be obtained by constituting an organic electroluminescent device by disposing a layer containing this benzofluorene compound between a pair of electrodes, and completed the present invention. Namely, the present invention provides the benzofluorene compounds mentioned below.

[1] A benzofluorene compound represented by the following general formula (1):

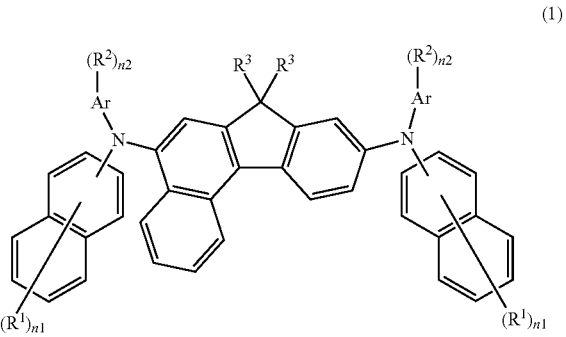

(1)

wherein

Ars are each independently phenyl, naphthyl or a heteroaryl, $R^1$ and $R^2$ are each independently, an aryl, a cycloalkyl, fluorine, cyano, an alkyl optionally substituted by fluorine, an alkoxy optionally substituted by fluorine, a substituted silyl or a substituted germyl, n1 and n2 are each independently an integer of 0 to 5, and in the case when one naphthyl group is substituted with two or more adjacent $R^1$s or in the case when one Ar group is substituted with two or more adjacent $R^2$s, these may bind to form an aliphatic ring, $R^3$s are each independently an alkyl or an aryl, wherein two $R^3$s may bind to each other to form a ring, and at least one hydrogen in the compound represented by the formula (1) may be substituted with deuterium.

[2] The benzofluorene compound according to [1], wherein

Ars are each independently phenyl or pyridyl, $R^1$ and $R^2$ are each independently an aryl with a carbon number of 6 to 12, a cycloalkyl with a carbon number of 3 to 6, fluorine, cyano, an alkyl with a carbon number of 1 to 6 optionally substituted by fluorine, an alkoxy with a carbon number of 1 to 4 optionally substituted by fluorine, an alkyl-substituted silyl or an alkyl-substituted germyl, n1 and n2 are each independently an integer of 0 to 3, and in the case when one naphthyl group is substituted with two or more adjacent $R^1$s or in the case when one Ar group is substituted with two or more adjacent $R^2$s, they may bind to form an aliphatic ring with a carbon number of 3 to 6, $R^3$s are each independently an alkyl with a carbon number of 1 to 6 or an aryl with a carbon number of 6 to 12, wherein two $R^3$s may bind to each other to form a ring, and at least one hydrogen in the Ars and naphthyl groups in the compound represented by the formula (1) may be substituted with deuterium.

[3] The benzofluorene compound according to [1], wherein

Ars are each independently phenyl or pyridyl, $R^1$ and $R^2$ are each independently phenyl, cyclopropyl, cyclobutyl, cyclopentyl, cyclohexyl, methylcyclopentyl, fluorine, cyano, methyl, ethyl, n-propyl, isopropyl, n-butyl, s-butyl, t-butyl, fluorinated methyl, fluorinated ethyl, methoxy, ethoxy, propoxy, isopropoxy, n-butoxy, isobutoxy, s-butoxy, t-butoxy, methoxy fluoride, ethoxy fluoride, trimethylsilyl, triethylsilyl, t-butyldimethylsilyl, trimethylgermyl, triethylgermyl or t-butyldimethylgermyl, n1 and n2 are each independently an integer of 0 to 2, and in the case when one naphthyl group is substituted with two or more adjacent $R^1$s or in the case when one Ar group is substituted with two or more adjacent $R^2$s, these may bind to form an aliphatic ring with a carbon number of 5 to 6, $R^3$s are each independently methyl, ethyl, n-propyl, isopropyl, n-butyl, s-butyl, t-butyl or phenyl, and in the case when n1 and n2 are 0, at least one hydrogen in the Ars and naphthyl groups in the compound represented by the formula (1) may be substituted with deuterium.

[4] The benzofluorene compound according to [1], wherein

Ars are each independently phenyl or pyridyl, $R^1$ and $R^2$ are each independently phenyl, cyclopentyl, cyclohexyl, methylcyclopentyl, fluorine, cyano, methyl, ethyl, n-propyl, isopropyl, t-butyl, methyl fluoride, methoxy, ethoxy, methoxy fluoride, trimethylsilyl, triethylsilyl, trimethylgermyl or triethylgermyl, n1 and n2 are each independently an integer of 0 to 2, and in the case when one naphthyl group is substituted with two or more adjacent $R^1$s or in the case when one Ar group is substituted with two or more adjacent $R^2$s, these may bind to form a cyclohexane ring, and $R^3$s are each independently methyl, ethyl or phenyl.

[5] The benzofluorene compound according to [1], which is represented by the following formula (1-1):

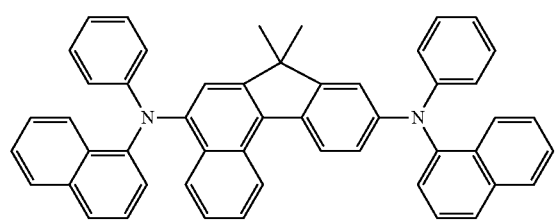

(1-1)

[6] The benzofluorene compound according to [1], which is represented by the following formula (1-51):

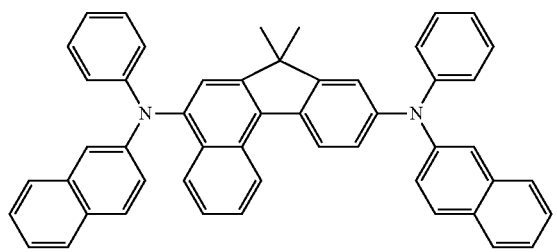

(1-51)

[7] The benzofluorene compound according to claim 1, which is represented by the following formula (1-22):

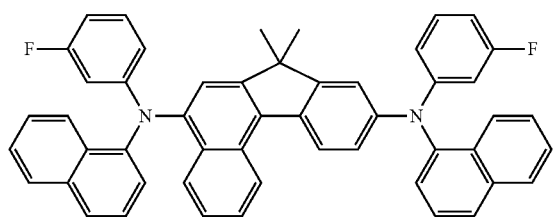

(1-22)

[8] The benzofluorene compound according to [1], which is represented by the following formula (1-20):

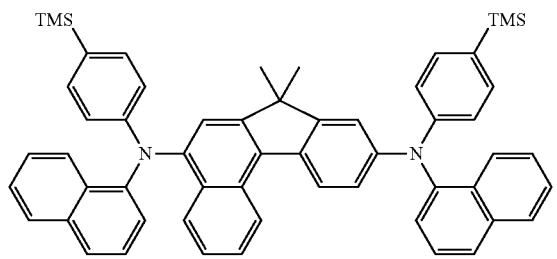

(1-20)

[9] A material for a luminescent layer of a luminescent device, which contains the benzofluorene compound according to any one of [1] to [8].

[10] An organic electroluminescent device having a pair of electrodes including an anode and a cathode, and a luminescent layer containing the material for a luminescent layer according to [9], which is disposed between the pair of electrodes.

[11] The organic electroluminescent device according to [10], which further has an electron transport layer and/or an electron injection layer that is/are disposed between the cathode and the luminescent layer, wherein at least one of the electron transport layer and electron injection layer contains at least one selected from the group consisting of quinolinol-based metal complexes, pyridine derivatives, phenanthroline derivatives, borane derivatives and benzimidazole derivatives.

[12] The organic electroluminescent device according to [11], wherein the electron transport layer and/or electron injection layer further contain(s) at least one selected from the group consisting of alkali metals, alkaline earth metals, rare earth metals, oxides of alkali metals, halides of alkali metals, oxides of alkaline earth metals, halides of alkaline earth metals, oxides of rare earth metals, halides of rare earth metals, organic complexes of alkali metals, organic complexes of alkaline earth metals and organic complexes of rare earth metals.

[13] A display device having the organic electroluminescent device according to any one of [8] to [12].

[14] A lighting device having the organic electroluminescent device according to any one of [8] to [12].

Advantageous Effect of Invention

According to the preferable embodiments of the present invention, for example, a benzofluorene compound having excellent properties as a material for a luminescent layer can be provided. Furthermore, an organic electroluminescent device having improved characteristics in device lifetime and the like while maintaining a low driving voltage and an excellent color purity (while showing more excellent driving voltage and color purity over the luminescent devices described in the conventional patent documents) can be provided.

BRIEF DESCRIPTION OF DRAWINGS

FIG. 1 is a schematic cross-sectional view showing the organic electroluminescent device according to this exemplary embodiment.

DESCRIPTION OF EMBODIMENTS

1. Benzofluorene Compound Represented by General Formula (1)

The benzofluorene compound of the present invention will be explained in detail. The benzofluorene compound according to the present invention is a benzofluorene compound represented by the above-mentioned general formula (1).

The "alkyl" in $R^1$, $R^2$ and $R^3$ of the general formula (1) may be either of a straight chain or a branched chain, and examples may include straight chain alkyls with a carbon number of 1 to 24 or branched chain alkyls with a carbon number of 3 to 24. Preferable "alkyls" are alkyls with a carbon number of 1 to 18 (branched chain alkyls with a carbon number of 3 to 18). More preferable "alkyls" are alkyls with a carbon number of 1 to 12 (branched chain alkyls with a carbon number of 3 to 12). Further preferable "alkyls" are alkyls with a carbon number of 1 to 6 (branched chain alkyls with a carbon number of 3 to 6). Especially preferable "alkyls" are alkyls with a carbon number of 1 to 4 (branched chain alkyls with a carbon number of 3 to 4).

Specific "alkyls" include methyl, ethyl, n-propyl, isopropyl, n-butyl, isobutyl, s-butyl, t-butyl, n-pentyl, isopentyl, neopentyl, t-pentyl, n-hexyl, 1-methylpentyl, 4-methyl-2-pentyl, 3,3-dimethylbutyl, 2-ethylbutyl, n-heptyl, 1-methylhexyl, n-octyl, t-octyl, 1-methylheptyl, 2-ethylhexyl, 2-propylpentyl, n-nonyl, 2,2-dimethylheptyl, 2,6-dimethyl-4-heptyl, 3,5,5-trimethylhexyl, n-decyl, n-undecyl, 1-methyldecyl, n-dodecyl, n-tridecyl, 1-hexylheptyl, n-tetradecyl, n-pentadecyl, n-hexadecyl, n-heptadecyl, n-octadecyl, n-eicosyl and the like.

The "alkyl" in $R^1$ and $R^2$ of the general formula (1) may be substituted with fluorine, and examples include fluorides of the above-mentioned alkyls, and specific examples include methyl fluoride, ethyl fluoride, n-propyl fluoride, isopropyl fluoride, n-butyl fluoride, isobutyl fluoride, s-butyl fluoride, t-butyl fluoride and the like.

Examples of the "aryl" in $R^1$, $R^2$ and $R^3$ of the general formula (1) include aryls with a carbon number of 6 to 30. Preferable "aryls" are aryls with a carbon number of 6 to 16, more preferably aryls with a carbon number of 6 to 12.

Specific "aryls" include phenyl, (o-, m-, p-) tolyls, (2,3-, 2,4-, 2,5-, 2,6-, 3,4-, 3,5-) xylyls, mesityl, (o-, m-, p-) cumenyls, which are monocyclic aryls, (2-, 3-, 4-) biphenylyls, which are bicyclic aryls, (1-, 2-) naphthyls, which are condensed bicyclic aryls, terphenyls, which are tricyclic aryls (m-terphenyl-2'-yl, m-terphenyl-4'-yl, m-terphenyl-5'-yl, o-terphenyl-3'-yl, o-terphenyl-4'-yl, p-terphenyl-2'-yl, m-terphenyl-2-yl, m-terphenyl-3-yl, m-terphenyl-4-yl, o-terphenyl-2-yl, o-terphenyl-3-yl, o-terphenyl-4-yl, p-terphenyl-2-yl, p-terphenyl-3-yl, p-terphenyl-4-yl), acenaphthylene-(1-, 3-, 4-, 5-)yls, fluorene-(1-, 2-, 3-, 4-, 9-)yls, phenalene-(1-, 2-)yls, (1-, 2-, 3-, 4-, 9-)phenanethryls, which are condensed tricyclic aryls, quaterphenylyls, which are tetracyclic aryls (5'-phenyl-m-terphenyl-2-yl, 5'-phenyl-m-terphenyl-3-yl, 5'-phenyl-m-terphenyl-4-yl, m-quaterphenyl), triphenylene-(1-, 2-)yls, pyrene-(1-, 2-, 4-)yls and naphthacene-(1-, 2-, 5-)yls, which are condensed tetracyclic aryls, perylene-(1-, 2-, 3-) yls and pentacene-(1-, 2-, 5-, 6-) yls, which are condensed pentacyclic aryls, and the like.

Examples of the "cycloalkyl" in $R^1$ and $R^2$ of the general formula (1) include cycloalkyls with a carbon number of 3 to 12. Preferable "cycloalkyls" are cycloalkyls with a carbon number of 3 to 10. More preferable "cycloalkyls" are cycloalkyls with a carbon number of 3 to 8. Further preferable "cycloalkyls" are cycloalkyls with a carbon number of 3 to 6.

Specific "cycloalkyls" include cyclopropyl, cyclobutyl, cyclopentyl, cyclohexyl, methylcyclopentyl, cycloheptyl, methylcyclohexyl, cyclooctyl or dimethylcyclohexyl, and the like.

Examples of the "alkoxy" in $R^1$ and $R^2$ of the general formula (1) include alkoxys with a carbon number of 1 to 15. Preferable "alkoxys" are alkoxys with a carbon number of 1 to 10. Further preferable "alkoxys" are alkoxys with a carbon number of 1 to 4.

Specific "alkoxys" include methoxy, ethoxy, propoxy, isopropoxy, n-butoxy, isobutoxy, s-butoxy, t-butoxy, pentyloxy, cyclopentyloxy, hexyloxy, cyclohexyloxy, heptyloxy, cycloheptyloxy, octyloxy, cyclooctyloxy, phenoxy and the like.

The "alkoxy" in $R^1$ and $R^2$ of the general formula (1) may be substituted with fluorine, and examples include fluorides of the above-mentioned alkoxys, and specific examples include methoxy fluoride, ethoxy fluoride, propoxy fluoride, isopropoxy fluoride, n-butoxy fluoride, isobutoxy fluoride, s-butoxy fluoride, t-butoxy fluoride and the like.

The "substituted silyl" in $R^1$ and $R^2$ of the general formula (1) include substituted silyls in which the three hydrogens in a silyl group ($-SiH_3$) are each independently substituted with methyl, ethyl, n-propyl, isopropyl, n-butyl, s-butyl, t-butyl, cyclobutyl, cyclopentyl, cyclohexyl, phenyl, biphenylyl or naphthyl, or the like. Among these, trialkyl-substituted silyls are preferable.

Specific "substituted silyls" include trialkylsilyls such as trimethylsilyl, triethylsilyl, tripropylsilyl, triisopropylsilyl, tributylsilyl, tri-s-butylsilyl, tri-t-butylsilyl, ethyldimethylsilyl, propyldimethylsilyl, isopropyldimethylsilyl, butyldimethylsilyl, s-butyldimethylsilyl, t-butyldimethylsilyl, methyldiethylsilyl, propyldiethylsilyl, isopropyldiethylsilyl, butyldiethylsilyl, s-butyldiethylsilyl, t-butyldiethylsilyl, methyldipropylsilyl, ethyldipropylsilyl, butyldipropylsilyl, s-butyldipropylsilyl, t-butyldipropylsilyl, methyldiisopropylsilyl, ethyldiisopropylsilyl, butyldiisopropylsilyl, s-butyldiisopropylsilyl, t-butyldiisopropylsilyl and the like. Furthermore, phenyldimethylsilyl, phenyldiethylsilyl, phenyldi-t-butylsilyl, methyldiphenylsilyl, ethyldiphenylsilyl, propyldiphenylsilyl, isopropyldiphenylsilyl, butyldiphenylsilyl, s-butyldiphenylsilyl, t-butyldiphenylsilyl, triphenylsilyl and the like are exemplified.

As the "substituted germyl" in $R^1$ and $R^2$ of the general formula (1), substituted germyls in which the three hydrogens in a germyl group (—GeH$_3$) are each independently substituted by methyl, ethyl, n-propyl, isopropyl, n-butyl, s-butyl, t-butyl, cyclobutyl, cyclopentyl, cyclohexyl, phenyl, biphenylylornaphthyl, or the like. Among these, trialkyl-substituted germyls are preferable.

Specific "substituted germyls" include trialkylgermyls such as trimethylgermyl, triethylgermyl, tripropylgermyl, triisopropylgermyl, tributylgermyl, tri-s-butylgermyl, tri-t-butylgermyl, ethyldimethylgermyl, propyldimethylgermyl, isopropyldimethylgermyl, butyldimethylgermyl, s-butyldimethylgermyl, t-butyldimethylgermyl, methyldiethylgermyl, propyldiethylgermyl, isopropyldiethylgermyl, butyldiethylgermyl, s-butyldiethylgermyl, t-butyldiethylgermyl, methyldipropylgermyl, ethyldipropylgermyl, butyldipropylgermyl, s-butyldipropylgermyl, t-butyldipropylgermyl, methyldiisopropylgermyl, ethyldiisopropylgermyl, butyldiisopropylgermyl, s-butyldiisopropylgermyl and t-butyldiisopropylgermyl. Furthermore, phenyldimethylgermyl, phenyldiethylgermyl, phenyldi-t-butylgermyl, methyldiphenylgermyl, ethyldiphenylgermyl, propyldiphenylgermyl, isopropyldiphenylgermyl, butyldiphenylgermyl, s-butyldiphenylgermyl, t-butyldiphenylgermyl, triphenylgermyl and the like are exemplified.

n1 and n2 are each independently an integer of 0 to 5, preferably an integer of 0 to 3, more preferably an integer of 0 to 2, further preferably 0. Furthermore, in the case when one naphthyl group is substituted with two or more adjacent $R^1$s or in the case when one Ar group is substituted with two or more adjacent $R^2$s, these may bind to form an aliphatic ring. As the formed aliphatic ring, aliphatic rings with a carbon number of 3 to 6 are preferable, and aliphatic rings with a carbon number of 5 to 6 are further preferable. Furthermore, specific examples include aliphatic rings such as cyclobutane, cyclopentane and cyclohexane.

The structures of the naphthyl groups substituted with $R^1$(s) may be the same or different on the left and right of the benzofluorene backbone, but are preferably the same. Furthermore, the forms of binding of the naphthyl group to the amino group (1-naphthyl or 2-naphthyl) may be the same or different on the left and right of the benzofluorene backbone, but are preferably the same. Furthermore, the structures of the Ar groups substituted with $R^2$ may be the same or different on the left and right of the benzofluorene backbone, but are preferably the same. In addition, the forms of binding of the Ar group to the amino group (for example, 1-naphthyl or 2-naphthyl when Ar is a naphthyl group, 1-pyridyl, 2-pyridyl or 3-pyridyl when Ar is a pyridyl group) may be the same or different on the left and right of the benzofluorene backbone, but are preferably the same. The case when the structures of the diarylamino groups on the left and right that are binding to the benzofluorene backbone are the same is the most preferable.

The two $R^3$s may be the same or different, but it is preferable that the two $R^3$s are the same. Furthermore, the two $R^3$s may bind to each other to form a ring (preferably an aliphatic ring with a carbon number of 3 to 6), and as a result thereof, for example, aliphatic rings such as cyclobutane, cyclopentane, cyclohexane, methylcyclohexane, dimethylcyclohexane and trimethylcyclohexane, or aromatic heterocycles such as a fluorine ring may be spiro-condensed with the five-membered ring of the benzofluorene backbone.

In addition, with respect to $R^3$, alkyls tend to have a shorter luminescence wavelength than that of aryls, alkyls are more preferable in the cases when blue luminescent is intended. The alkyls may be any of those mentioned above, but methyl is especially preferable. On the other hand, in the cases when a relatively long luminescence wavelength is desired, aryls can also be used.

Examples of the "heteroaryl" in Ar of the general formula (1) include heteroaryls with a carbon number of 2 to 30. Preferable "heteroaryls" are heteroaryls with a carbon number of 2 to 25, more preferably heteroaryls with a carbon number of 2 to 20, further preferably heteroaryls with a carbon number of 2 to 15, and especially preferably heteroaryls with a carbon number of 2 to 10. Furthermore, examples of the "heteroaryl" include heterocyclic groups containing 1 to 5 heteroatom(s) selected from oxygen, sulfur and nitrogen besides carbon as ring constitutional atoms, and the like.

Examples of the "heterocyclic groups" include pyrrolyl, oxazolyl, isoxazolyl, thiazolyl, isothiazolyl, imidazolyl, oxadiazolyl, thiadiazolyl, triazolyl, tetrazolyl, pyrazolyl, pyridyl, pyrimidinyl, pyridazinyl, pyrazinyl, triazinyl, indolyl, isoindolyl, 1H-indazolyl, benzimidazolyl, benzoxazolyl, benzothiazolyl, 1H-benzotriazolyl, quinolyl, isoquinolyl, cinnolyl, quinazolyl, quinoxalinyl, phthalazinyl, naphthylidinyl, purinyl, pteridinyl, carbazolyl, acridinyl, phenoxazinyl, phenothiazinyl, phenazinyl, indolidinyl and the like, and imidazolyl, pyridyl, carbazolyl and the like are preferable.

With respect to Ar in the general formula (1), heteroaryls tend to have a shorter luminescence wavelength than that of phenyl and the like, heteroaryls are more preferable in the cases when blue luminescent is intended. The heteroaryls may be any of those mentioned above, but pyridyl is especially preferable. On the other hand, in the cases when a relatively long luminescence wavelength is desired, phenyl and the like can also be used.

Furthermore, a part or the entirety of the hydrogen atoms in the benzofluorene ring that constitutes the compound represented by the general formula (1), hydrogens in Ar groups (phenyl, naphthyl or heteroaryl) and a naphthyl group, hydrogen atoms in $R^{3-}$, $R^2$ or $R^3$ may be deuterium. In the case when a part is substituted with deuterium, it is preferable that at least one hydrogen of Ar or the naphthyl group is substituted by deuterium, and it is more preferable, in the case when n1 and n2 are 0, at least one hydrogen of Ar or the naphthyl group is substituted by deuterium. On the other hand, compounds that are not substituted by deuterium at all may be allowable.

Specific examples of the above-mentioned compound represented by the general formula (1) include the compounds represented by the following formula (1-1) to formula (1-85). Among the following compounds, the compounds represented by the formula (1-1), the formula (1-3), the formula (1-6), the formula (1-7), the formula (1-19), the formula (1-20), the formula (1-22), the formula (1-25), the formula (1-29), the formula (1-50), the formula (1-51), the formula (1-53), the formula (1-62), the formula (1-64), the formula (1-69) and the formula (1-82) are preferable.

(1-1)
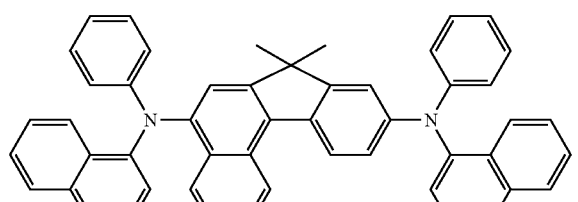
(1-2)
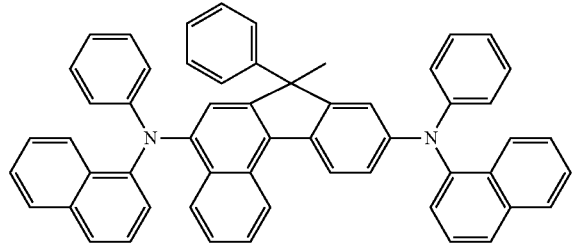
(1-3)
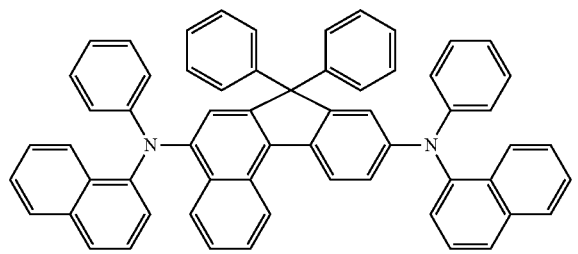
(1-4)
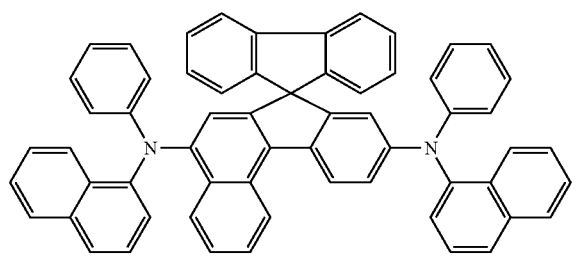
(1-5)
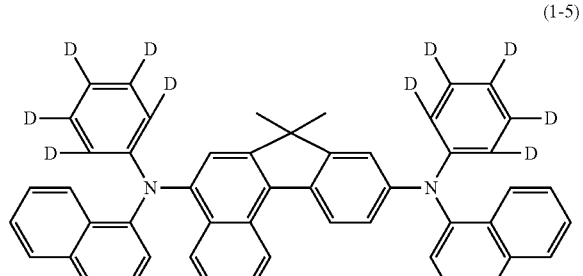
(1-6)
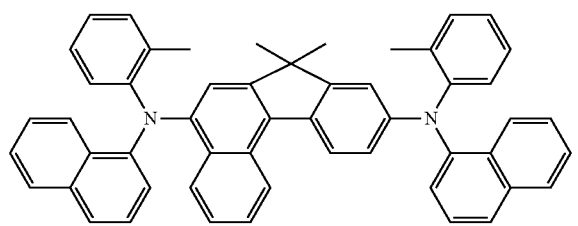
-continued
(1-7)
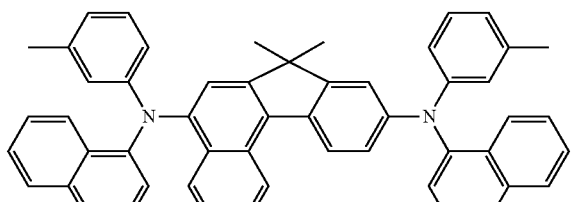
(1-8)
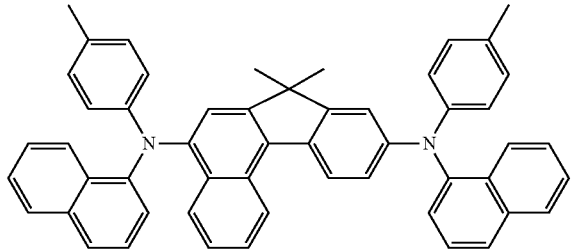
(1-9)
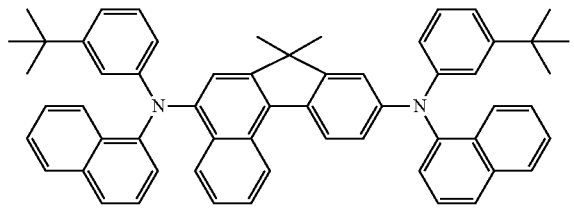
(1-10)
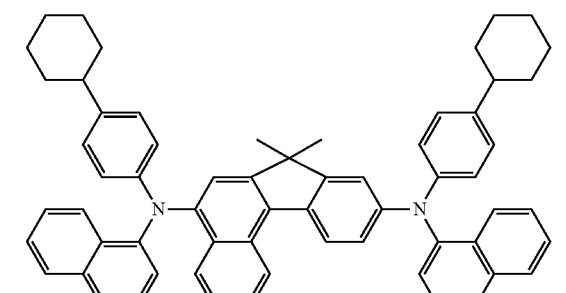
(1-11)
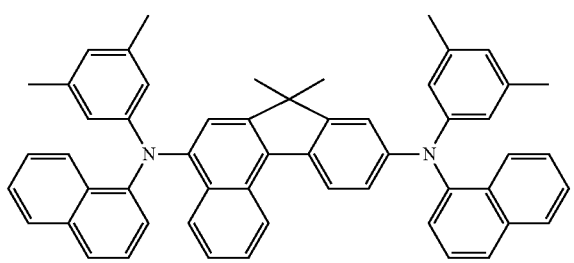
(1-12)
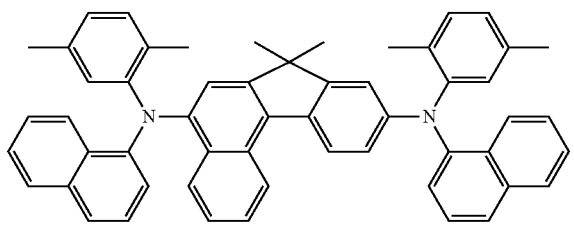

(1-13)
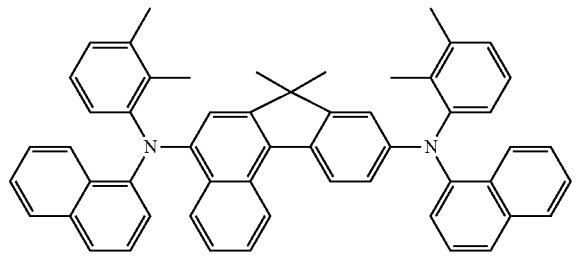
(1-14)
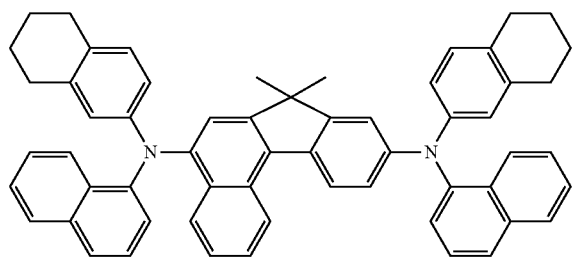
(1-15)
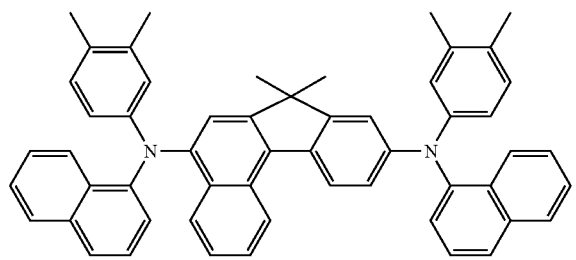
(1-16)
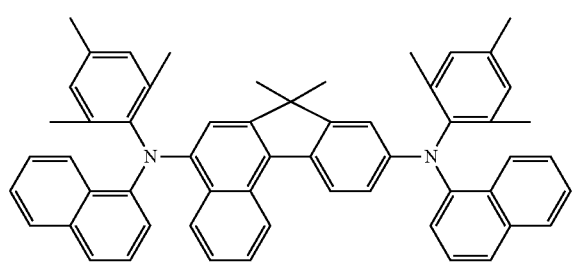
(1-17)
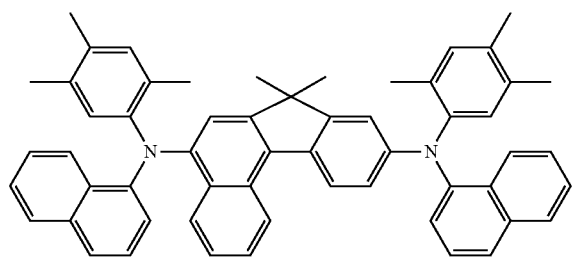
(1-18)
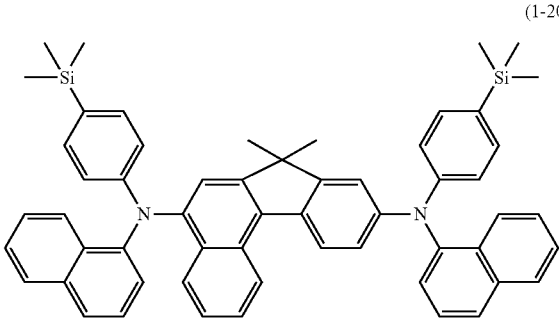
(1-19)
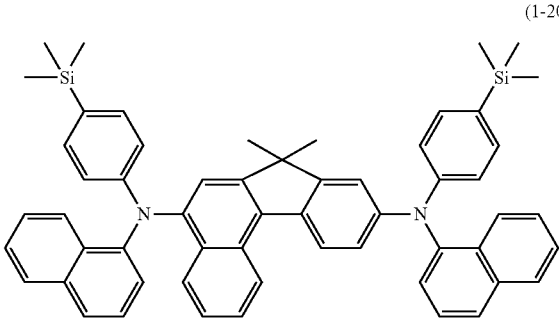
(1-20)
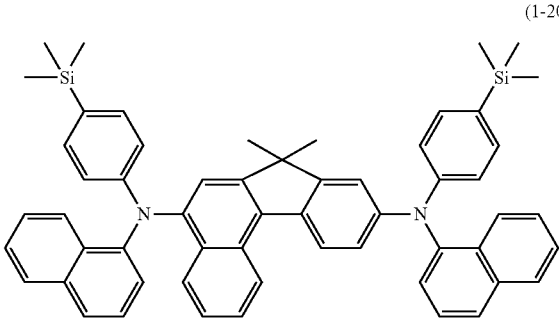
(1-21)
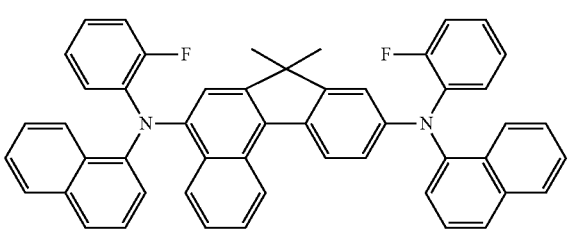
(1-22)
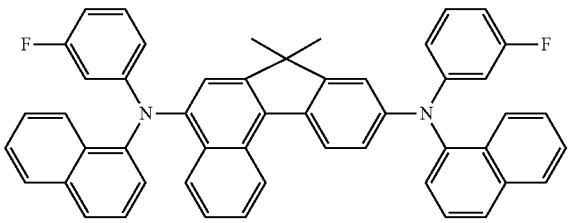

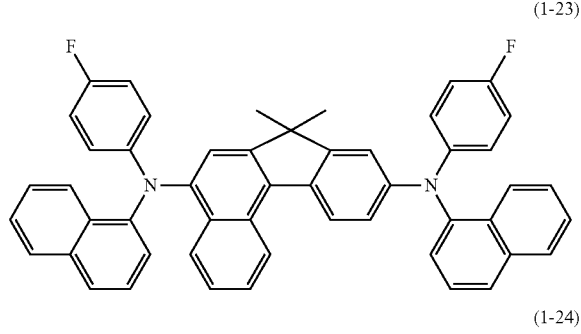
(1-23)
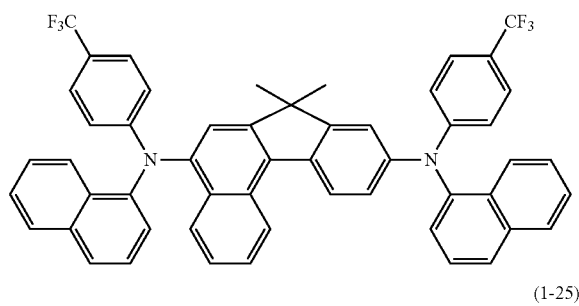
(1-24)
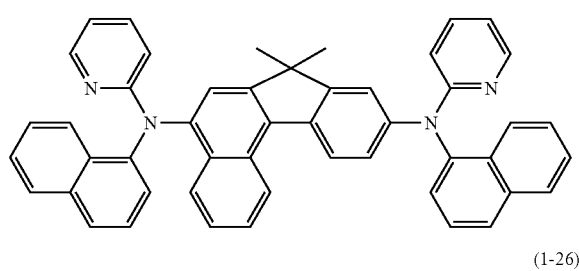
(1-25)
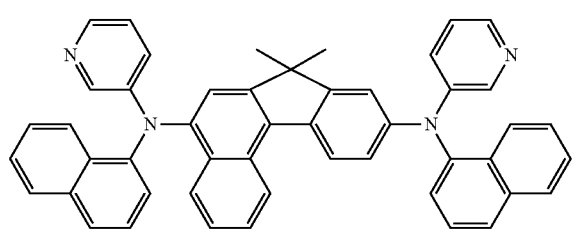
(1-26)
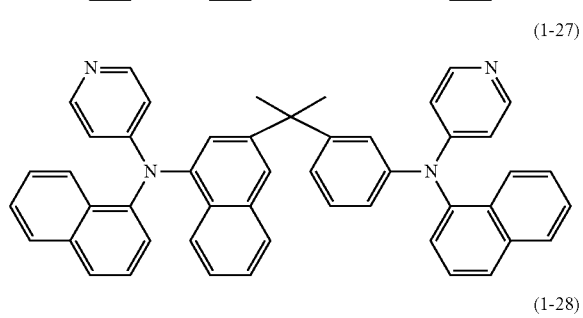
(1-27)
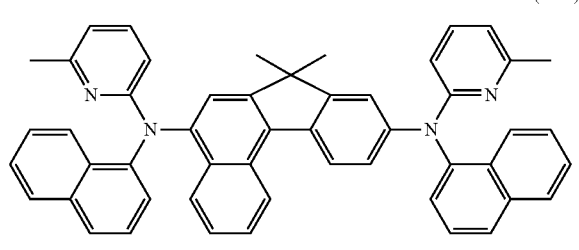
(1-28)
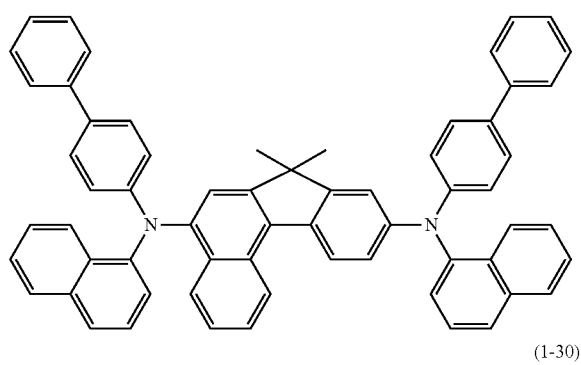
(1-29)
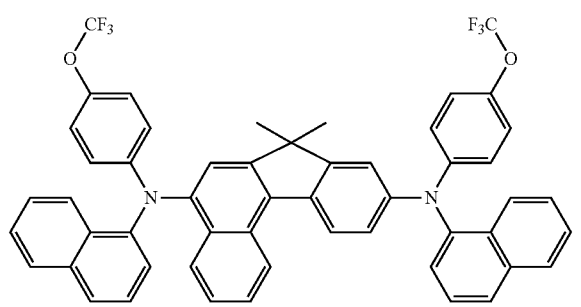
(1-30)
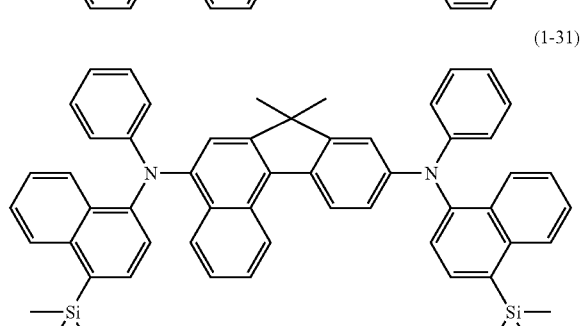
(1-31)
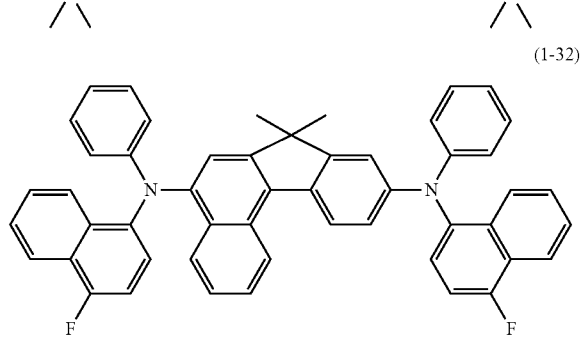
(1-32)
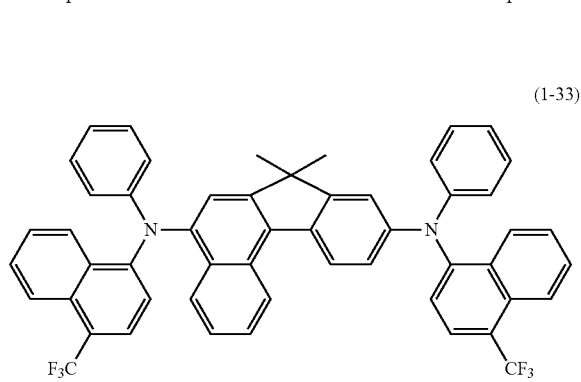
(1-33)

(1-34)
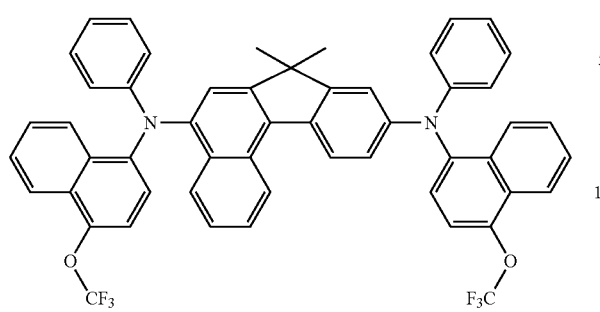
(1-35)
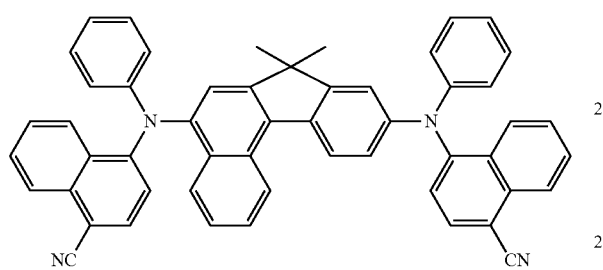
(1-36)
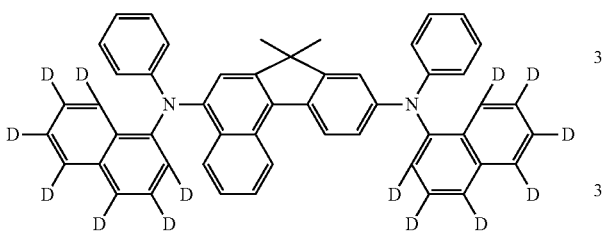
(1-37)
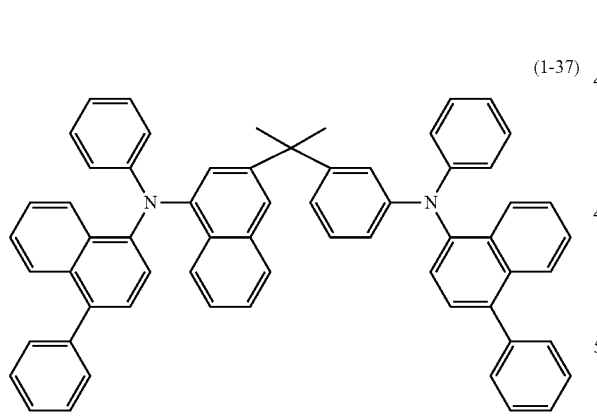
(1-38)
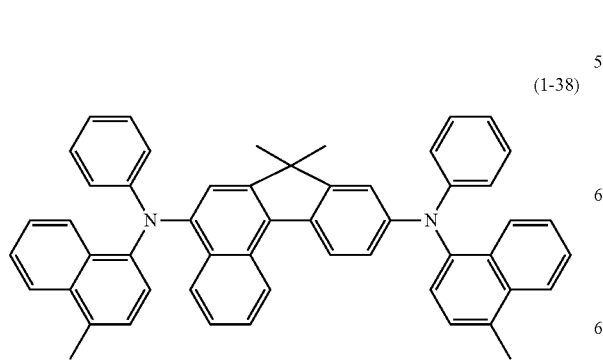
(1-39)
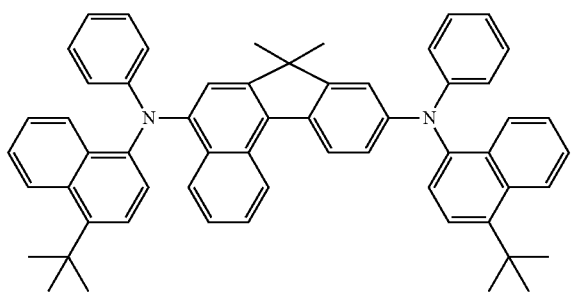
(1-40)
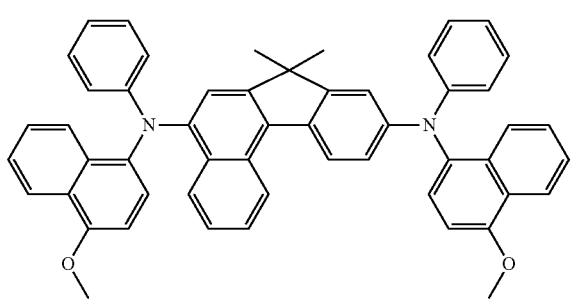
(1-41)
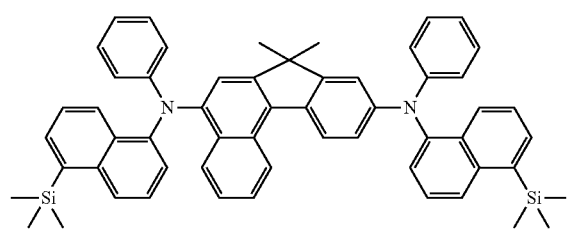
(1-42)
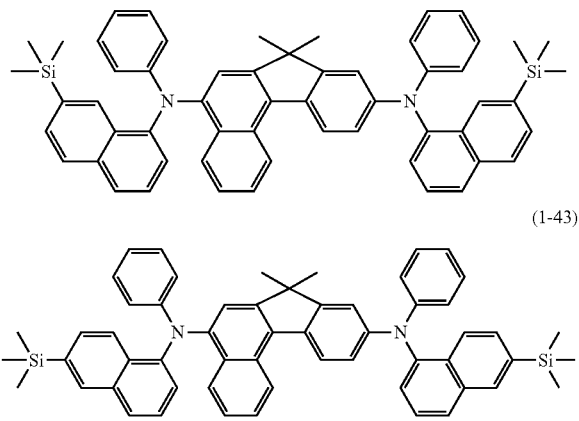
(1-43)
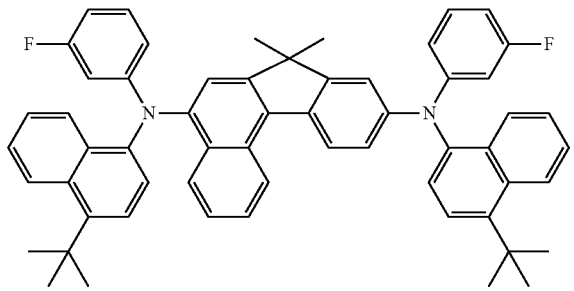
(1-44)

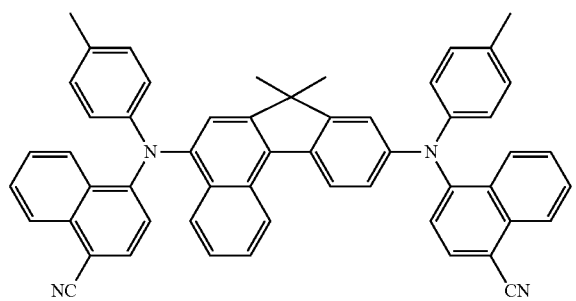 (1-45)
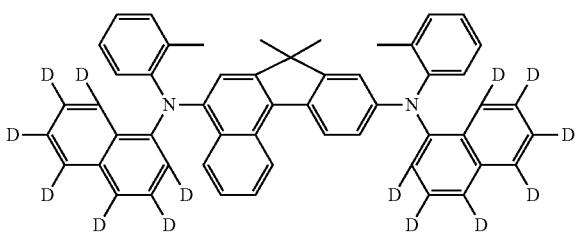 (1-46)
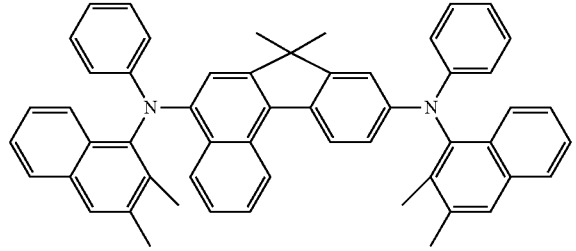 (1-47)
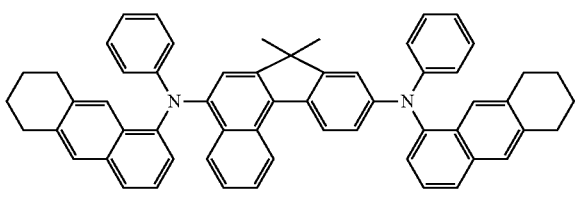 (1-48)
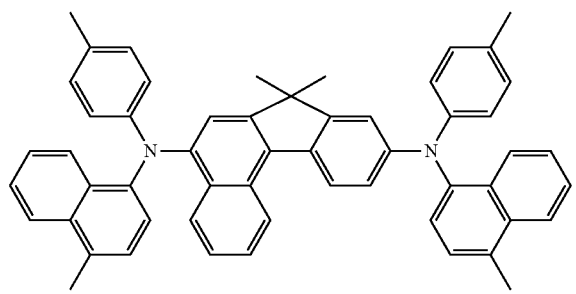 (1-49)
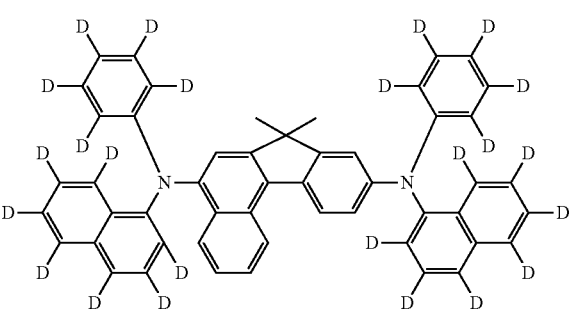 (1-50)
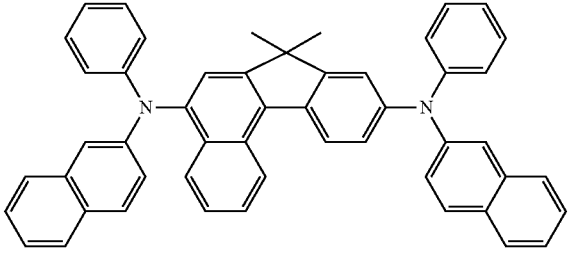 (1-51)
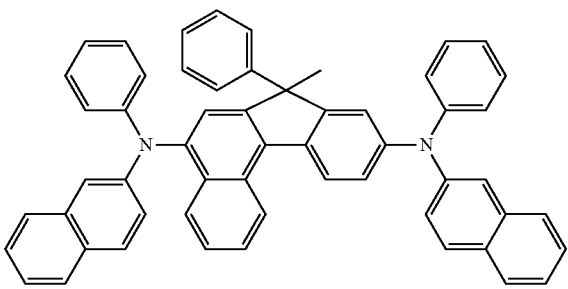 (1-52)
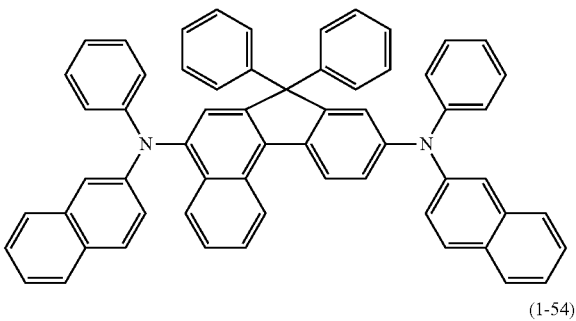 (1-53)
(1-54)

(1-55)
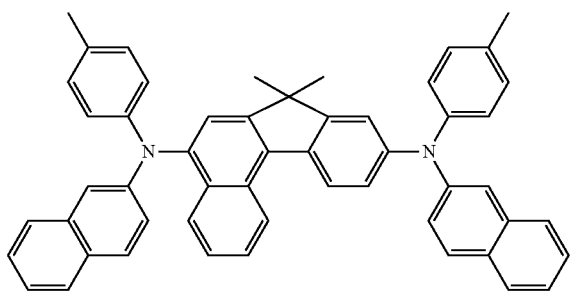
(1-56)
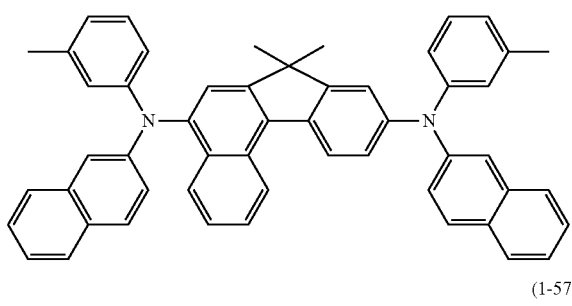
(1-57)
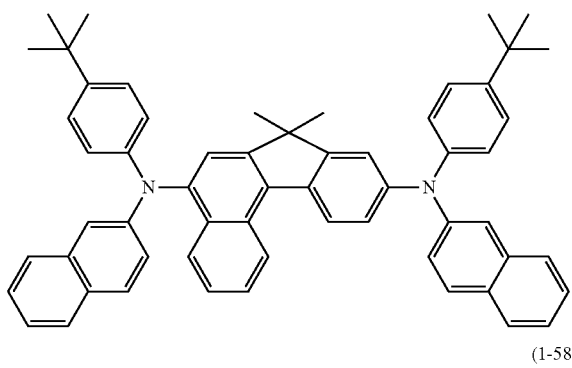
(1-58)
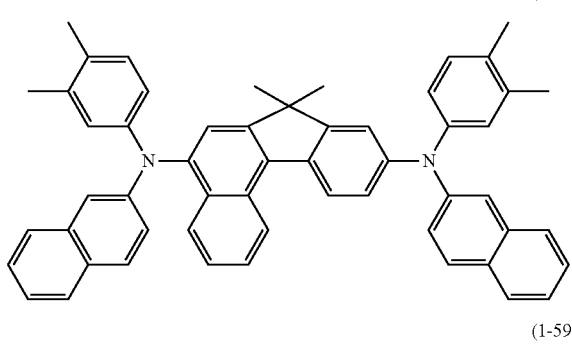
(1-59)
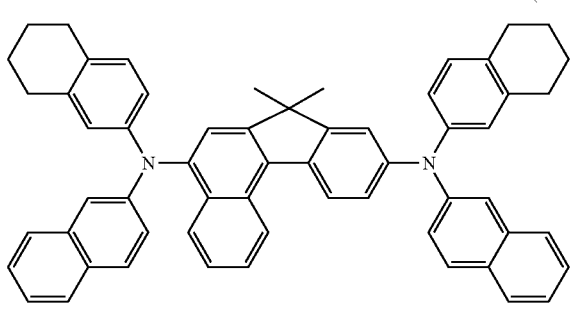
(1-60)
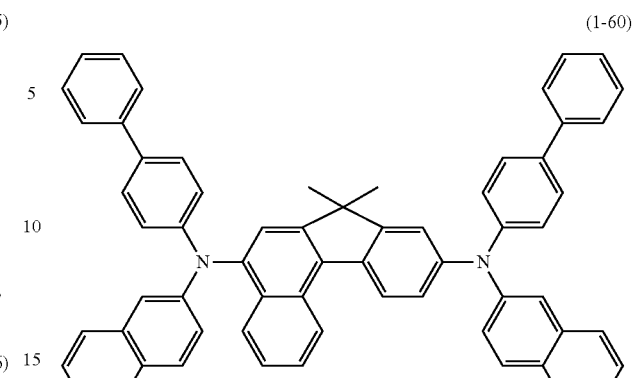
(1-61)
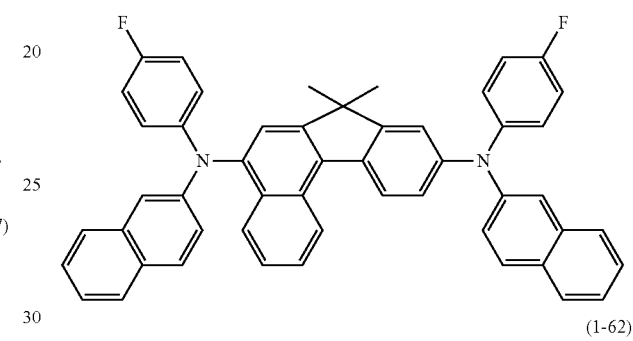
(1-62)
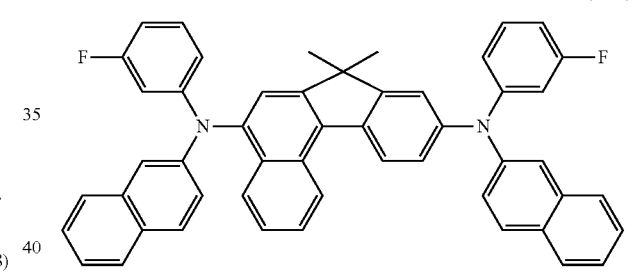
(1-63)
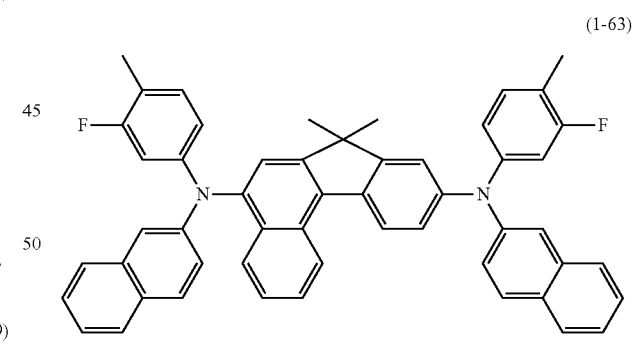
(1-64)
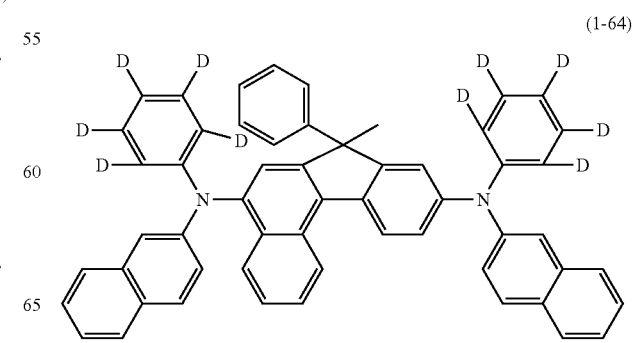

(1-65)
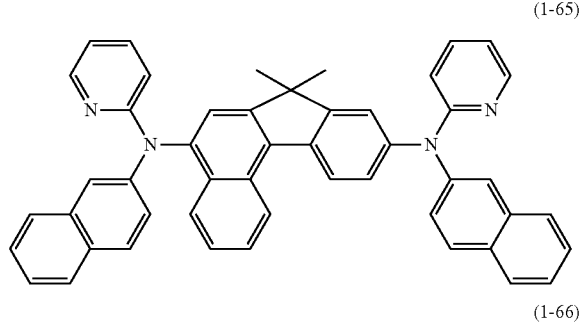
(1-66)
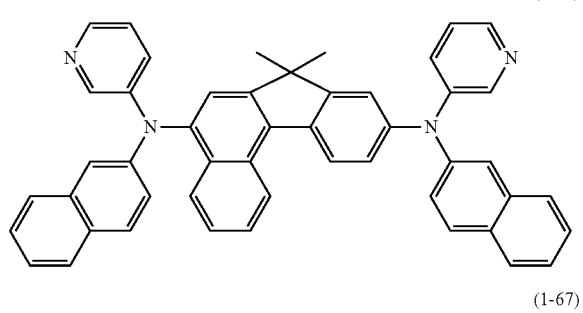
(1-67)
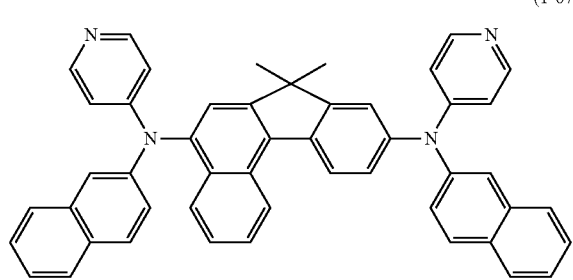
(1-68)
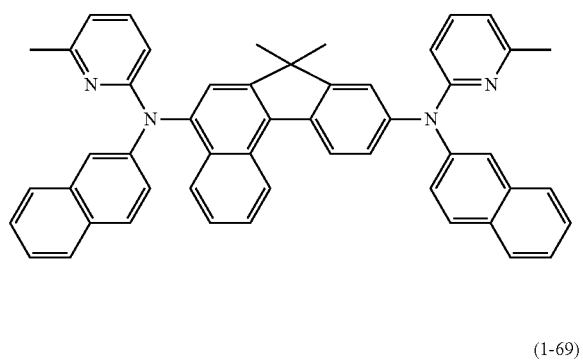
(1-69)
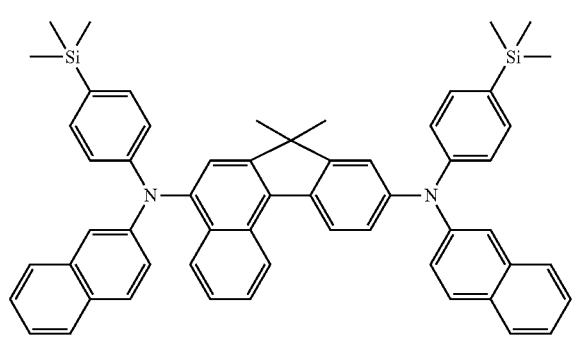
(1-70)
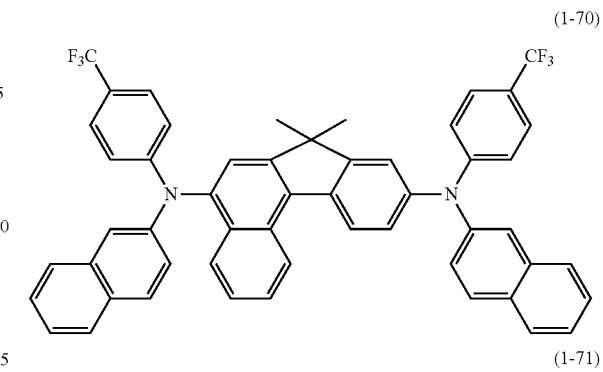
(1-71)
(1-72)
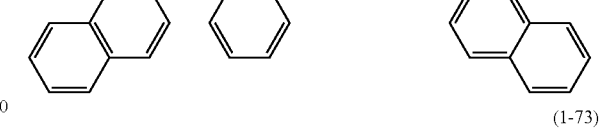
(1-73)
(1-74)
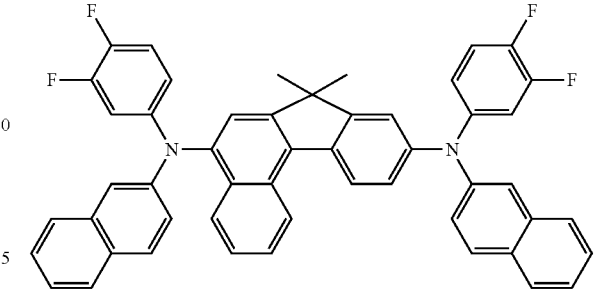

(1-75)
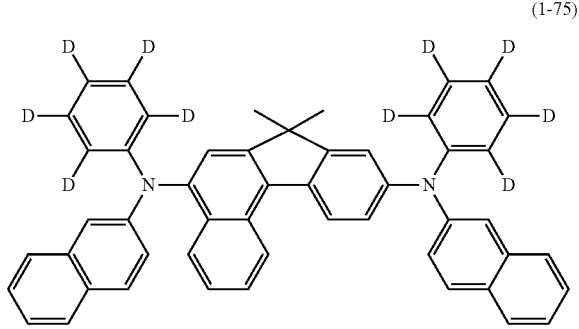
(1-76)
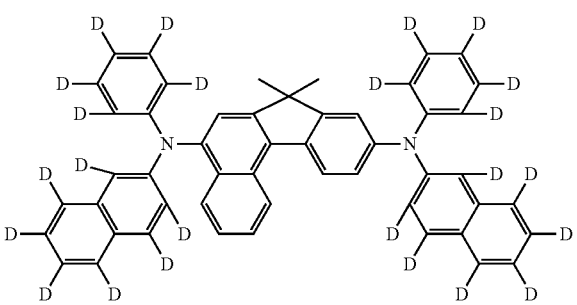
(1-77)
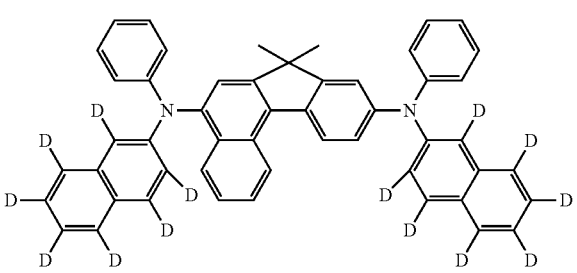
(1-78)
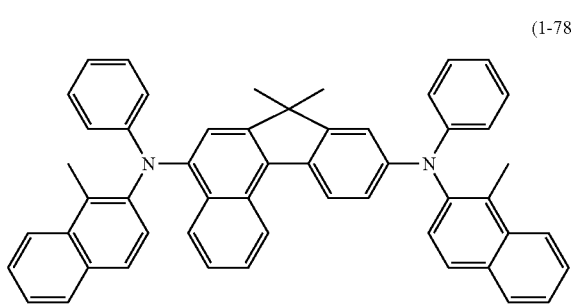
(1-79)
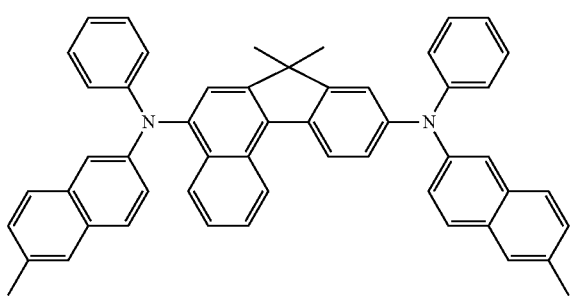
(1-80)
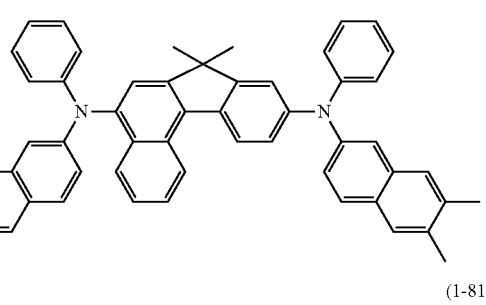
(1-81)
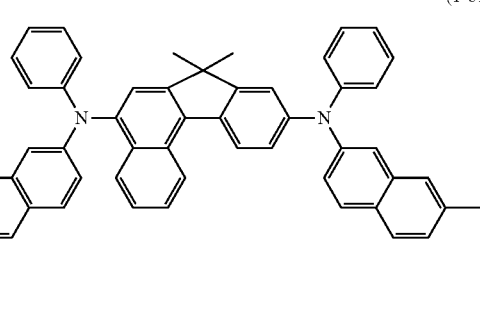
(1-82)
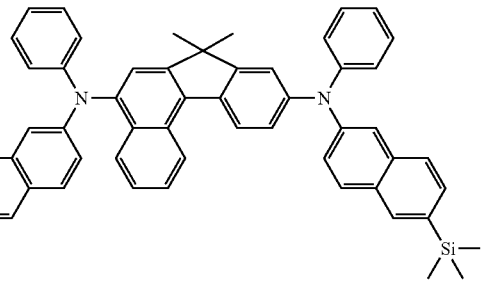
(1-83)
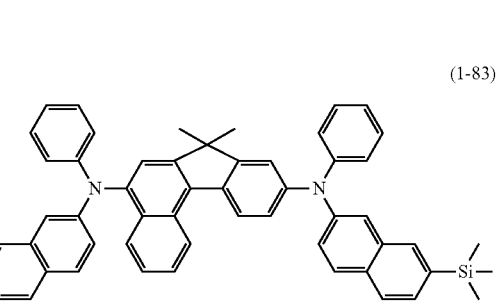
(1-84)

(1-85)

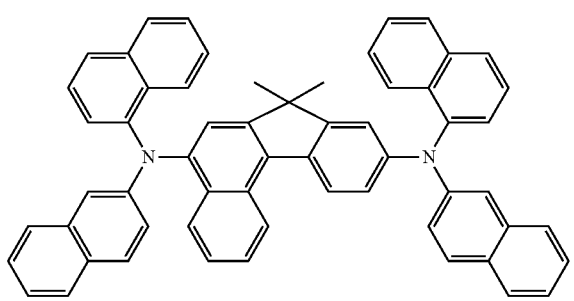

2. Method for Producing Benzofluorene Compound

As represented by the general formula (1), the compound having a benzofluorene backbone to which two diarylamino groups are bound can be produced by utilizing an existing reaction such as the Buchwald-Hartwig reaction or the Ullmann reaction.

The Buchwald-Hartwig reaction is a process for coupling an aromatic halide and a primary aromatic amine or a secondary aromatic amine by using a palladium catalyst or a copper catalyst in the presence of a base. A specific example of the reaction pathway for obtaining the compound represented by the general formula (1) by this process is as follows (Schemes 1 to 3).

The reaction shown in the first stage of Scheme 1 is the Suzuki coupling, and the reaction can also be conducted if group X and group Y in the two compounds to be reacted are interchanged. Furthermore, in this reaction of the first stage, the Negishi coupling can also be used instead of the Suzuki coupling, and in this case, a zinc chloride complex is used instead of boron acid or a boron acid ester as the compound having group Y. Furthermore, also in this case of the Negishi coupling, the reaction can be conducted in a similar manner to that mentioned above, if group X and group Y are interchanged (namely, a zinc chloride complex of naphthalene is used). In addition, although a raw material that has been substituted with —COOR on the position adjacent to the carbon to be coupled of the benzene ring in advance is used so as to form a five-membered ring after the coupling reaction in Scheme 1, a raw material substituted with —COOR at the 2-position of the naphthalene ring (next to the carbon to be coupled) can also be used. With respect to the process for synthesizing an aromatic dihalide explained in Scheme 1, for example, WO 2005/056633 A is referred to.

Scheme 2 is a process for subsequently binding two Ar moieties and two naphthalene moieties to an aromatic dihalide, or conversely, it is also possible to prepare an amine with naphthalene moieties and a halogenated Ar, bind the two naphthalene moieties and then bind the two Ar moieties. Furthermore, Scheme 3 is a process in which a diarylamine is prepared in advance and bound to the aromatic dihalide. In Scheme 3, the diarylamine is synthesized from an amine with Ar moieties and a halogenated naphthalene, or conversely, it is also possible to synthesize the diarylamine from an amine of a naphthalene moiety and a halogenated Ar.

$R^1$, $R^2$, $R^3$, n1, n2 and Ar in the respective schemes correspond to those respectively used in the general formula (1).

(Scheme 1) Synthesis of aromatic dihalide

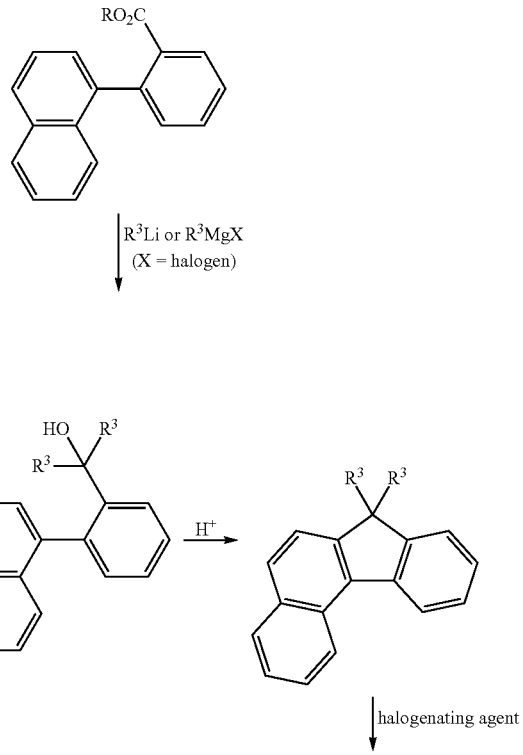

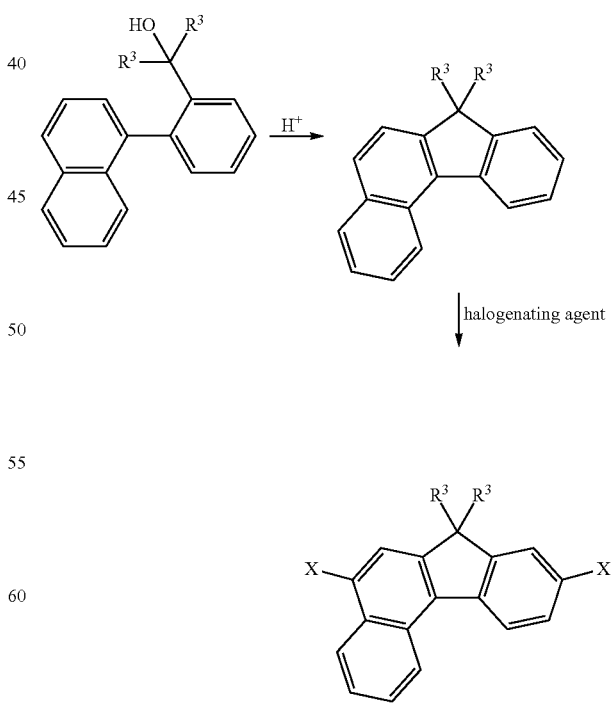

(Scheme 2)

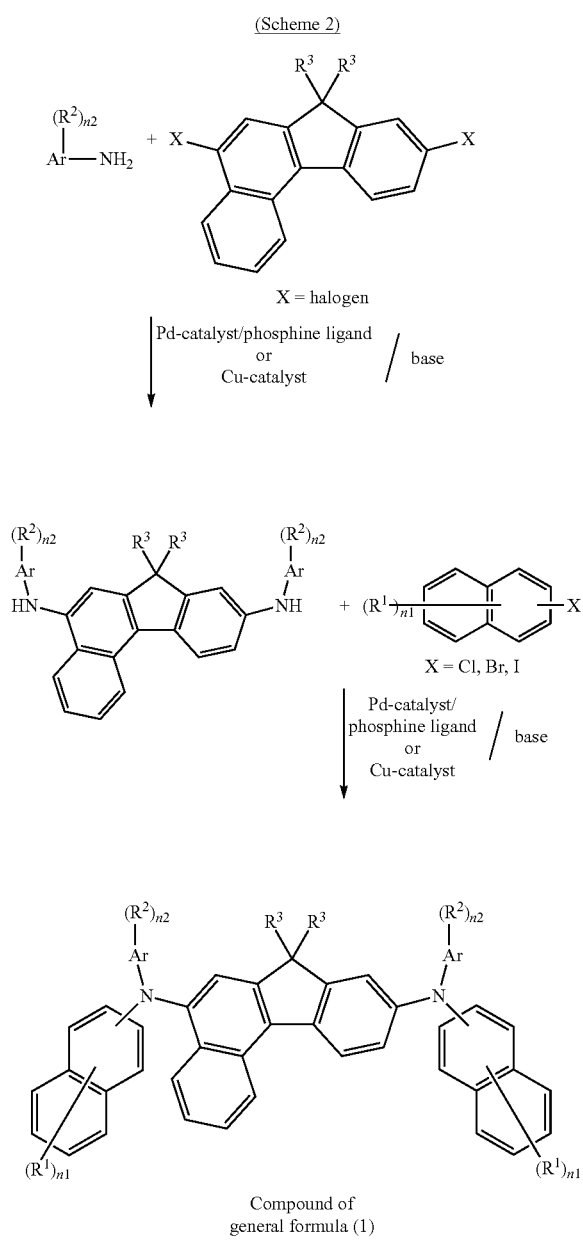

Compound of general formula (1)

(Scheme 3)

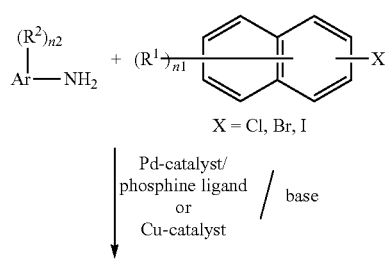

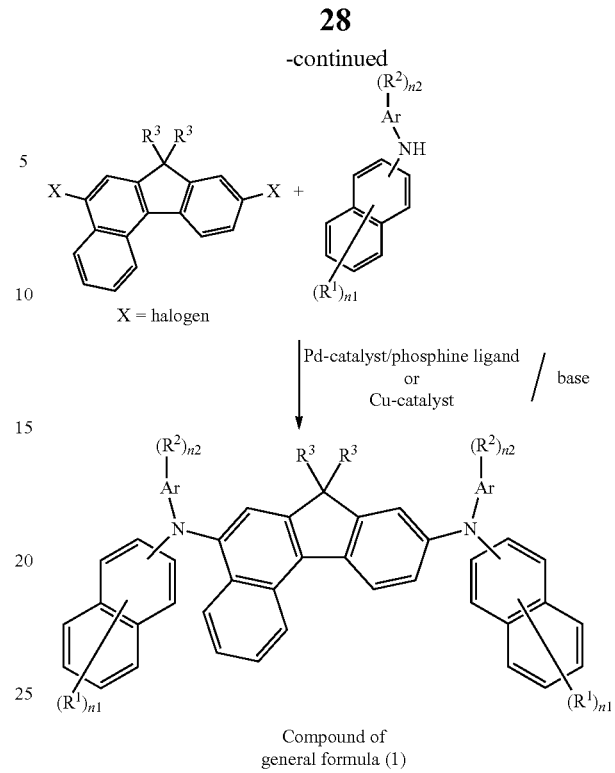

Compound of general formula (1)

Specific examples of the palladium catalyst used in the above-mentioned reactions include tetrakis(triphenylphosphine)palladium(0): Pd(PPh$_3$)$_4$, bis(triphenylphosphine)palladium(II)dichloride: PdCl$_2$(PPh$_3$)$_2$, palladium(II)acetate: Pd(OAc)$_2$, tris(dibenzylideneacetone)dipalladium(0): Pd$_2$(dba)$_3$, tris(dibenzylideneacetone)dipalladium(0)chloroform complex: Pd$_2$(dba)$_3$.CHCl$_3$, bis(dibenzylideneacetone)palladium(0): Pd(dba)$_2$, PdCl$_2$\{P(t-Bu)-2-(p-NMe$_2$-Ph)\}$_2$, palladium bis(dibenzylidene) and the like.

In order to promote the reaction, a phosphine compound may be added to these palladium compounds as necessary. Specific examples of the phosphine compound are tri(t-butyl)phosphine, tricyclohexylphosphine, 1-(N,N-dimethylaminomethyl)-2-(di-t-butylphosphino)ferrocene, 1-(N,N-dibutylaminomethyl)-2-(di-t-butylphosphino)ferrocene, 1-(methoxymethyl)-2-(di-t-butylphosphino)ferrocene, 1,1'-bis(di-t-butylphosphino)ferrocene, 2,2'-bis(di-t-butylphosphino)-1,1'-binaphthyl, 2-methoxy-2'-(di-t-butylphosphino)-1,1'-binaphthyl, 1,1'-bis(diphenylphosphino)ferrocene, bis(diphenylphosphino)binaphthyl, 4-dimethylaminophenyl di-t-butylphosphine, phenyl di-t-butylphosphine and the like.

Specific examples of the base used in this reaction are sodium carbonate, potassium carbonate, cesium carbonate, sodium hydrogen carbonate, sodium hydroxide, potassium hydroxide, barium hydroxide, sodium ethoxide, sodium t-butoxide, sodium acetate, potassium triphosphate, potassium fluoride and the like.

Furthermore, specific examples of the solvent used in this reaction are benzene, 1,2,4-trimethylbenzene, toluene, xylene, N,N-dimethylformamide, tetrahydrofuran, diethyl ether, t-butyl methyl ether, 1,4-dioxane, methanol, ethanol, isopropyl alcohol and the like. These solvents can be suitably selected depending on the structures of the aromatic halide, triflate, aromatic boron acid ester and aromatic boron acid to be reacted. The solvent may be used alone or as a mixed solvent.

Furthermore, the Ullmann reaction is a process for coupling an aromatic halide with a primary aromatic amine or a secondary aromatic amine by using a copper catalyst in the presence of a base. Specific examples of the copper catalyst used in the Ullmann reaction are copper powder, copper chloride, copper bromide or copper iodide, and the like. Furthermore, the specific examples of the base used in this reaction can be selected from bases that are similar to those for the Buchwald-Hartwig reaction. In addition, specific examples of the solvent used in the Ullmann reaction are nitrobenzene, dichlorobenzene, N,N-dimethylformamide and the like.

The above-mentioned Schemes 1 to 3 are especially useful in producing a type having the same structure in the two diaryl amino groups that are bound to the benzofluorene backbone. On the other hand, in the case when the substituents $R^1$ and $R^2$ and the numbers and the formats of binding to the amino groups of the Ars and naphthyl groups are different in the general formula (1), a benzofluorene compound having a diarylamino group having a different structure is formed. In the case when this type of benzofluorene compound is to be produced, it is preferable to use a selective reaction by utilizing the difference in the activities of the reactive substituents, or to utilize purification and separation techniques and the like. Specific examples of this reaction pathway are as follows (Schemes 4 to 7).

The reaction shown in the first stage of Scheme 4 is the Suzuki coupling, and group $X^1$ and group $X^2$ are groups having different reaction activities so that group Y and group $X^1$ in the two compounds to be reacted are selectively reacted. For example, a compound wherein group $X^1$ is triflate and group $X^2$ is chlorine is preferable in view of easy availability of the raw materials.

Furthermore, the reaction can also be conducted if group $X^1$ and group Y in the two compounds to be reacted are interchanged. In this case, group Y and group $X^2$ by which the benzoate is substituted are set to be group Y>group $X^2$. In addition, the Negishi coupling can also be used instead of the Suzuki coupling in this reaction of the first stage, and in this case, a zinc chloride complex is used instead of boron acid or a boron acid ester as the compound having group Y. Also in this case of the Negishi coupling, the reaction can be conducted if group $X^1$ and group Y are interchanged (that is, a zinc chloride complex of the benzoate is used) in a manner similar to that mentioned above.

Furthermore, although an example in which halogens having different reaction activities are utilized as $X^2$ and $X^3$ of the aromatic dihalide is explained in Scheme 4, it is also possible to make the reaction activities of $X^2$ and $X^3$ different by also utilizing triflate. In this case, an aromatic monohalide monotriflate can be synthesized by forming a benzofluorene ring according to Scheme 6 by using as raw materials, for example, a 1,4-halogenated naphthalene instead of the naphthalene having group Y and a benzoate in which the $X^1$ and $X^2$ by which the benzoate is substituted are respectively replaced with a halogen group (or a triflate group) and a methoxy group, and by further demethylating and triflating the methoxy group. Furthermore, although a raw material having a benzene ring that has been substituted with —COOR in advance at the position adjacent to the carbon to be coupled is used so as to form a five-membered ring after the coupling reaction, it is also possible to use a raw material having a naphthalene ring substituted with —COOR at the 2-position (next to the carbon to be coupled). With respect to the process for the synthesis of the aromatic halide explained in Scheme 4, for example, WO 2005/056633 A is referred to.

By conducting up to the halogenated reaction of the fourth stage of Scheme 4, a dihalide of benzofluorene (or a halogen triflate) is obtained and can be used in Scheme 5 mentioned below. Furthermore, as mentioned above, since group $X^2$ (for example, chlorine) has low reaction activity, a group having higher reaction activity than that of this group is introduced to group $X^3$. For this reason, as the halogenating agent used in the fourth stage, for example, a brominating agent or an iodizing agent is preferable, and an iodizing agent is more preferable. Scheme 5 is a process in which a diarylamino group is synthesized in advance, and this is bound to a dihalide of benzofluorene (or a halogen triflate).

Furthermore, it is also possible to synthesize the compound represented by the general formula (1) by using a monohalide of benzofluorene obtained by the reactions up to the third stage of Scheme 4. Schemes 6 and 7 are reaction pathways for this case, and are a process in which a monohalide of benzofluorene is used as a raw material, and the moieties that correspond to the four aryl groups (two Ars and two naphthyls) in total are bonded one by one, and a process in which diarylamino groups that have been synthesized in advance are bonded one by one. Meanwhile, although the diarylamino group is bonded from the benzene side by using a monohalide in which the reactive substituent $X^2$ is bound to the benzene side of benzofluorene in Schemes 6 and 7, conversely, it is also possible to synthesize a monohalide in which a reactive substituent is bonded to the naphthalene side by suitably changing the raw materials in Scheme 4 and to bond the diarylamino group from the naphthalene side by using this.

$R^1$, $R^2$, $R^3$, n1, n2 and Ar used in the respective schemes respectively correspond to those used in the general formula (1).

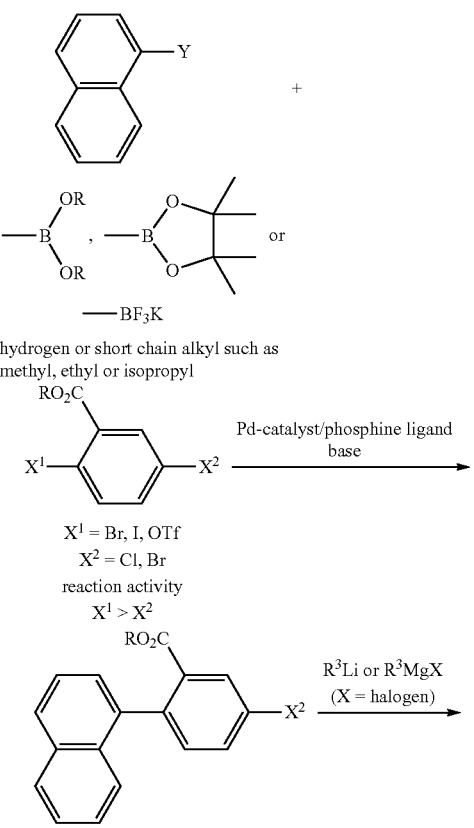

(Scheme 4) Synthesis of aromatic mono-, di-halide

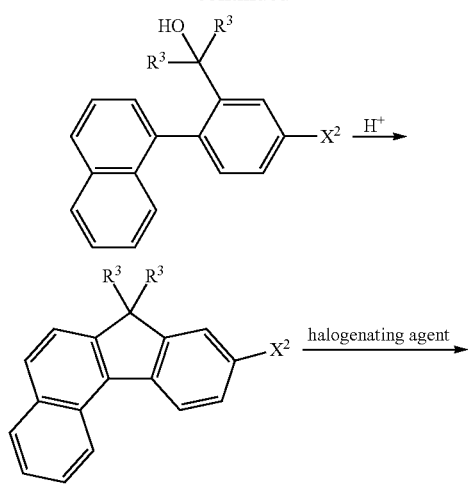
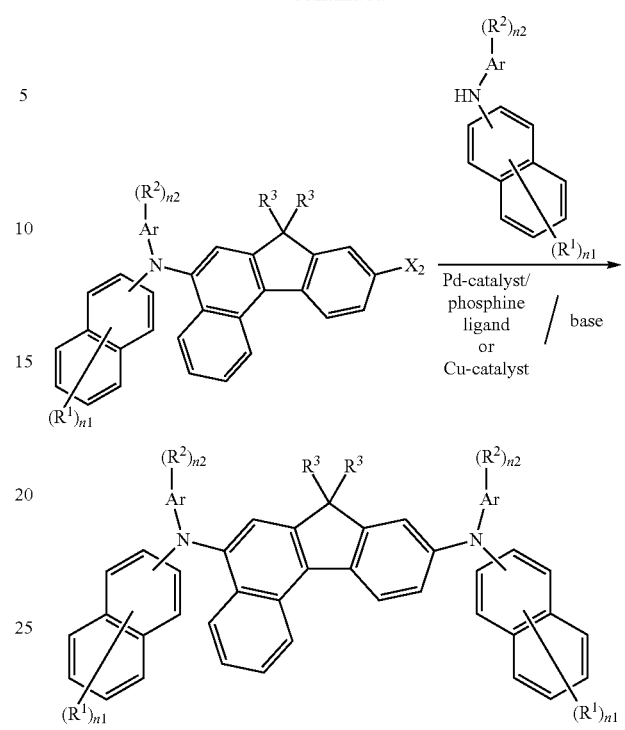
Compound of general formula (1)
(Scheme 5)
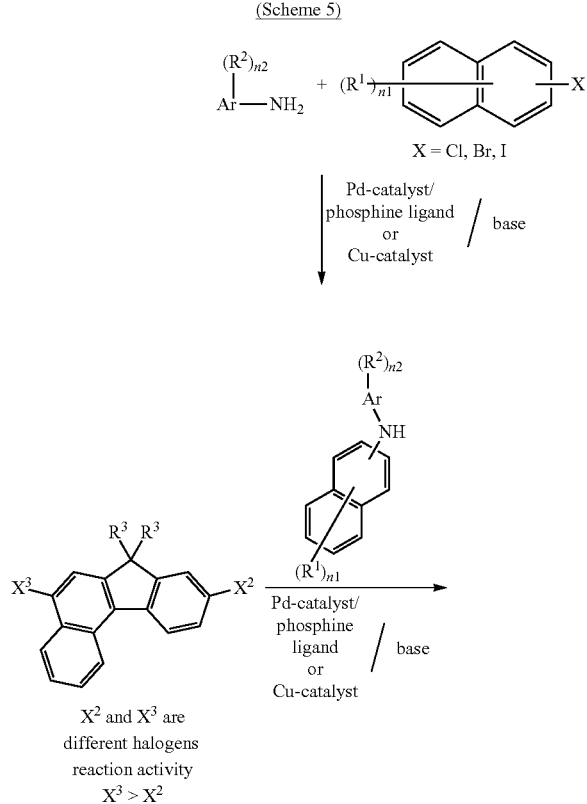
(Scheme 6)
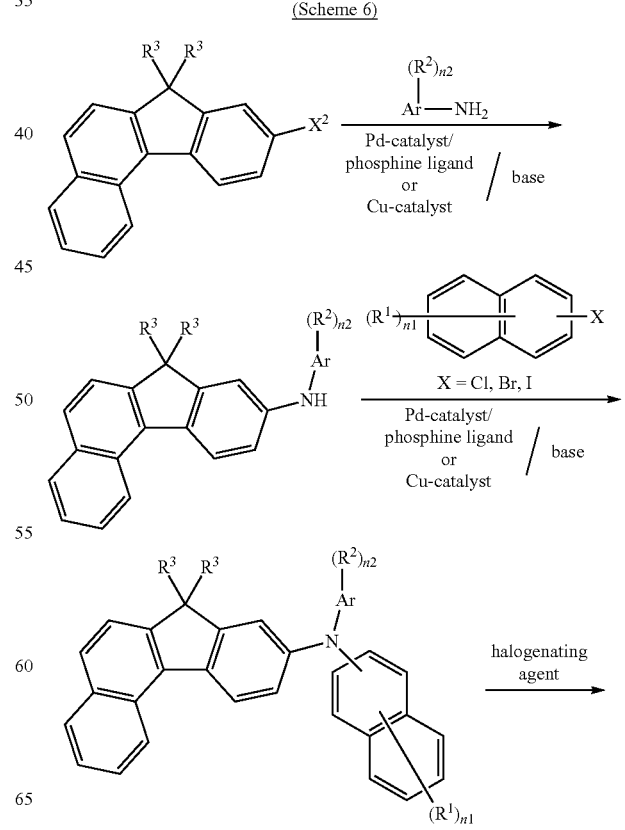

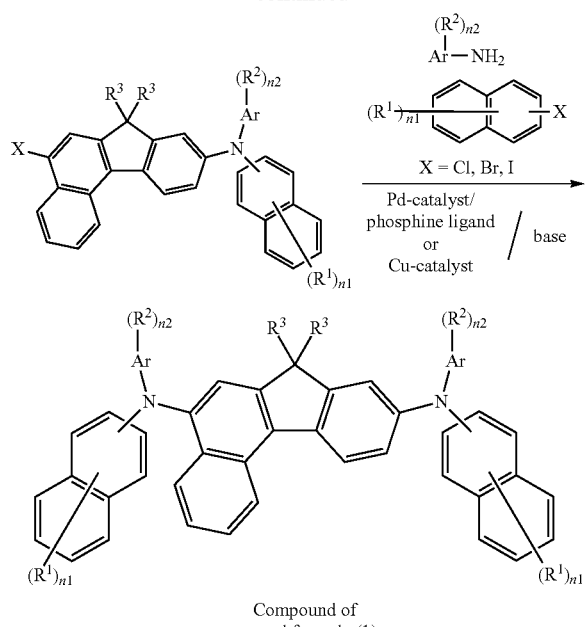

Compound of
general formula (1)

(Scheme 7)

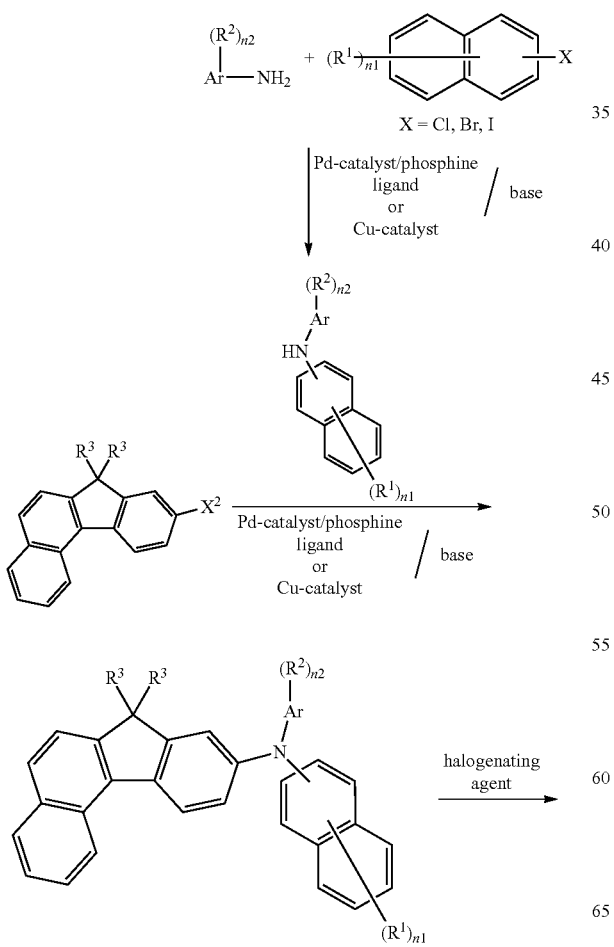

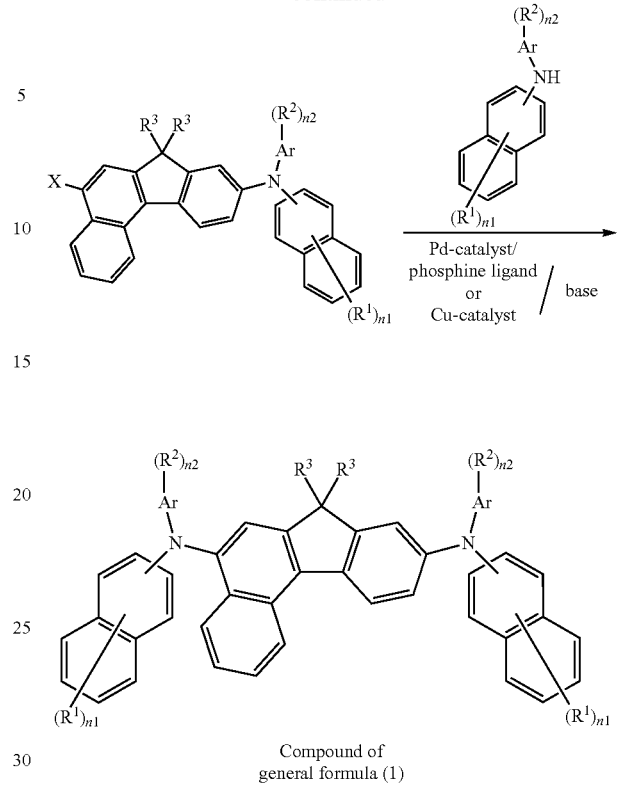

Compound of
general formula (1)

Furthermore, the compound represented by the general formula (1) can also be produced by producing a N,N-substituted-1-naphthylamine having a reaction active group at the 4-position and a 3-alkoxycarbonyl-N,N-substituted aniline having a reaction active group at the 4-position in advance according to the above-mentioned production processes, subjecting these to a coupling reaction, and then conducting a cyclization reaction (Scheme 8). A reaction in which a raw material in which —COOR for the cyclization reaction is bonded to the 3-position of naphthylamine is used (Scheme 9) is also preferably used. In these schemes, the production can be conducted whether the two diarylamino groups that are bonded to the benzofluorene backbone are the same type of structure or different types of structures. The reaction shown in the first stage of Scheme 8 and Scheme 9 is the Suzuki coupling, and the reaction can also be conducted if group X and group Y in the two compounds to be reacted are interchanged. Furthermore, in this reaction of the first stage, the Negishi coupling can also be used instead of Suzuki coupling, and in this case, a zinc chloride complex is used as the compound having group Y instead of boron acid or a boron acid ester. Furthermore, also in this case of the Negishi coupling, the reaction can be conducted in a similar manner to that mentioned above if group X and group Y are interchanged (that is, a zinc chloride complex of a diarylamino-substituted naphthalene is used). $R^1$, $R^2$, $R^3$, n1, n2 and Ar in the respective schemes respectively correspond to those used in the general formula (1).

(Scheme 8)
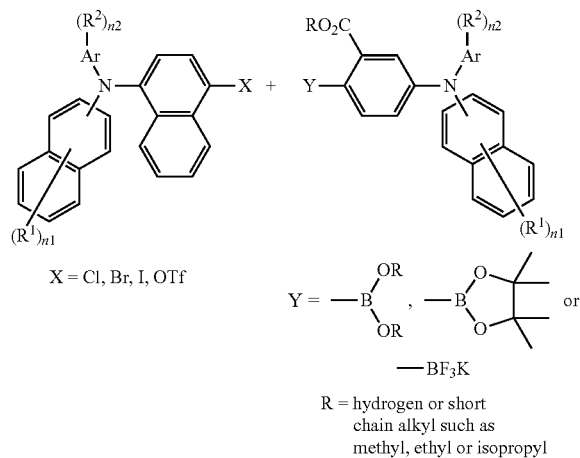
X = Cl, Br, I, OTf
Y = —B(OR)(OR), pinacol boronate or —BF$_3$K
R = hydrogen or short chain alkyl such as methyl, ethyl or isopropyl
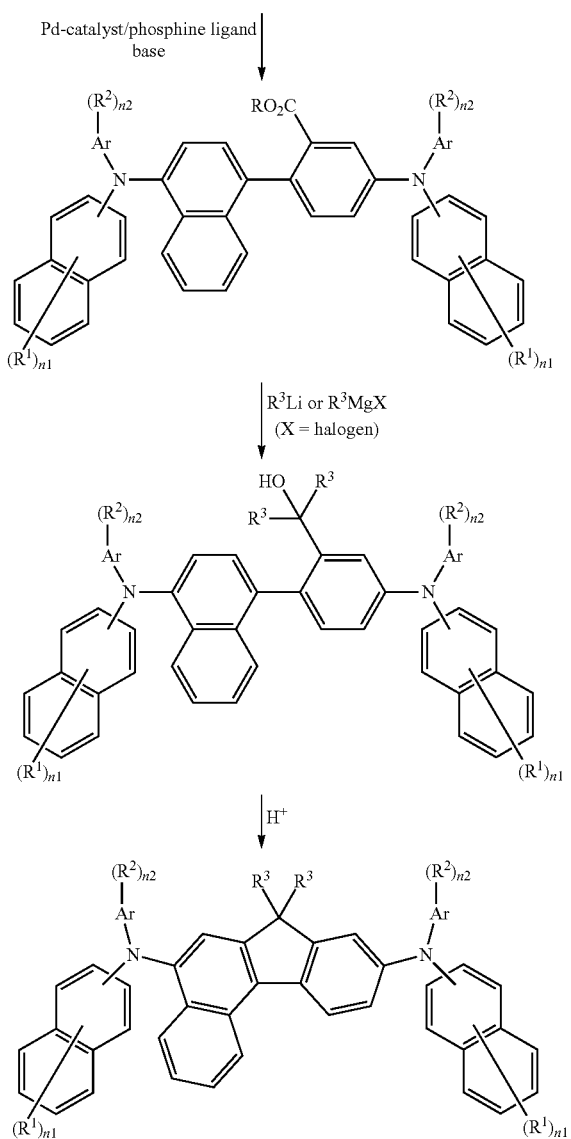
Compound of general formula (1)
(Scheme 9)
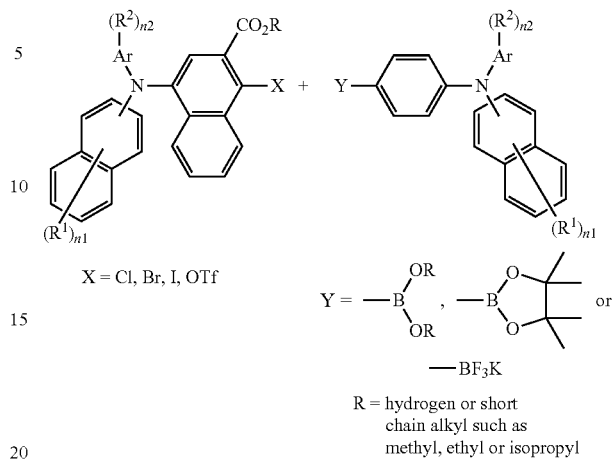
X = Cl, Br, I, OTf
Y = —B(OR)(OR), pinacol boronate or —BF$_3$K
R = hydrogen or short chain alkyl such as methyl, ethyl or isopropyl
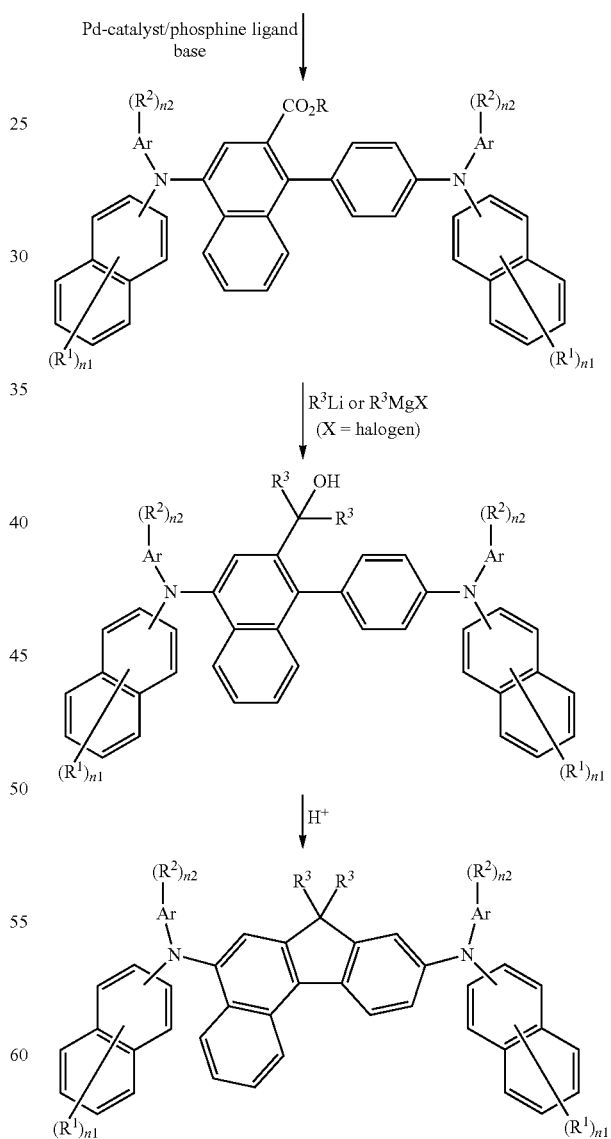
Compound of general formula (1)

Furthermore, the compound of the present invention also encompasses compounds in which at least a part of hydrogen atoms is substituted with deuterium, and such compounds can be synthesized in a similar manner to that mentioned above by using a raw material in which desired position(s) has/have been deuterated.

3. Organic Electroluminescent Device

The benzofluorene compound according to the present invention can be used, for example, as a material for an organic electroluminescent device.

The organic electroluminescent device according to this exemplary embodiment will be explained in detail. FIG. 1 is a schematic cross-sectional view showing the organic electroluminescent device according to this exemplary embodiment.

<Structure of Organic Electroluminescent Device>

The organic electroluminescent device 100 shown in FIG. 1 has a substrate 101, an anode 102 disposed on the substrate 101, a hole injection layer 103 disposed on the anode 102, a hole transport layer 104 disposed on the hole injection layer 103, a luminescent layer 105 disposed on the hole transport layer 104, an electron transport layer 106 disposed on the luminescent layer 105, an electron injection layer 107 disposed on the electron transport layer 106, and a cathode 108 disposed on the electron injection layer 107.

The organic electroluminescent device 100 may also have a constitution having, for example, the substrate 101, the cathode 108 disposed on the substrate 101, the electron injection layer 107 disposed on the cathode 108, the electron transport layer 106 disposed on the electron injection layer 107, the luminescent layer 105 disposed on the electron transport layer 106, the hole transport layer 104 disposed on the luminescent layer 105, the hole injection layer 103 disposed on the hole transport layer 104, and the anode 102 disposed on the hole injection layer 103, by reversing the order of preparation.

It is not necessary that all of the above-mentioned respective layers are essential, and the smallest constitutional unit is a constitution formed of the anode 102, the luminescent layer 105 and the cathode 108, and the hole injection layer 103, the hole transport layer 104, the electron transport layer 106 and the electron injection layer 107 are layers that are optionally disposed. Furthermore, each of the above-mentioned respective layers may be formed of a single layer or plural layers.

Besides the above-mentioned "substrate/anode/hole injection layer/hole transport layer/luminescent layer/electron transport layer/electron injection layer/cathode", the embodiment of the layers that constitute the organic electroluminescent device may be a constitutional embodiment of "substrate/anode/hole transport layer/luminescent layer/electron transport layer/electron injection layer/cathode", "substrate/anode/hole injection layer/luminescent layer/electron transport layer/electron injection layer/cathode", "substrate/anode/hole injection layer/hole transport layer/luminescent layer/electron injection layer/cathode", "substrate/anode/hole injection layer/hole transport layer/luminescent layer/electron transport layer/cathode", "substrate/anode/luminescent layer/electron transport layer/electron injection layer/cathode", "substrate/anode/hole transport layer/luminescent layer/electron injection layer/cathode", "substrate/anode/hole transport layer/luminescent layer/electron transport layer/cathode", "substrate/anode/hole injection layer/luminescent layer/electron injection layer/cathode", "substrate/anode/hole injection layer/luminescent layer/electron transport layer/cathode", "substrate/anode/hole injection layer/hole transport layer/luminescent layer/cathode", "substrate/anode/hole injection layer/luminescent layer/cathode", "substrate/anode/hole transport layer/luminescent layer/cathode", "substrate/anode/luminescent layer/electron transport layer/cathode", "substrate/anode/luminescent layer/electron injection layer/cathode" or "substrate/anode/luminescent layer/cathode".

<Substrate in Organic Electroluminescent Device>

The substrate 101 forms the substrate of the organic electroluminescent device 100, and quartz, glass, metals, plastics and the like are generally used therefor. The substrate 101 is formed into a plate-shape, a film-shape or a sheet-shape according to the intended purpose, and for example, glass plates, metal plates, metal foils, plastic films or plastic sheets or the like are used. Among these, glass plates, and plates made of transparent synthetic resins such as polyesters, polymethacrylates, polycarbonates and polysulfones are preferable. As the glass substrate, soda lime glass, non-alkali glass and the like are used, and the thickness may be a thickness that is sufficient to retain mechanical strength, for example, may be 0.2 mm or more. The upper limit value of the thickness is, for example, 2 mm or less, preferably 1 mm or less. As the material for the glass, non-alkali glass is more preferable since it is preferable that the amount of eluted ion from the glass is small, and soda lime glass with a barrier coating of $SiO_2$ or the like is also commercially available, and thus this can be used. Furthermore, a gas barrier film of a dense silicon oxide film or the like may be disposed on at least one surface of the substrate 101 so as to enhance the gas barrier property, and especially, in the case when a plate, film or sheet made of a synthetic resin having low gas barrier property is used as the substrate 101, it is preferable to dispose a gas barrier film.

<Anode in Organic Electroluminescent Device>

The anode 102 plays a role in injecting holes into the luminescent layer 105. In the case when the hole injection layer 103 and/or the hole transport layer 104 is/are disposed between the anode 102 and the luminescent layer 105, holes are injected into the luminescent layer 105 through the layer(s).

As the material for forming the anode 102, inorganic compounds and organic compounds are exemplified. Examples of the inorganic compounds include metals (aluminum, gold, silver, nickel, palladium, chromium and the like), metal oxides (indium oxide, tin oxide, indium-tin oxide (ITO) and the like), halogenated metals (copper iodide and the like), copper sulfide, carbon black, ITO glass, NESA glass and the like. Examples of the organic compounds include electroconductive polymers such as polythiophenes such as poly(3-methylthiophene), polypyrroles and polyanilines. In addition, the material can be suitably selected from substances that are used as anodes for organic electroluminescent devices and used.

The resistance of the transparent electrode is not especially limited as long as a sufficient current for the luminescence of the luminescent device can be fed, but a low resistance is desirable in view of the consumed electrical power of the luminescent device. For example, although any ITO substrate of 300Ω/□ or less functions as an element electrode, it is currently possible to supply a substrate of about 10Ω/□. Therefore, it is especially desirable to use a low-resistant product of, for example, 100 to 5Ω/□, preferably 50 to 5Ω/□. The thickness of the ITO can be selected according to the resistance value, but the ITO is generally used between 100 to 300 nm in many cases.

<Hole Injection Layer and Hole Transport Layer in Organic Electroluminescent Device>

The hole injection layer 103 plays a role in efficiently injecting the holes that have been transferred from the anode 102 into the luminescent layer 105 or the hole transport layer 104. The hole transport layer 104 plays a role in efficiently transporting the holes that have been injected from the anode 102 or the holes that have been injected from the anode 102 through the hole injection layer 103 to the luminescent layer 105. The hole injection layer 103 and the hole transport layer 104 are respectively formed by laminating and mixing one kind or two or more kinds of hole injection/transport material(s), or by a mixture of the hole injection/transport material(s) and a polymer binder. Alternatively, the layers may be formed by adding an inorganic salt such as iron (III) chloride to the hole injection/transport material.

The hole injection/transport substance needs to efficiently inject/transport the holes from the positive electrode between the electrodes to which an electric field has been provided, and it is desirable that the hole injection efficiency is high and the injected holes are efficiently transported. For this purpose, a substance having a small ionization potential, a high hole mobility and excellent stability, in which impurities that become traps are difficult to generate during the production and use of the substance, is preferable.

As the material for forming the hole injection layer 103 and the hole transport layer 104, optional one can be used by selecting from compounds that have been conventionally used as charge transport materials for holes in photoconductor materials, p-type semiconductor, and known compounds that are used in hole injection layers and hole transport layers of organic electroluminescent devices. Specific examples thereof are carbazole derivatives (N-phenyl carbazole, polyvinyl carbazole and the like), biscarbazole derivatives such as bis(N-arylcarbazole) or bis(N-alkyl carbazole), triarylamine derivatives (polymers having an aromatic tertiary amino in the main chain or side chain, triphenylamine derivatives such as 1,1-bis(4-di-p-tolylaminophenyl)cyclohexane, N,N'-diphenyl-N,N'-di(3-methylphenyl)-4,4'-diaminobiphenyl, N,N'-diphenyl-N,N'-dinaphthyl-4,4'-diaminobiphenyl (hereinafter abbreviated as NPD), N,N'-diphenyl-N,N'-di(3-methylphenyl)-4,4'-diphenyl-1,1'-di amine, N,N'-dinaphthyl-N,N'-diphenyl-4,4'-diphenyl-1,1'-diamine and 4,4',4"-tris(3-methylphenyl(phenyl)amino) triphenylamine, starburst amine derivatives and the like), stilbene derivatives, phthalocyanine derivatives (metal-free, copper phthalocyanine and the like), heterocycle compounds such as pyrazoline derivatives, hydrazone-based compounds, benzofuran derivatives and thiophene derivatives, oxadiazole derivatives and porphyrin derivatives, polysilanes and the like. As polymer-based compounds, polycarbonates having the above-mentioned monomers on the side chains, styrene derivatives, polyvinyl carbazole and polysilanes and the like are preferable, but are not especially limited as long as they are compounds capable of forming a thin film required for the preparation of a luminescent device, capable of injecting holes from the anode and capable of transporting holes.

Furthermore, it is also known that the electroconductivity of an organic semiconductor is strongly affected by the doping thereof. Such organic semiconductor matrix substance is constituted by a compound having fine electron-donating property or a compound having fine electron-accepting property. For doping of an electron-donating substance, strong electron receptors such as tetracyanoquinonedimethane (TCNQ) or 2,3,5,6-tetrafluorotetracyano-1,4-benzoquinonedimethane (F4TCNQ) are known (for example, see the document "M. Pfeiffer, A. Beyer, T. Fritz, K. Leo, Appl. Phys. Lett., 73 (22), 3202-3204 (1998)" and the document "J. Blochwitz, M. Pheiffer, T. Fritz, K. Leo, Appl. Phys. Lett., 73 (6), 729-731 (1998)"). These generate so-called holes by an electron transfer process in an electron-donating type base substance (hole transport substance). The conductivity of the base substance varies quite significantly depending on the number and mobility of the holes. As the matrix substances having hole transport property, for example, benzidine derivatives (TPD and the like) or starburst amine derivatives (TDATA and the like), or specific metal phthalocyanines (especially, zinc phthalocyanine ZnPc and the like) are known (JP 2005-167175 A).

<Luminescent Layer in Organic Electroluminescent Device>

The luminescent layer 105 emits light by recombining the holes that have been injected from the anode 102 and the electrons that have been injected from the cathode 108 between the electrodes to which an electric field has been provided. The material for forming the luminescent layer 105 may be a compound that emits light by being excited by the recombination of holes and electrons (luminescent compound), and is preferably a compound that can form a stable thin film shape and show strong luminescence (fluorescence and/or phosphorescence) efficiency in a solid state.

The luminescent layer may be formed of a single layer or plural layers, each of which is formed of a luminescent material (a host material, a dopant material), and this may be either a mixture of a host material and a dopant material or a host material alone. Namely, in each layer of the luminescent layer, only the host material or dopant material may emit light, or both of the host material and dopant material may emit light. The host material and dopant material each may be either one kind or a combination of plural kinds. The dopant material may be contained either in the entirety or a part of the host material. The use amount of the dopant differs depends on the dopant, and may be determined according to the property of the dopant. The rough standard of the use amount of the dopant is preferably 0.001 to 50% by weight, more preferably 0.1 to 10% by weight, further preferably 1 to 5% by weight of the entirety of the luminescent material. As the doping process, the dopant material can be formed by a process for co-deposition with the host material, or may be mixed with the host material in advance and simultaneously deposited.

Although the host material is not especially limited, condensed ring derivatives such as anthracene and pyrene that have been known as luminescent bodies since before, metal-chelated oxinoid compounds including tris(8-quinolinolato)aluminum, bisstyryl derivatives such as bisstyrylanthracene derivatives and distyrylbenzene derivatives, tetraphenylbutadiene derivatives, coumarin derivatives, oxadiazole derivatives, pyrrolopyridine derivatives, perinone derivatives, cyclopentadiene derivatives, thiadiazolopyridine derivatives, pyrrolopyrrole derivatives, and polymer-based host materials such as polyphenylenevinylene derivatives, polyparaphenylene derivatives and polythiophene derivatives are preferably used.

In addition, the host material can be suitably selected from the compounds described in Chemical Industry, June 2004, page 13, and the reference documents cited therein, and the like, and used.

The use amount of the host material is preferably 50 to 99.999% by weight, more preferably 80 to 99.95% by weight, further preferably 90 to 99.9% by weight of the entirety of the luminescent material.

Furthermore, as the dopant material, the benzofluorene compound of the above-mentioned general formula (1) can be used, and it is especially preferable to use the compounds represented by the above-mentioned formula (1-1) to formula (1-85). The use amount of the benzofluorene compound represented by the above-mentioned general formula (1) as the dopant material is preferably 0.001 to 50% by weight of the entirety of the luminescent material, more preferably 0.05 to 20% by weight, further preferably 0.1 to 10% by weight. As the doping process, formation can be conducted by a process of co-deposition with the host material, or the deposition may be simultaneously conducted after mixing with the host material in advance.

Furthermore, other dopant materials can be simultaneously used. The other dopant materials are not especially limited, and already-known compounds can be used, and can be selected from various materials according to the desired color of luminescence. Specific examples include condensed ring derivatives such as phenanthrene, anthracene, pyrene, tetracene, pentacene, perylene, naphthopyrene, dibenzopyrene and rubrene, benzoxazole derivatives, benzothiazole derivatives, benzimidazole derivatives, benzotriazole derivatives, oxazole derivatives, oxadiazole derivatives, thiazole derivatives, imidazole derivatives, thiadiazole derivatives, triazole derivatives, pyrazoline derivatives, stilbene derivatives, thiophene derivatives, tetraphenylbutadiene derivatives, cyclopentadiene derivatives, bisstyryl derivatives such as bisstyrylanthracene derivatives and distyrylbenzene derivatives (JP 1-245087 A), bisstyrylarylene derivatives (JP 2-247278 A), diazaindacene derivatives, furan derivatives, benzofuran derivatives, isobenzofuran derivatives such as phenylisobenzofuran, dimesitylisobenzofuran, di(2-methylphenyl)isobenzofuran, di(2-trifluoromethylphenyl)isobenzofuran and phenylisobenzofuran, dibenzofuran derivatives, coumarin derivatives such as 7-dialkylaminocoumarin derivatives, 7-piperidinocoumarin derivatives, 7-hydroxycoumarin derivatives, 7-methoxycoumarinderivatives, 7-acetoxycoumarin derivatives, 3-benzothiazolylcoumarin derivatives, 3-benzimidazolylcoumarin derivatives and 3-benzoxazolylcoumarin derivatives, dicyanomethylenepyran derivatives, dicyanomethylenethiopyran derivatives, polymethine derivatives, cyanine derivatives, oxobenzoanthracene derivatives, xanthene derivatives, rhodamine derivatives, fluorescein derivatives, pyrylium derivatives, carbostyryl derivatives, acridine derivatives, oxazin derivatives, phenyleneoxide derivatives, quinacridone derivatives, quinazoline derivatives, pyrrolopyridine derivatives, furopyridine derivatives, 1,2,5-thiadiazolopyrene derivatives, pyrromethene derivatives, perinone derivatives, pyrrolopyrrole derivatives, squarylium derivatives, violanthrone derivatives, phenazine derivatives, acridone derivatives and deazaflavin derivatives, and the like.

The dopant materials will be exemplified for every colored light. Examples of blue to blue green dopant materials include aromatic hydrocarbon compounds such as naphthalene, anthracene, phenanthrene, pyrene, triphenylene, perylene, fluorene and indene and derivatives thereof, aromatic heterocycle compounds such as furan, pyrrole, thiophene, silole, 9-silafluorene, 9,9'-spirobisilafluorene, benzothiophene, benzofuran, indole, dibenzothiophene, dibenzofuran, imidazopyridine, phenanthroline, pyrazine, naphthylidine, quinoxaline, pyrrolopyridine and thioxanthene and derivatives thereof, distyrylbenzene derivatives, tetraphenylbutadiene derivatives, stilbene derivatives, aldazine derivatives, coumarin derivatives, azole derivatives such as imidazole, thiazole, thiadiazole, carbazole, oxazole, oxadiazole and triazole and metal complexes thereof, and aromatic amine derivatives represented by N,N'-diphenyl-N,N'-di(3-methylphenyl)-4,4'-diphenyl-1,1'-di amine, and the like.

Furthermore, examples of green to yellow dopant materials include coumarin derivatives, phthalimide derivatives, naphthalimide derivatives, perinone derivatives, pyrrolopyrrole derivatives, cyclopentadiene derivatives, acridone derivatives, quinacridone derivatives and naphthacene derivatives such as rubrene, and the like, and also include, as preferable examples, compounds obtained by introducing a substituent that enables red-shifting such as an aryl, a heteroaryl, an arylvinyl, amino and cyano into the compounds exemplified as the above-mentioned blue to blue green dopant materials.

Furthermore, examples of orange to red dopant materials include naphthalimide derivatives such as bis(diisopropylphenyl)perylene tetracarboxylic acid imide, perinone derivatives, rare earth complexes including acetylacetone or benzoylacetone and phenanthroline or the like as ligands such as Eu complex, 4-(dicyanomethylene)-2-methyl-6-(p-dimethylaminostyryl)-4H-pyran and analogues thereof, metalphthalocyanine derivatives such as magnesium phthalocyanine and aluminum chlorophthalocyanine, rhodamine compounds, deazaflavin derivatives, coumarin derivatives, quinacridone derivatives, phenoxazine derivatives, oxazin derivatives, quinazoline derivatives, pyrrolopyridine derivatives, squarylium derivatives, violanthrone derivatives, phenazine derivatives, phenoxazone derivatives and thiadiazolopyrene derivatives, and the like, and also include, as preferable examples, compounds obtained by introducing a substituent that enables red-shifting such as an aryl, a heteroaryl, an arylvinyl, amino and cyano into the compounds exemplified as the above-mentioned blue to blue green and green to yellow dopant materials. In addition, phosphorescent metal complexes containing iridium or platinum as a center metal represented by tris(2-phenylpyridine)iridium(III) are also exemplified as preferable examples.

As the dopant material suitable for the material for a luminescent layer of the present invention, among the dopant materials mentioned above, the benzofluorene compound represented by the above-mentioned general formula (1) is optimal, and as the dopant materials that can be simultaneously used, perylene derivatives, borane derivatives, amine-containing styryl derivatives, aromatic amine derivatives, coumarin derivatives, pyran derivatives, iridium complexes or platinum complexes are preferable.

Examples of the perylene derivatives include
3,10-bis(2,6-dimethylphenyl)perylene,
3,10-bis(2,4,6-trimethylphenyl)perylene,
3,10-diphenylperylene, 3,4-diphenylperylene,
2,5,8,11-tetra-t-butylperylene,
3,4,9,10-tetraphenylperylene,
3-(1'-pyrenyl)-8,11-di(t-butyl)perylene,
3-(9'-anthryl)-8,11-di(t-butyl)perylene,
3,3'-bis(8,11-di(t-butyl) perylenyl) and the like.

Alternatively, the perylene derivatives described in JP 11-97178 A, JP 2000-133457 A, JP 2000-26324 A, JP 2001-267079 A, JP 2001-267078 A, JP 2001-267076 A, JP 2000-34234 A, JP 2001-267075 A and JP 2001-217077 A, and the like may also be used.

Examples of the boran derivatives include
1,8-diphenyl-10-(dimesitylboryl)anthracene,
9-phenyl-10-(dimesitylboryl)anthracene,
4-(9'-anthryl)dimesitylborylnaphthalene,
4-(10'-phenyl-9'-anthryl)dimesitylborylnaphthalene,
9-(dimesitylboryl)anthracene,
9-(4'-biphenylyl)-10-(dimesitylboryl)anthracene,
9-(4'-(N-carbazolyl)phenyl)-10-(dimesitylboryl)anthracene and the like.

Alternatively, the borane derivatives described in WO 2000/40586 A and the like may also be used.

Examples of the amine-containing styryl derivatives include
N,N,N',N'-tetra(4-biphenylyl)-4,4'-diaminostilbene,
N,N,N',N'-tetra(1-naphthyl)-4,4'-diaminostilbene,
N,N,N',N'-tetra(2-naphthyl)-4,4'-diaminostilbene,
N,N'-di(2-naphthyl)-N,N'-diphenyl-4,4'-diaminostilbene,
N,N'-di(9-phenanthryl)-N,N'-diphenyl-4,4'-diaminostilbene,
4,4'-bis[4''-bis(diphenylamino)styryl]-biphenyl,
1,4-bis[4'-bis(diphenylamino)styryl]-benzene,
2,7-bis[4'-bis(diphenylamino)styryl]-9,9-dimethylfluorene,
4,4'-bis(9-ethyl-3-carbazovinylene)-biphenyl,
4,4'-bis(9-phenyl-3-carbazovinylene)-biphenyl and the like.
Alternatively, the amine-containing styryl derivatives described in JP 2003-347056 A and JP 2001-307884 A, and the like may also be used.

Examples of the aromatic amine derivatives include
N,N,N,N-tetraphenylanthracene-9,10-diamine,
9,10-bis(4-diphenylamino-phenyl)anthracene,
9,10-bis(4-di(1-naphthylamino)phenyl)anthracene,
9,10-bis(4-di(2-naphthylamino)phenyl)anthracene,
10-di-p-tolylamino-9-(4-di-p-tolylamino-1-naphthyl)anthracene,
10-diphenylamino-9-(4-diphenylamino-1-naphthyl)anthracene, 10-diphenylamino-9-(6-diphenylamino-2-naphthyl)anthracene,
[4-(4-diphenylamino-phenyl)naphthalen-1-yl]-diphenylamine,
[6-(4-diphenylamino-phenyl)naphthalen-2-yl]-diphenylamine,
4,4'-bis[4-diphenylaminonaphthalen-1-yl]biphenyl,
4,4'-bis[6-diphenylaminonaphthalen-2-yl]biphenyl,
4,4"-bis[4-diphenylaminonaphthalen-1-yl]-p-terphenyl,
4,4"-bis[6-diphenylaminonaphthalen-2-yl]-p-terphenyl and the like.

Alternatively, the aromatic amine derivatives described in JP 2006-156888 A and the like may also be used.

Examples of the coumarin derivatives include coumarin-6, coumarin-334 and the like.

Alternatively, the coumarin derivatives described in JP 2004-43646 A, JP 2001-76876 A and JP 6-298758 A, and the like may also be used.

Examples of the pyran derivatives include DOM, DCJTB and the like mentioned below.

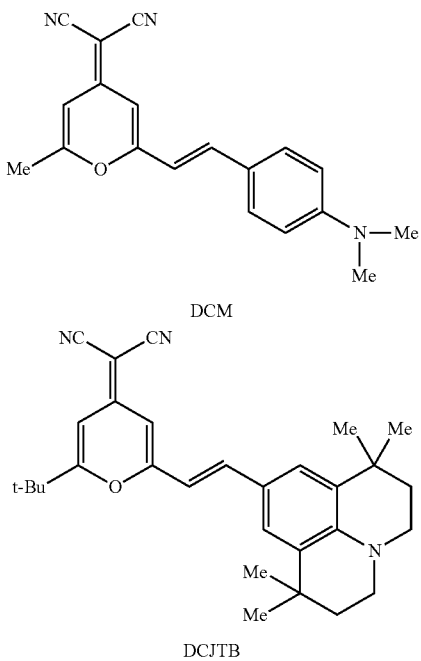

DCM

DCJTB

Alternatively, the pyran derivatives described in JP 2005-126399A, JP2005-097283 A, JP2002-234892 A, JP2001-220577 A, JP 2001-081090 A and JP 2001-052869 A, and the like may also be used.

Examples of the iridium complexes include Ir(ppy)₃ mentioned below, and the like.

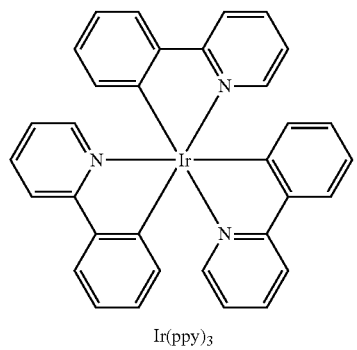

Ir(ppy)₃

Alternatively, the iridium complexes described in JP 2006-089398A, JP2006-080419A, JP2005-298483A, JP 2005-097263 A and JP 2004-111379 A, and the like may also be used.

Examples of the platinum complexes include PtOEP mentioned below, and the like.

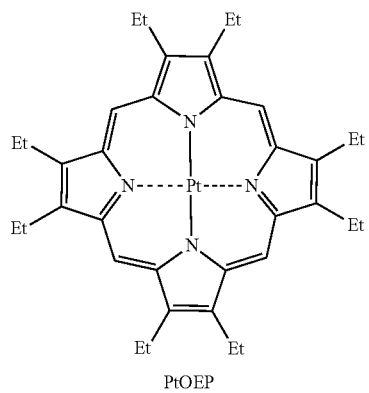

PtOEP

Alternatively, the platinum complexes described in JP 2006-190718A, JP2006-128634 A, JP2006-093542 A, JP 2004-335122 A, and JP 2004-331508 A, and the like may also be used.

Other dopants can be suitably selected from the compounds described in Chemical Industry June 2004, page 13 and the reference documents cited therein, and the like, and used.

<Electron Injection Layer and Electron Transport Layer in Organic Electroluminescent Device>

The electron injection layer 107 plays a role in efficiently injecting the electrons that have been transferred from the cathode 108 into the luminescent layer 105 or the electron transport layer 106. The electron transport layer 106 plays a role in efficiently transporting the electrons that have been injected from the cathode 108 or the electrons that have been injected from the cathode 108 through the electron injection layer 107 to the luminescent layer 105. The electron transport layer 106 and the electron injection layer 107 are respectively formed by laminating and mixing one kind or two or more kinds of electron transport/injection material(s), or by a mixture of the electron transport/injection material(s) and a polymer binder.

The electron injection/transport layer is a layer that controls the injection of electrons from the cathode and further transport of the electrons, and it is desirable that the layer has a high electron injection efficiency and efficiently transports the injected electrons. For that purposes, a substance that has high electron affinity and a high electron transfer degree and excellent stability, in which impurities that become traps are difficult to be generated during the production and use, is preferable. However, in the case when the balance of transportation of holes and electrons is taken into consideration, in the case when the substance mainly plays a role that enables efficient blocking of the flowing of the holes from the anode to the cathode side without recombination, the substance has an equivalent effect of improving luminescence efficiency to that of a material having high electron transportability, even the electron transportability is not so high. Therefore, the electron injection/transport layer in this exemplary embodiment may also include a function of a layer capable of efficiently blocking the transfer of holes.

The materials used for the electron transport layer and the electron injection layer can be arbitrary selected from compounds that have been conventionally used as electron transfer compounds in photoconductor materials, and known compounds that are used in electron injection layers and electron transport layers of organic electroluminescent devices, and used.

Specifically, pyridine derivatives, naphthalene derivatives, anthracene derivatives, phenanthroline derivatives, perinone derivatives, coumarin derivatives, naphthalimide derivatives, anthraquinone derivatives, diphenoquinone derivatives, diphenylquinone derivatives, perylene derivatives, thiophene derivatives, thiadiazole derivatives, quinoxaline derivatives, polymers of quinoxaline derivatives, benzazole compounds, pyrrazole derivatives, perfluorinated phenylene derivatives, triazine derivatives, pyrazine derivatives, imidazopyridine derivatives, boran derivatives, benzoxazole derivatives, benzothiazole derivatives, quinoline derivatives, aldazine derivatives, carbazole derivatives, indole derivatives, phosphorus oxide derivatives, bisstyryl derivatives and the like are exemplified. Furthermore, oxadiazole derivatives (1,3-bis[(4-t-butylphenyl)-1,3,4-oxadiazolyl]phenylene and the like), triazole derivatives (N-naphthyl-2,5-diphenyl-1,3,4-triazole and the like), benzoquinoline derivatives (2,2'-bis(benzo[h]quinolin-2-yl)-9,9'-spirobifluorene and the like), benzimidazole derivatives (tris(N-phenylbenzimidazol-2-yl)benzene and the like), bipyridine derivatives, terpyridine derivatives (1,3-bis(4'-(2,2':6'2"-terpyridinyl))benzene and the like), naphthylidine derivatives (bis(1-naphthyl)-4-(1,8-naphthylidin-2-yl) phenylphosphine oxide and the like) and the like are exemplified. These materials may be used alone, or may be used by mixing with different materials.

Altenatively, metal complexes having electron-accepting nitrogen can also be used, and examples include quinolinol-based metal complexes, hydroxyazole complexes such as hydroxyphenyloxazole complexes, azomethine complexes, tropolon metal complexes, flavonol metal complexes and benzoquinoline metal complexes, and the like. These materials may be used alone, or may be used by mixing with different materials.

Among the above-mentioned materials, quinolinol-based metal complexes, pyridine derivatives, phenanthroline derivatives, boran derivatives or benzimidazole derivatives are preferable.

The quinolinol-based metal complexes are compound represented by the following formula (E-1).

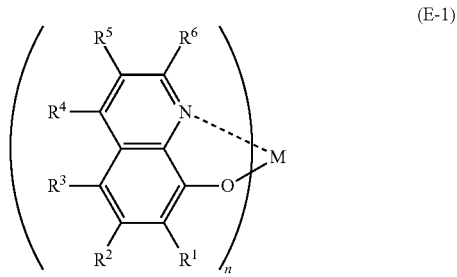

(E-1)

In the formula, $R^1$ to $R^6$ are each hydrogen or a substituent, M is Li, Al, Ga, Be or Zn, and n is an integer of 1 to 3.

Specific examples of the quinolinol-based metal complexes include
8-quinolinollithium,
tris(8-quinolinolate)aluminum,
tris(4-methyl-8-quinolinolate)aluminum,
tris(5-methyl-8-quinolinolate)aluminum,
tris(3,4-dimethyl-8-quinolinolate)aluminum,
tris(4,5-dimethyl-8-quinolinolate)aluminum,
tris(4,6-dimethyl-8-quinolinolate)aluminum,
bis(2-methyl-8-quinolinolate)(phenolate)aluminum,
bis(2-methyl-8-quinolinolate)(2-methylphenolate)aluminum,
bis(2-methyl-8-quinolinolate)(3-methylphenolate)aluminum,
bis(2-methyl-8-quinolinolate)(4-methylphenolate)aluminum,
bis(2-methyl-8-quinolinolate)(2-phenylphenolate)aluminum,
bis(2-methyl-8-quinolinolate)(3-phenylphenolate)aluminum,
bis(2-methyl-8-quinolinolate)(4-phenylphenolate)aluminum,
bis(2-methyl-8-quinolinolate)(2,3-dimethylphenolate)aluminum,
bis(2-methyl-8-quinolinolate)(2,6-dimethylphenolate)aluminum,
bis(2-methyl-8-quinolinolate)(3,4-dimethylphenolate)aluminum,
bis(2-methyl-8-quinolinolate)(3,5-dimethylphenolate)aluminum,
bis(2-methyl-8-quinolinolate)(3,5-di-t-butylphenolate)aluminum,
bis(2-methyl-8-quinolinolate)(2,6-diphenylphenolate)aluminum,
bis(2-methyl-8-quinolinolate)(2,4,6-triphenylphenolate)aluminum,
bis(2-methyl-8-quinolinolate)(2,4,6-trimethylphenolate)aluminum,
bis(2-methyl-8-quinolinolate)(2,4,5,6-tetramethylphenolate) aluminum,
bis(2-methyl-8-quinolinolate)(1-naphtholate)aluminum,
bis(2-methyl-8-quinolinolate)(2-naphtholate)aluminum,
bis(2,4-dimethyl-8-quinolinolate)(2-phenylphenolate)aluminum,
bis(2,4-dimethyl-8-quinolinolate)(3-phenylphenolate)aluminum,
bis(2,4-dimethyl-8-quinolinolate)(4-phenylphenolate)aluminum,
bis(2,4-dimethyl-8-quinolinolate)(3,5-dimethylphenolate) aluminum,
bis(2,4-dimethyl-8-quinolinolate)(3,5-di-t-butylphenolate) aluminum,
bis(2-methyl-8-quinolinolate)aluminum-1-oxo-bis(2-methyl-8-quinolinolate)aluminum,
bis(2,4-dimethyl-8-quinolinolate)aluminum-µ-oxo-bis(2,4-dim ethyl-8-quinolinolate)aluminum,
bis(2-methyl-4-ethyl-8-quinolinolate)aluminum-µ-oxo-bis (2-m ethyl-4-ethyl-8-quinolinolate)aluminum,
bis(2-methyl-4-methoxy-8-quinolinolate)aluminum-µ-oxo-bis(2-methyl-4-methoxy-8-quinolinolate)aluminum,
bis(2-methyl-5-cyano-8-quinolinolate)aluminum-t-oxo-bis (2-m ethyl-5-cyano-8-quinolinolate)aluminum,
bis(2-methyl-5-trifluoromethyl-8-quinolinolate)aluminum-µ-oxo-bis(2-methyl-5-trifluoromethyl-8-quinolinolate) aluminum,
bis(10-hydroxybenzo[h]quinoline)beryllium and the like.

The pyridine derivatives are compounds represented by the following formula (E-2).

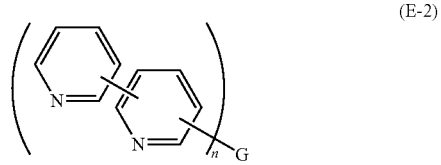

(E-2)

In the formula, G represents a simple bond or a linking group with a valency of n, and n is an integer of 2 to 8. Furthermore, the carbon atoms that are not used for the bonding of pyridine-pyridine or pyridine-G may be substituted.

Examples of G in the formula (E-2) include those having the following structural formulas. The Rs in the following structural formulas are each independently hydrogen, methyl, ethyl, isopropyl, cyclohexyl, phenyl, 1-naphthyl, 2-naphthyl, biphenylyl or terphenylyl.
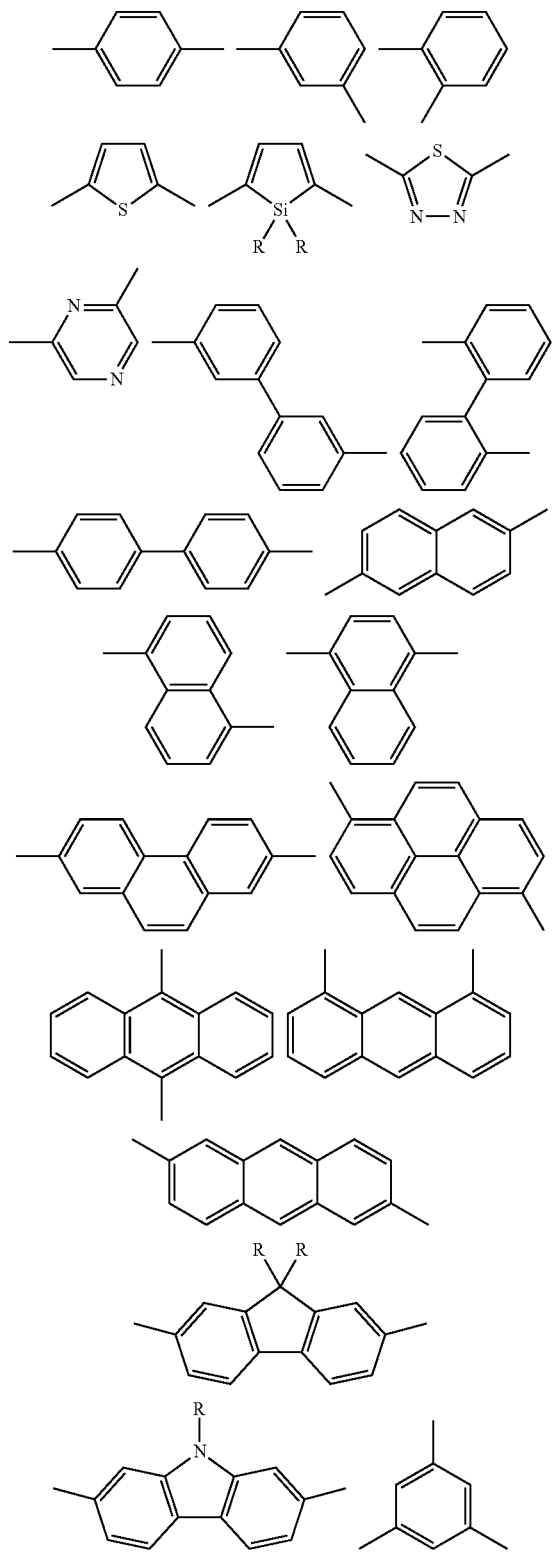
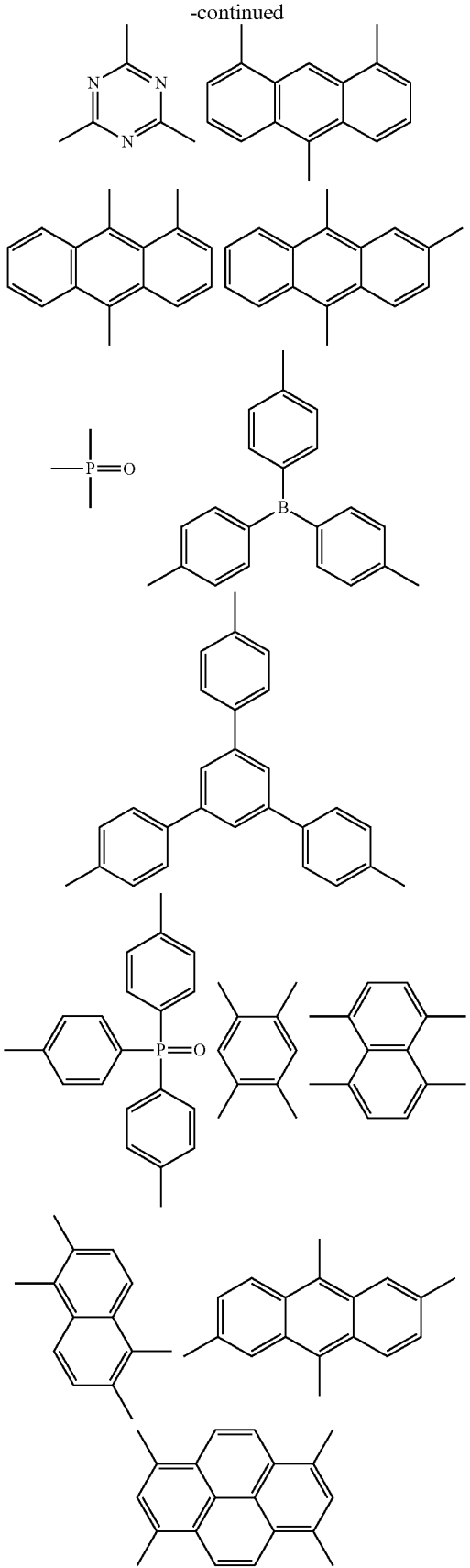

Specific examples of the pyridine derivatives are
2,5-bis(2,2'-bipyridin-6-yl)-1,1-dimethyl-3,4-diphenylsilole,
2,5-bis(2,2'-bipyridin-6-yl)-1,1-dimethyl-3,4-dimesitylsilole,
2,5-bis(2,2'-bipyridin-5-yl)-1,1-dimethyl-3,4-diphenylsilole,
2,5-bis(2,2'-bipyridin-5-yl)-1,1-dimethyl-3,4-dimesitylsilole,
9,10-di(2,2'-bipyridin-6-yl)anthracene,
9,10-di(2,2'-bipyridin-5-yl)anthracene,
9,10-di(2,3'-bipyridin-6-yl)anthracene,
9,10-di(2,3'-bipyridin-5-yl)anthracene,
9,10-di(2,3'-bipyridin-6-yl)-2-phenylanthracene,
9,10-di(2,3'-bipyridin-5-yl)-2-phenylanthracene,
9,10-di(2,2'-bipyridin-6-yl)-2-phenylanthracene,
9,10-di(2,2'-bipyridin-5-yl)-2-phenylanthracene,
9,10-di(2,4'-bipyridin-6-yl)-2-phenylanthracene,
9,10-di(2,4'-bipyridin-5-yl)-2-phenylanthracene,
9,10-di(3,4'-bipyridin-6-yl)-2-phenylanthracene,
9,10-di(3,4'-bipyridin-5-yl)-2-phenylanthracene, 3,4-diphenyl-2,5-di(2,2'-bipyridin-6-yl)thiophene,
3,4-diphenyl-2,5-di(2,3'-bipyridin-5-yl)thiophene,
6'6"-di(2-pyridyl)2,2':4',4":2",2'"-quaterpyridine and the like.

The phenanthroline derivatives are compounds represented by the following formula (E-3-1) or (E-3-2).

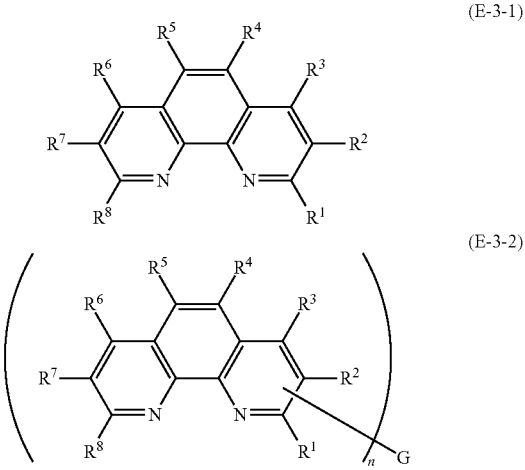

(E-3-1)

(E-3-2)

In the formulas, $R^1$ to $R^8$ are each hydrogen or a substituent, where in the adjacent groups may bind to each other to form a condensed ring, G represents a simple bond or a linking group with a valency of n, and n is an integer of 2 to 8. Furthermore, examples of G in the formula (E-3-2) include those similar to those explained in the column of the bipyridine derivatives.

Specific examples of the phenanthroline derivatives include
4,7-diphenyl-1,10-phenanthroline,
2,9-dimethyl-4,7-diphenyl-1,10-phenanthroline,
9,10-di(1,10-phenanthrolin-2-yl)anthracene,
2,6-di(1,10-phenanthrolin-5-yl)pyridine,
1,3,5-tri(1,10-phenanthrolin-5-yl)benzene,
9,9'-difluoro-bis(1,10-phenanthrolin-5-yl),
bathocuproine,
1,3-bis(2-phenyl-1,10-phenanthrolin-9-yl)benzene and the like.

Especially, the case when a phenanthroline derivative is used in the electron transport layer and the electron injection layer will be explained. In order to obtain stable luminescent over a longtime, a material that is excellent in thermal stability and thin film formability is desired, and among phenanthroline derivatives, those having substituents in which the substituents themselves have three-dimensional steric structures or those having three-dimensional steric structures by the steric repulsion with the phenanthroline backbone or the adjacent substituents, or those formed by linking plural phenanthroline backbones are preferable. Furthermore, in the case when plural phenanthroline backbones are connected, compounds containing conjugate bonds, substituted or unsubstituted aromatic hydrocarbons or substituted or unsubstituted aromatic heterocycles in the linked units are more preferable.

The boran derivatives are compounds represented by the following formula (E-4), and the details thereof are disclosed in JP 2007-27587 A.

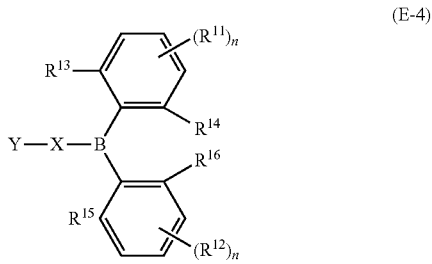

(E-4)

In the formula, $R^{11}$ and $R^{12}$ are each independently at least one of hydrogen, an alkyl, an optionally substituted aryl, a substituted silyl, an optionally substituted nitrogen-containing heterocycle or cyano, $R^{13}$ to $R^{16}$ are each independently an optionally substituted alkyl or an optionally substituted aryl, X is an optionally substituted arylene, Y is an optionally substituted aryl, substituted boryl or optionally substituted carbazole with a carbon number of 16 or less, and ns are each independently an integer of 0 to 3.

Among the compounds represented by the above-mentioned formula (E-4), compounds represented by the following formula (E-4-1) and compounds represented by the following formulas (E-4-1-1) to (E-4-1-4) are preferable. Specific examples include
9-[4-(4-dimesitylborylnaphthalen-1-yl)phenyl]carbazole,
9-[4-(4-dimesitylborylnaphthalen-1-yl) naphthalen-1-yl]carbazole and the like.

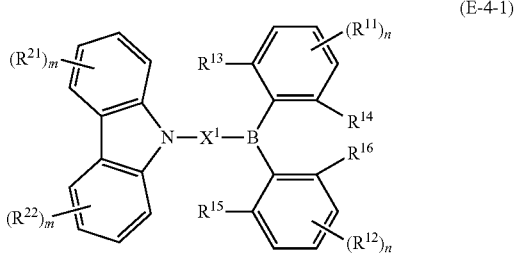

(E-4-1)

In the formula, $R^{11}$ and $R^{12}$ are each independently at least one of hydrogen, an alkyl, an optionally substituted aryl, a substituted silyl, an optionally substituted nitrogen-containing heterocycle or cyano, $R^{13}$ to $R^{16}$ are each independently an optionally substituted alkyl or an optionally substituted aryl, $R^{21}$ and $R^{22}$ are each independently at least one of hydrogen, an alkyl, an optionally substituted aryl, a substituted silyl, an optionally substituted nitrogen-containing heterocycle or cyano, $X^1$ is an optionally substituted arylene with a carbon number of 20 or less, ns are each independently an integer of 0 to 3, and ms are each independently an integer of 0 to 4.

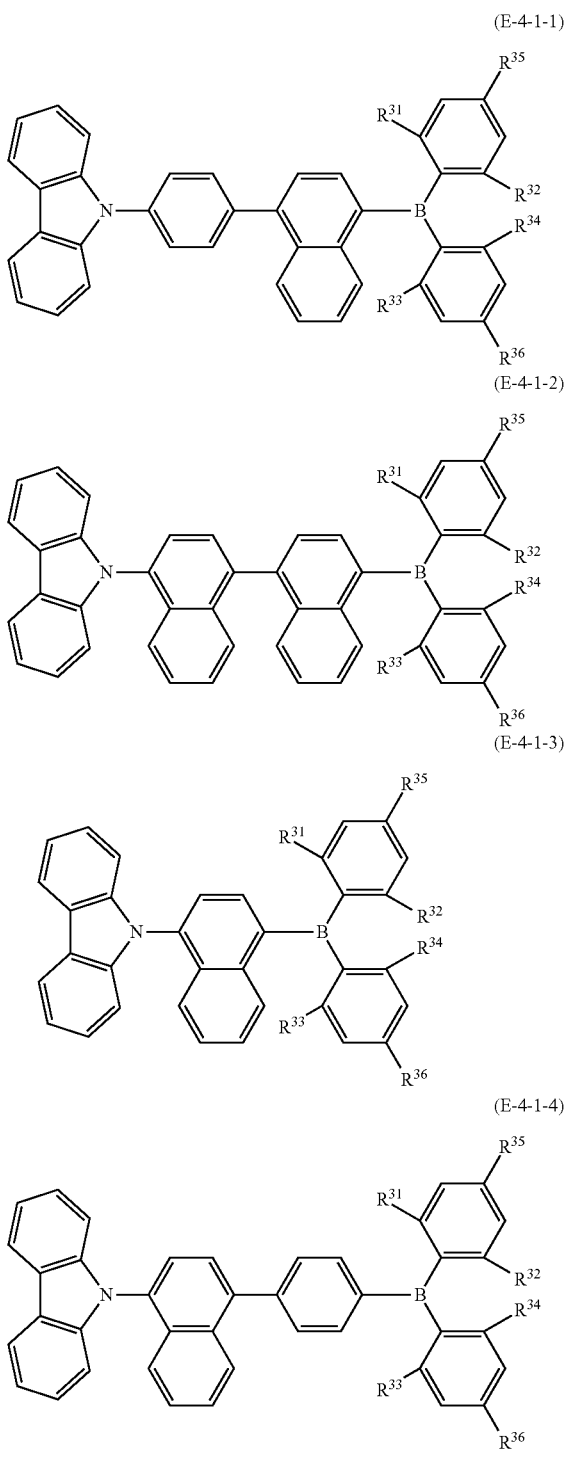

In each formula, $R^{31}$ to $R^{34}$ are each independently any of methyl, isopropyl or phenyl, and $R^{35}$ and $R^{36}$ are each independently any of hydrogen, methyl, isopropyl or phenyl.

Among the compounds represented by the above-mentioned formula (E-4), the compounds represented by the following formula (E-4-2) and the compounds represented by the following formula (E-4-2-1) are preferable.

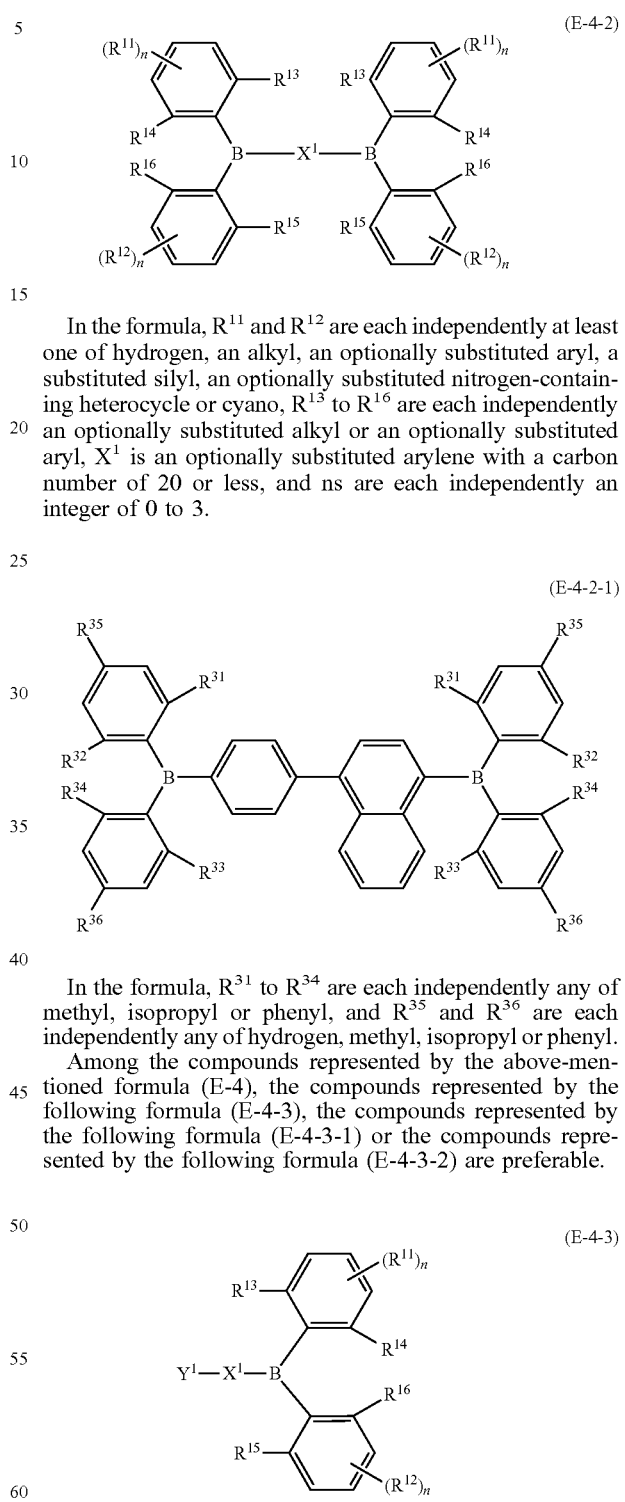

In the formula, $R^{11}$ and $R^{12}$ are each independently at least one of hydrogen, an alkyl, an optionally substituted aryl, a substituted silyl, an optionally substituted nitrogen-containing heterocycle or cyano, $R^{13}$ to $R^{16}$ are each independently an optionally substituted alkyl or an optionally substituted aryl, $X^1$ is an optionally substituted arylene with a carbon number of 20 or less, and ns are each independently an integer of 0 to 3.

In the formula, $R^{31}$ to $R^{34}$ are each independently any of methyl, isopropyl or phenyl, and $R^{35}$ and $R^{36}$ are each independently any of hydrogen, methyl, isopropyl or phenyl.

Among the compounds represented by the above-mentioned formula (E-4), the compounds represented by the following formula (E-4-3), the compounds represented by the following formula (E-4-3-1) or the compounds represented by the following formula (E-4-3-2) are preferable.

In the formula, $R^{11}$ and $R^{12}$ are each independently at least one of hydrogen, an alkyl, an optionally substituted aryl, a substituted silyl, an optionally substituted nitrogen-containing heterocycle or cyano, $R^{13}$ to $R^{16}$ are each independently an optionally substituted alkyl or an optionally substituted aryl, $X^1$ is an optionally substituted arylene with a carbon number of 10 or less, $Y^1$ is an optionally substituted aryl with a carbon number of 14 or less, and ns are each independently an integer of 0 to 3.

(E-4-3-1)

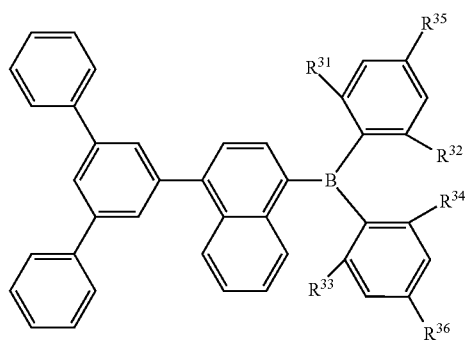

(E-4-3-2)

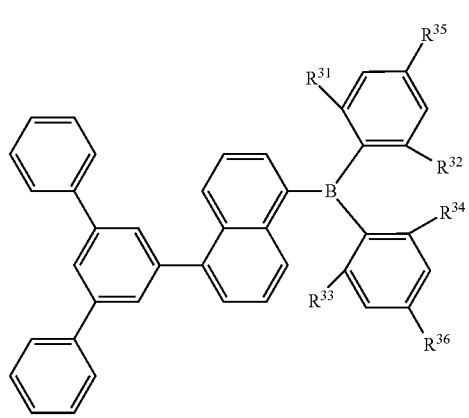

In each formula, $R^{31}$ to $R^{34}$ are each independently any of methyl, isopropyl or phenyl, and $R^{35}$ and $R^{36}$ are each independently any of hydrogen, methyl, isopropyl or phenyl.

The benzimidazole derivatives are compounds represented by the following formula (E-5).

(E-5)

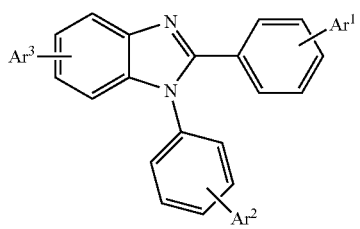

In the formula, $Ar^1$ to $Ar^3$ are each independently hydrogen or an optionally substituted aryl with a carbon number of 6 to 30. Especially, the benzimidazole derivatives wherein $Ar^1$ is an optionally substituted anthryl are preferable.

Specific examples of the aryl with a carbon number of 6 to 30 include phenyl, 1-naphthyl, 2-naphthyl, acenaphthylen-1-yl, acenaphthylen-3-yl, acenaphthylen-4-yl, acenaphthylen-5-yl, fluoren-1-yl, fluoren-2-yl, fluoren-3-yl, fluoren-4-yl, fluoren-9-yl, phenalen-1-yl, phenalen-2-yl, 1-phenanthryl, 2-phenanthryl, 3-phenanthryl, 4-phenanthryl, 9-phenanthryl, 1-anthryl, 2-anthryl, 9-anthryl, fluoranthen-1-yl, fluoranthen-2-yl, fluoranthen-3-yl, fluoranthen-7-yl, fluoranthen-8-yl, triphenylen-1-yl, triphenylen-2-yl, pyren-1-yl, pyren-2-yl, pyren-4-yl, chrysen-1-yl, chrysen-2-yl, chrysen-3-yl, chrysen-4-yl, chrysen-5-yl, chrysen-6-yl, naphthacen-1-yl, naphthacen-2-yl, naphthacen-5-yl, perylen-1-yl, perylen-2-yl, perylen-3-yl, pentacen-1-yl, pentacen-2-yl, pentacen-5-yl and pentacen-6-yl.

Specific examples of the benzimidazole derivatives include
1-phenyl-2-(4-(10-phenylanthracen-9-yl)phenyl)-1H-benzo[d]imidazole,
2-(4-(10-(naphthalen-2-yl)anthracen-9-yl)phenyl)-1-phenyl-1H-benzo[d]imidazole,
2-(3-(10-(naphthalen-2-yl)anthracen-9-yl)phenyl)-1-phenyl-1H-benzo[d]imidazole,
5-(10-(naphthalen-2-yl)anthracen-9-yl)-1,2-diphenyl-1H-benz[d]imidazole,
1-(4-(10-(naphthalen-2-yl)anthracen-9-yl)phenyl)-2-phenyl-1H-benzo[d]imidazole,
2-(4-(9,10-di(naphthalen-2-yl)anthracen-2-yl)phenyl)-1-phenyl-1H-benzo[d]imidazole,
1-(4-(9,10-di(naphthalen-2-yl)anthracen-2-yl)phenyl)-2-phenyl-1H-benzo[d]imidazole, and
5-(9,10-di(naphthalen-2-yl)anthracen-2-yl)-1,2-diphenyl-1H-benzo[d]imidazole.

The electron transport layer or the electron injection layer may further contain a substance that can reduce the material that forms the electron transport layer or electron injection layer. As this reductive substance, various substances are used as long as they have certain reductivity, and at least one selected from, for example, alkali metals, alkaline earth metals, rare earth metals, oxides of alkali metals, halides of alkali metals, oxides of alkaline earth metals, halides of alkaline earth metals, oxides of rare earth metals, halides of rare earth metals, organic complexes of alkali metals, organic complexes of alkaline earth metals and organic complexes of rare earth metals can be preferably used.

Preferable reductive substances include alkali metals such as Na (work function: 2.36 eV), K (work function: 2.28 eV), Rb (work function: 2.16 eV) or Cs (work function: 1.95 eV), alkaline earth metals such as Ca (work function: 2.9 eV), Sr (work function: 2.0 to 2.5 eV) or Ba (work function: 2.52 eV), and those having a work function of 2.9 eV or less are especially preferable. Among these, more preferable reductive substances are alkali metals K, Rb or Cs, and Rb or Cs is further preferable, and Cs is the most preferable. These alkali metals especially have high reductivity, and by adding these to the material that forms the electron transport layer or electron injection layer in a relatively small amount, the luminance of the luminescent in an organic EL element is improved and the lifetime is extended. Furthermore, as the reductive substance having a work function of 2.9 eV or less, a combination of two or more kinds of these alkali metals is also preferable, and especially, combinations containing Cs such as a combination of Cs and Na, Cs and K, Cs and Rb or Cs and Na and K is preferable. Since the reductive substance contains Cs, the reducibility can be efficiently exerted, and the luminance of the luminescence in an organic EL element is improved and the lifetime is extended by adding to the material that forms the electron transport layer or the electron injection layer.

<Cathode in Organic Electroluminescent Device>

The cathode 108 plays a role in injecting electrons to the luminescent layer 105 through the electron injection layer 107 and the electron transport layer 106.

The material for forming the cathode 108 is not especially limited as long as it is a substance that can efficiently inject the electrons into the organic layer, similar materials to the material that forms the anode 102 can be used. Among these, metals such as tin, indium, calcium, aluminum, silver, copper, nickel, chromium, gold, platinum, iron, zinc, lithium, sodium, potassium, cesium and magnesium or alloys thereof (magnesium-silver alloys, magnesium-indium alloys, aluminum-lithium alloys such as lithium fluoride/ aluminum, and the like) and the like are preferable. In order to increase the electron injection efficiency to improve the element property, lithium, sodium, potassium, cesium, calcium, magnesium or alloys containing these metals having a low work function are effective. However, in many cases, these low work function metals are generally unstable in the air. In order to improve this point, for example, a process using an electrode having high stability by doping an organic layer with a trace amount of lithium, cesium or magnesium is known. As other dopants, inorganic salts such as lithium fluoride, cesium fluoride, lithium oxide and cesium oxide can also be used. However the dopants are not limited to these.

Furthermore, in order to protect the electrodes, preferable examples include laminating metals such as platinum, gold, silver, copper, iron, tin, aluminum and indium or alloys using these metals, inorganic substances such as silica, titania and silicon nitride, polyvinyl alcohol, vinyl chloride, hydrocarbon-based polymer compounds and the like. The processes for preparing these electrodes are not especially limited as long as conduction can be obtained, and include resistance heating, electron ray beam, sputtering, ion plating and coating, and the like.

<Binder that May be Used in Respective Layers>

The above-mentioned materials that are used for the hole injection layer, hole transport layer, luminescent layer, electron transport layer and electron injection layer can form the respective layers by themselves, but can also be used by dispersing in a polymer binder, including solvent-soluble resins such as polyvinyl chloride, polycarbonate, polystyrene, poly(N-vinyl carbazole), polymethyl methacrylate, polybutyl methacrylate, polyester, polysulfone, polyphenylene oxide, polybutadiene, hydrocarbon resins, ketone resins, phenoxy resins, polyamide, ethyl cellulose, vinyl acetate resins, ABS resins and polyurethane resins, curable resins such as phenolic resins, xylene resins, petroleum resins, urea resins, melamine resins, unsaturated polyester resins, alkid resins, epoxy resins and silicone resins.

<Method for Preparing Organic Electroluminescent Device>

The respective layers that constitute the organic electroluminescent device can be formed by forming the materials that should constitute the respective layers into thin films by a process such as a deposition process, resistance heating deposition, electron beam deposition, sputtering, a molecular lamination process, a printing process, a spin coating process or a casting process, a coating process, and the like. The film thickness of each layer formed by this way is not especially limited and can be suitably preset according to the property of the material, but is generally in the range of 2 nm to 5000 nm. The film thickness can be generally measured by a quartz crystal oscillator film thickness meter or the like. In the case when a thin film is formed by using a deposition process, the deposition conditions thereof differ depending on the kind of the material, the intended crystal structure and associated structure of the film, and the like. It is preferable that the deposition conditions are suitably preset generally in the ranges of a boat heating temperature of +50 to +400° C., a vacuum degree of $10^{-6}$ to $10^{-3}$ Pa, a deposition velocity of 0.01 to 50 nm/sec, a substrate temperature of −150 to +300° C., a film thickness of 2 nm to 5 μm.

Next, as an example of the process for preparing the organic electroluminescent device, a process for preparing an organic electroluminescent device formed of an anode/a hole injection layer/a hole transport layer/a luminescent layer formed of a host material and a dopant material/an electron transport layer/an electron injection layer/a cathode will be explained. A thin film of an anode material is formed on a suitable substrate by a deposition process or the like to thereby form an anode, and thin films of a hole injection layer and a hole transport layer are formed on this anode. A host material and a dopant material are co-deposited thereon to form a thin film to thereby give a luminescent layer, and an electron transport layer and an electron injection layer are formed on this luminescent layer, and a thin film formed of a substance for a cathode is further formed by a deposition process or the like to give a cathode, thereby the intended organic electroluminescent device can be obtained. In the preparation of the above-mentioned organic electroluminescent device, it is also possible to reverse the order of preparation to prepare the cathode, electron injection layer, electron transport layer, luminescent layer, hole transport layer, hole injection layer and anode in this order.

In the case when a direct current voltage is applied to the organic electroluminescent device obtained in such way, it is sufficient to apply so that the anode has polarity of + and the cathode has polarity of −, and when a voltage of about 2 to 40 V is applied, luminescence can be observed from the side of the transparent or translucent electrode (the anode or cathode, and both). Furthermore, this organic electroluminescent device emits light also in the case when a pulse electrical current or an alternate current is applied. The wave form of the applied current may be arbitrary.

<Example of Application of Organic Electroluminescent Device>

Furthermore, the present invention can also be applied to a display device equipped with an organic electroluminescent device or a lighting device equipped with an organic electroluminescent device.

The display device or the lighting device equipped with the organic electroluminescent device can be produced by a known process such as connecting the organic electroluminescent device according to this exemplary embodiment to a known driving apparatus, and can be driven by suitably using a known driving process such as direct current driving, pulse driving and alternate current driving.

Examples of the display device include panel displays such as color flat panel displays, flexible displays such as flexible color organic electroluminescent (EL) displays, and the like (for example, see JP10-335066A, JP2003-321546A, JP2004-281086 A and the like). Furthermore, examples of the display formats of the displays may include matrix and/or segment system(s) and the like. Matrix display and segment display may be present in a same panel.

A matrix refers to pixels for display that are two-dimensionally disposed in a grid form, a mosaic form or the like, and letters and images are displayed by an assembly of pixels. The shape and size of the pixels are determined depending on the intended use. For example, square pixels wherein each side is 300 μm or less are generally used for displaying images and letters on personal computers, monitors and television sets, and pixels wherein each side is in the order of millimeters are used in the cases of large-sized displays such as display panels. In the case of monochrome display, it is sufficient to align pixels of a same color, whereas in the case of color display, the display is conducted by aligning pixels of red, green and blue. In this case, a delta type and a stripe type are typically exemplified. Furthermore, the process for driving this matrix may be a line sequential driving process or an active matrix. The line sequential driving process has an advantage that the structure is easy, but in the case when the operation property is taken into consideration, the active matrix is more excellent in some cases. Therefore, it is necessary to use the process depending on the intended use.

In a segment format (type), a pattern is formed so that information that has been determined in advance is displayed, and fixed regions are allowed to emit light. Examples include display of time and temperature in digital clocks and thermometers, display of the operation state on audio devices, electromagnetic cookers and the like, and display on panels of automobiles, and the like.

Examples of the lighting device include lighting devices such as indoor lighting devices, backlights for liquid crystal display devices, and the like (for example, see JP 2003-257621 A, JP 2003-277741A, JP 2004-119211A and the like). Backlights are mainly used for the purpose of improving the visibility of display devices that do not emit light by themselves, and are used in liquid crystal display devices, clocks, audio apparatuses, automobile panels, display plates and signs, and the like. Especially, as a backlight for use in a liquid crystal display device, especially a personal computer for which thinning is a problem, a backlight using the luminescent device according to this exemplary embodiment is characterized by its thin shape and light weight, considering that a backlight of a conventional system is difficult to be formed into a thin shape since it includes a fluorescent light and a light guiding plate.

EXAMPLES

Synthesis Examples of Benzofluorene Compounds

The synthesis examples of the compounds represented by the formula (1-1), the formula (1-51), the formula (1-22) and the formula (1-20) will be explained below.

Synthesis Example of Compound (1-1)

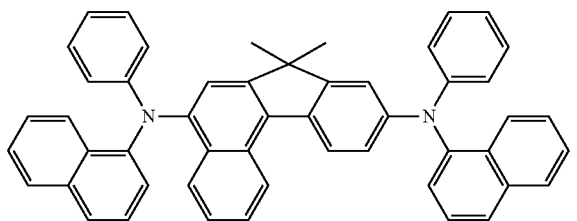

(1-1)

Under an argon atmosphere, 6.1 g of 5,9-diiodo-7,7-dimethyl-7H-benzo[C]fluorene and 2.3 g of aniline were dissolved in 100 ml of dehydrated xylene, 0.12 g of palladium bis(dibenzylidene), 7.2 g of sodium t-butoxide and 0.16 g of (4-(dimethylamino)phenyl)di-t-butylphosphine were added, and heating was conducted at 70° C. for 2 hours. 5.2 g of 1-bromo-naphthalene was further added thereto, and heating was conducted at 100° C. for 3 hours. After cooling to room temperature, 100 ml of water was added, and the organic layer was washed with water by using a separation funnel. The aqueous layer was removed, and the organic layer was collected and concentrated by a rotary evaporator to give a crude product. The crude product was subjected to column purification (solvent: toluene) with alumina to remove the colored components, and further subjected to column purification (solvent: toluene/heptane=1/3 (volume ratio)) with a silica gel. Furthermore, the product was recrystallized with toluene/heptane and purified by sublimation to give 1.9 g of the compound represented by the formula (1-1) (yield: 23%).

The structure of the compound represented by the formula (1-1) was confirmed by an MS spectrum and an NMR measurement.

$^1$H-NMR (CDCl$_3$): δ=8.62 (d, 1H), 8.14 (d, 1H), 8.07 (d, 1H), 7.96 (d, 1H), 7.88 (t, 1H), 7.77 (d, 1H), 7.66 (d, 1H), 7.52-6.73 (m, 25H), 1.27 (s, 6H).

Synthesis Example of Compound (1-51)

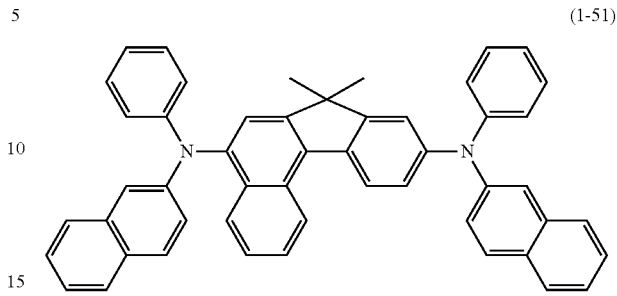

(1-51)

Under an argon atmosphere, 2.5 g of 5,9-diiodo-7,7-dimethyl-7H-benzo[C]fluorene and 1.0 g of aniline were dissolved in 100 ml of dehydrated toluene, 0.028 g of palladium bis(dibenzylidene), 5.8 g of sodium t-butoxide and 0.035 g of (4-(dimethylamino)phenyl)di-t-butylphosphine were added, and heating was conducted at 70° C. for 3 hours. 2.2 g of 2-bromo-naphthalene was further added thereto, and heating was conducted at 100° C. for 3 hours. After cooling to room temperature, 100 ml of water was added, and the organic layer was washed with water by using a separation funnel. The aqueous layer was removed, and the organic layer was collected and concentrated by a rotary evaporator to give a crude product. The crude product was subjected to column purification (solvent: toluene) with alumina to remove the colored components, and further subjected to column purification (solvent: toluene/heptane. This was purified by sublimation to give 1.4 g of a compound represented by the formula (1-51) (yield: 41%).

The structure of the compound represented by the formula (1-51) was confirmed by an MS spectrum and an NMR measurement.

$^1$H-NMR (CDCl$_3$): δ=8.70 (d, 1H), 8.19 (d, 1H), 8.09 (d, 1H), 7.79-6.69 (m, 29H), 1.40 (s, 6H).

Synthesis Example of Compound (1-22)

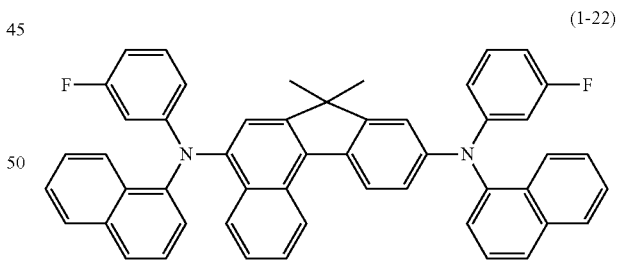

(1-22)

Under an argon atmosphere, 5.0 g of 5,9-diiodo-7,7-dimethyl-7H-benzo[C]fluorene and 2.5 g of 3-fluoroaniline were dissolved in 150 ml of dehydrated xylene, 0.12 g of bis(dibenzylideneacetone) palladium (0), 8.0 g of sodium t-butoxide and 8.0 g of (4-(dimethylamino)phenyl)di-t-butylphosphine were added, and heating was conducted at 70° C. for 2 hours. 5.2 g of 1-bromo-naphthalene was further added thereto, and heating was conducted at 100° C. for 3 hours. The reaction solution was cooled to room temperature, liquid separation was conducted by adding 100 ml of water and stirring, and the organic layer was washed with water. The organic layer was then concentrated in a rotary evaporator to give a crude product. The crude product was subjected to column purification (solvent: toluene/heptane=1/4 (volume ratio)) with alumina to remove the colored components, and further subjected to column purification (solvent: heptane/ethyl acetate=50/1 (volume ratio)) with a silica gel. The solvent was distilled off under a reduced pressure, the residue was dissolved in ethyl acetate again, methanol was added thereto, and the solid obtained by reprecipitation was purified by sublimation to give 1.2 g of a compound represented by the formula (1-22) (yield: 17%).

The structure of the compound represented by the formula (1-22) was confirmed by an MS spectrum and an NMR measurement.

$^1$H-NMR (CDCl$_3$): δ=8.66 (d, 1H), 8.13 (t, 2H), 8.07 (d, 1H), 7.93 (d, 1H), 7.90 (t, 2H), 7.82 (d, 1H), 7.72 (d, 1H), 7.52 (t, 2H), 7.49-7.25 (m, 11H), 7.16-7.01 (m, 3H), 6.81-6.36 (m, 6H), 1.30 (s, 6H).

Synthesis Example of Compound (1-20)

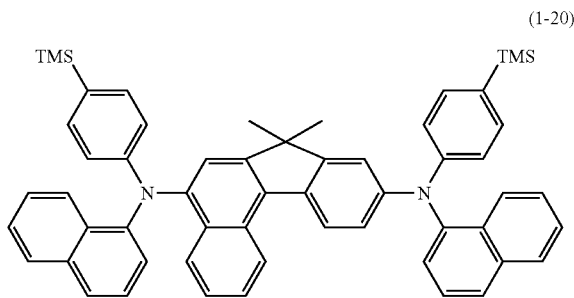 [SMILES: CC1(C)c2cc(N(c3ccc([Si](C)(C)C)cc3)c3cccc4ccccc34)ccc2-c2c1cc(N(c1ccc([Si](C)(C)C)cc1)c1cccc3ccccc13)c1ccccc21]

(1-20)

Under an argon atmosphere, 5.0 g of 5,9-dibromo-7,7-dimethyl-7H-benzo[C]fluorene and 8.0 g of N-(4-(trimethylsilyl)phenyl)naphthalene-1-amine were dissolved in 50 ml of dehydrated xylene, 0.07 g of palladium bis(dibenzylidene), 3.0 g of sodium t-butoxide and 0.07 g of (4-(dimethylamino)phenyl)di-t-butylphosphine were added, and heating was conducted at 90° C. for 2 hours. After cooling to room temperature, liquid separation was conducted by adding water and ethylacetate. The solvent in the organic layer was distilled off under a reduced pressure, and the organic layer was purified by silica gel column chromatography (developer: toluene/heptane/triethylamine=5/94/1 (volume ratio)) and further purified by active carbon column chromatography (developer: toluene/heptane/triethylamine=20/80/1 (volume ratio)). The solvent was distilled off under a reduced pressure, and recrystallization from ethanol was conducted to give 7.1 g of a compound represented by the formula (1-20).

The structure of the compound represented by the formula (1-20) was confirmed by an NMR measurement.

$^1$H-NMR (CDCl$_3$): δ=8.64 (d, 1H), 8.17 (d, 1H), 8.08 (m, 2H), 7.96 (d, 1H), 7.89 (t, 2H), 7.80 (d, 1H), 7.69 (d, 1H), 7.42-7.56 (m, 4H), 7.20-7.41 (m, 12H), 7.03 (m, 3H), 6.66 (m, 2H), 1.29 (s, 6H), 0.24 (s, 9H), 0.20 (s, 9H).

Properties in Case of Use in Electroluminescent Device (1)

Firstly, the electroluminescent devices of Examples 1 and 2 and Comparative Example 1 were prepared, and the voltage (V), the current density (mA/cm$^2$), the luminescence efficiency (lm/W), the measurement of the current efficiency (cd/A), the EL luminescence wavelength (nm) and the outer quantum efficiency (%), which are respectively the characteristics at the time of luminescence at 1000 cd/m$^2$, were respectively measured. Secondly, the time in which a luminance of 90% (1800 cd/m$^2$) or more is retained when driven under a constant current at a current density at which a luminance of 2000 cd/m$^2$ is obtained was measured.

Meanwhile, the quantum efficiencies of a luminescent device include an inner quantum efficiency and an outer quantum efficiency, and the inner quantum efficiency shows a ratio of pure conversion of outer energy that is injected as electrons (or holes) into a luminescent layer of a luminescent device to photons. On the other hand, the outer quantum efficiency is calculated based on the amount of the photons released to the outside of the luminescent device, and a part of the photons generated in the luminescent layer is absorbed or continuously reflected inside of the luminescent device and thus are not released to the outside of the luminescent device. Therefore, the outer quantum efficiency is lower than the inner quantum efficiency.

The process for measuring the outer quantum efficiency is as follows. Using a voltage/electrical current generator R6144 manufactured by Advantest, a voltage at which the luminance of the element became 1000 cd/m$^2$ was applied to the element to allow luminescence. Using a spectroradiometer SR-3AR manufactured by TOPCON, the spectroradiance in the visible light region was measured from the direction vertical to the luminescent plane. Assuming that the luminescent plane is a complete diffusion plane, a numerical value obtained by dividing the measured value of the spectroradiance of each wavelength component by wavelength energy and multiplying the obtained value by π is a photon number in each wavelength. Subsequently, the photon numbers were integrated in all of the observed wavelength regions and set as a number of the whole photons released from the element. A numerical value obtained by dividing the value of the applied current by an elementary charge is set as the number of the carrier injected into the element, and a numerical value obtained by dividing the number of the whole photons released from the element by the number of the carrier injected into the element is the outer quantum efficiency.

The material constitutions of the respective layers in the prepared electroluminescent devices of Examples 1 and 2 and Comparative Example 1 are shown in the following Table 1.

TABLE 1

| | Hole Injection Layer (40 nm) | Hole Transport Layer (30 nm) | Luminescent Layer (35 nm) | | Electron Transport Layer (15 nm) | Cathode (1 nm/100 nm) |
|---|---|---|---|---|---|---|
| | | | Host (95%) | Dopant (5%) | | |
| Example 1 | HI | NPD | Compound (A) | Compound (1-1) | Compound (C) | Liq/Mg + Ag |
| Example 2 | HI | NPD | Compound (A) | Compound (1-51) | Compound (C) | Liq/Mg + Ag |
| Comparative Example 1 | HI | NPD | Compound (A) | Compound (B) | Compound (C) | Liq/Mg + Ag |

In Table 2, "HI" is $N^4,N^{4'}$-diphenyl-$N^4,N^{4'}$-bis(9-phenyl-9H-carbazol-3-yl)-[1,1'-biphenyl]-4,4'-diamine, "NPD" is $N^4,N^{4'}$-di(naphthalen-1-yl)-$N^4,N^{4'}$-diphenyl-[1,1'-biphenyl]-4,4'-diamine, compound (A) is 9-phenyl-10-(4-phenylnaphthalen-1-yl)anthracene, compound (B) is $N^5, N^5, N^9, N^9$,7,7-hexaphenyl-7H-benzo[c]fluorene-5,9-diamine, compound (C) is 5,5'-(2-phenylanthracene-9,10-diyl)di-2,2'-bipyridine, and "Liq" is 8-quinolinollithium. The chemical structures are shown below.

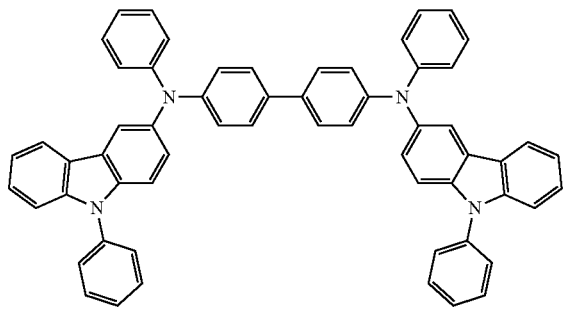

HI

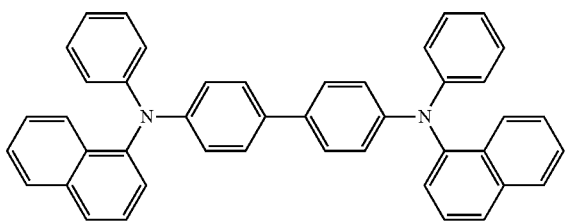

NPD

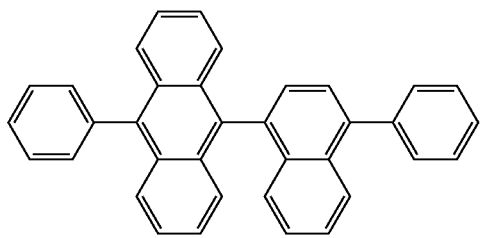

Compound (A)

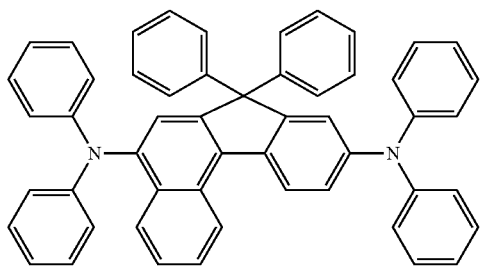

Compound (B)

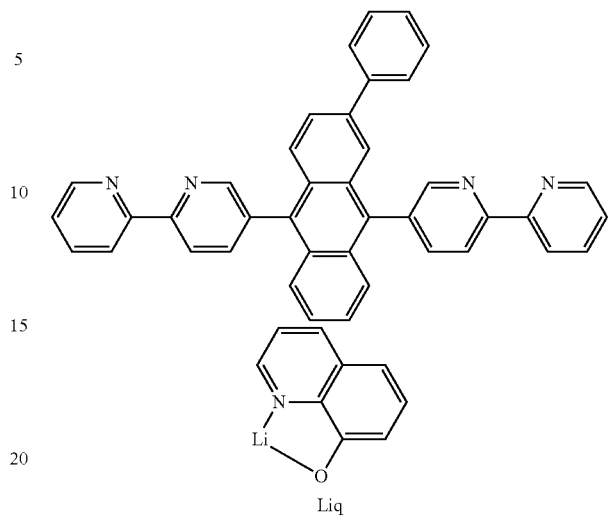

Compound (C)

Liq

Example 1

Element Using Compound (1-1) in Dopant of Luminescent Layer

A glass substrate of 26 mm×28 mm×0.7 mm on which ITO had been deposited at a thickness of 150 nm was used as a transparent support substrate. This transparent support substrate was fixed on a substrate holder of a commercially available deposition apparatus, and a molybdenum deposition boat containing HI, a molybdenum deposition boat containing NPD, a molybdenum deposition boat containing the compound (A), a molybdenum deposition boat containing the compound (1-1), a molybdenum deposition boat containing the compound (C), a molybdenum deposition boat containing Liq, a molybdenum deposition boat containing magnesium and a tungsten deposition boat containing silver were attached thereto.

The following respective layers were successively formed on the ITO film of the transparent support substrate. The pressure in a vacuum bath was reduced to $5\times10^{-4}$ Pa, the deposition boat containing HI was first heated to conduct deposition so as to give a film thickness of 40 nm to thereby form a hole injection layer, and the deposition boat containing NPD was then heated to conduct deposition so as to give a film thickness of 30 nm to thereby form a hole transport layer. Subsequently, the deposition boat containing the compound (A) and the deposition boat containing the compound (1-1) were simultaneously heated to conduct deposition so as to give a film thickness of 35 nm to thereby form a luminescent layer. The deposition velocity was controlled so that the weight ratio of compound (A) to compound (1-1) became approximately 95 to 5. Subsequently, the deposition boat containing the compound (C) was heated to conduct deposition so as to give a film thickness of 15 nm to thereby form an electron transport layer. The above-mentioned deposition velocities were 0.01 to 1 nm/sec.

Thereafter, the deposition boat containing Liq was heated to conduct deposition so as to give a film thickness of 1 nm at a deposition velocity of 0.01 to 0.1 nm/sec. Subsequently, the boat containing magnesium and the boat containing silver were simultaneously heated to conduct deposition so as to give a film thickness of 100 nm to thereby form a cathode. At this time, the deposition velocity was controlled so that the atom number ratio of the magnesium to silver became 10 to 1, and the cathode was formed so that the deposition velocity became 0.1 nm to 10 nm to thereby give an organic electroluminescent device.

When the properties at the time of luminescence at 1000 cd/m$^2$ were measured by using the ITO electrode as an anode and the electrode formed of a co-deposited product of Liq/magnesium and silver as a cathode, the voltage was 4.00 V, the current density was 20.29 mA/cm$^2$, the luminescence efficiency was 3.88 (lm/W), the electrical current efficiency was 4.93 cd/A, the outer quantum efficiency was 4.750 (luminescence wavelength: 457 nm, chromaticity: (x=0.144, y=0.143)), and the time in which a luminance of 90% (1800 cd/m$^2$) or more is retained when driven under a constant current at a current density at which a luminance of 2000 cd/m$^2$ is obtained was 180 hours.

Comparative Example 1

Element Using Compound (B) in Dopant Material of Luminescent Layer

An organic EL element was obtained by a process according to Example 1, except that compound (1-1) that was used in the dopant of the luminescent layer in Example 1 was changed to the compound (B). When the properties at the time of luminescence at 1000 cd/m$^2$ were measured by using the ITO electrode as an anode and the electrode formed of a co-deposited product of Liq/magnesium and silver as a cathode, the voltage was 3.96 V, the current density was 17.20 mA/cm$^2$, the luminescence efficiency was 4.62 (lm/W), the current efficiency was 5.82 cd/A, the outer quantum efficiency was 5.58% (luminescence wavelength: 457 nm, chromaticity: (x=0.142, y=0.141)), and the time in which a luminance of 90% (1800 cd/m$^2$) or more is retained when driven under a constant current at a current density at which a luminance of 2000 cd/m$^2$ is obtained was 19 hours.

The above-mentioned results are summarized in Table 2.

TABLE 2

| | Properties @ luminescence of 1000 cd/m$^2$ | | | | | | |
|---|---|---|---|---|---|---|---|
| | Voltage (V) | Current Density (mA/cm$^2$) | Luminescence Efficiency (lm/W) | Current Efficiency (cd/A) | EL (nm) | Outer Quantum Efficiency % | Time in which a luminance of 90% or more of initial is retained |
| Example 1 | 4.00 | 20.29 | 3.88 | 4.93 | 457 | 4.75 | 180 |
| Example 2 | 3.96 | 17.47 | 4.54 | 5.73 | 460 | 5.10 | 26 |
| Comparative Example 1 | 3.96 | 17.20 | 4.62 | 5.82 | 457 | 5.58 | 19 |

Example 2

Element Using Compound (1-51) as Dopant Material for Luminescent Layer

An organic EL element was obtained by a process according to Example 1, except that compound (1-1) that was used in the dopant of the luminescent layer in Example 1 was changed to the compound (1-51). When the properties at the time of luminescence at 1000 cd/m$^2$ were measured by using the ITO electrode as an anode and the electrode formed of a co-deposited product of Liq/magnesium and silver as a cathode, the voltage was 3.96 V, the current density was 17.47 mA/cm$^2$, the luminescence efficiency was 4.54 (lm/W), the current efficiency was 5.73 cd/A, the outer quantum efficiency was 5.10% (luminescence wavelength: 460 nm, chromaticity: (x=0.141, y=0.163)), and the time in which a luminance of 90% (1800 cd/m$^2$) or more is retained when driven under a constant current at a current density at which a luminance of 2000 cd/m$^2$ is obtained was 26 hours.

Properties when Used in Electroluminescent Device (2)

Firstly, the electroluminescent devices of Example 3 and Comparative Example 2 were prepared, and the voltage (V), the current density (mA/cm$^2$), the luminescence efficiency (lm/W), the measurement of the current efficiency (cd/A), the EL luminescence wavelength (nm) and the outer quantum efficiency (%), which are respectively the characteristics at the time of luminescence at 700 cd/m$^2$, were measured. Secondly, the time in which a luminance of 85% (1020 cd/m$^2$) or more is retained when driven under a constant current at a current density at which a luminance of 1200 cd/m$^2$ is obtained was measured.

The material constitutions of the respective layers in the prepared electroluminescent devices of Example 3 and Comparative Example 2 are shown in the following Table 3.

TABLE 3

| | Hole Injection Layer (40 nm) | Hole Transport Layer (30 nm) | Luminescent Layer (20 nm) | | Electron Transport Layer (30 nm) | Cathode (1 nm/100 nm) |
|---|---|---|---|---|---|---|
| | | | Host (95%) | Dorpant (5%) | | |
| Example 3 | HI | NPD | Compound (D) | Compound (1-22) | Compound (E) + Liq | Liq/Al |
| Comparative Example 2 | HI | NPD | Compound (D) | Compound (F) | Compound (E) + Liq | Liq/Al |

In Table 3, the compound (D) is 9-(4-(naphthalen-1-yl)phenyl)-10-phenylanthracene, the compound (E) is 2-(4-(9,10-di(naphthalen-2-yl)anthracen-2-yl)phenyl)-1-phenyl-1H-benzo[d]imidazole, and the compound (F) is 7,7- dimethyl-N⁵,N⁹-diphenyl-N⁵,N⁹-di(fluorobenzen-3-yl)-7H-benzo[c]fluorene-5,9-diamine. The chemical structures are shown below.

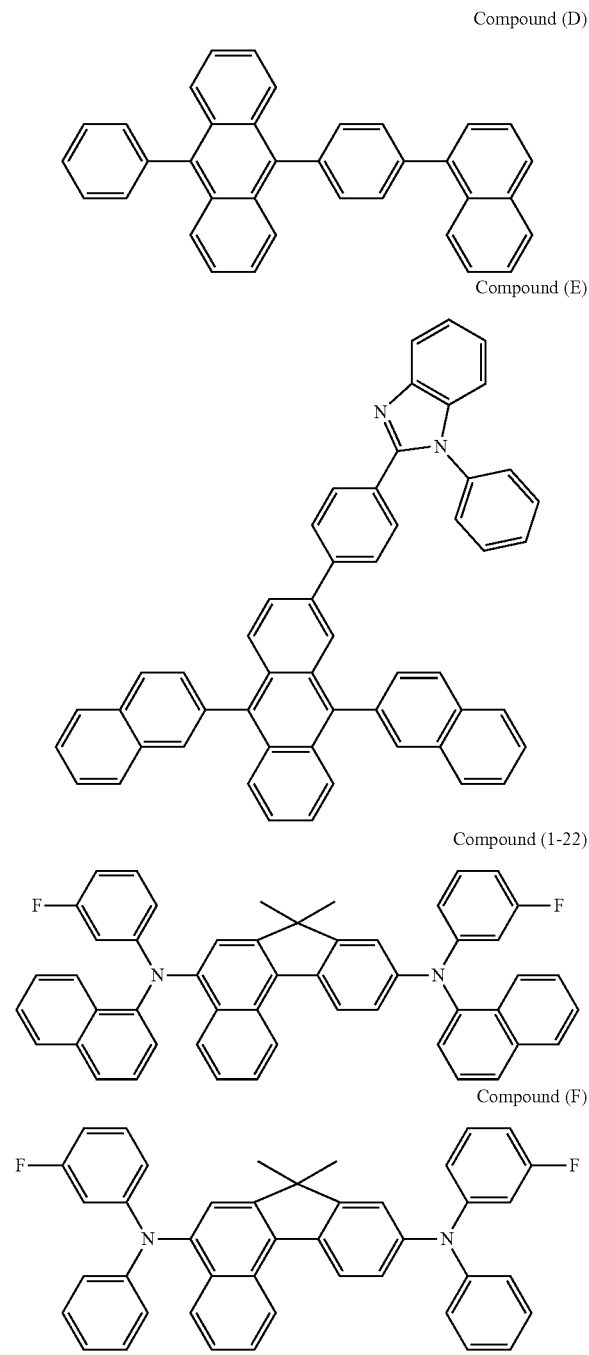

Example 3

Element Using Compound (1-22) in Dopant of Luminescent Layer

A glass substrate of 26 mm×28 mm×0.7 mm on which ITO had been deposited at a thickness of 150 nm was used as a transparent support substrate. This transparent support substrate was fixed on a substrate holder of a commercially available deposition apparatus, and a molybdenum deposition boat containing HI, a molybdenum deposition boat containing NPD, a molybdenum deposition boat containing the compound (D), a molybdenum deposition boat containing the compound (1-22), a molybdenum deposition boat containing the compound (E), a molybdenum deposition boat containing Liq and a molybdenum deposition boat containing aluminum were attached thereto.

The following respective layers were successively formed on the ITO film of the transparent support substrate. The pressure in a vacuum bath was reduced to $5 \times 10^{-4}$ Pa, the deposition boat containing HI was first heated to conduct deposition so as to give a film thickness of 40 nm to thereby form a hole injection layer, and the deposition boat containing NPD was then heated to conduct deposition so as to give a film thickness of 30 nm to thereby form a hole transport layer. Subsequently, the deposition boat containing the compound (D) and the deposition boat containing the compound (1-22) were simultaneously heated to conduct deposition so as to give a film thickness of 20 nm to thereby form a luminescent layer. The deposition velocity was controlled so that the weight ratio of the compound (D) to the compound (1-22) became approximately 95 to 5. Subsequently, the deposition boat containing the compound (E) and the deposition boat containing Liq were simultaneously heated to conduct deposition so as to give a film thickness of 30 nm to thereby form an electron transport layer. The deposition velocities of the respective layers were 0.01 to 1 nm/sec.

Thereafter, the deposition boat containing Liq was heated to conduct deposition so as to give a film thickness of 1 nm at a deposition velocity of 0.01 to 0.1 nm/sec. Subsequently, the deposition boat containing aluminum was heated to conduct deposition so as to give a film thickness of 100 nm to form a cathode, to thereby give an organic EL element.

When the properties at the time of luminescence at 700 cd/m² were measured by using the ITO electrode as an anode and the Liq/aluminum electrode as a cathode, the voltage was 4.27 V, the density was 30.96 mA/cm², the luminescence efficiency was 1.66 (lm/W), the current efficiency was 2.26 cd/A, and the outer quantum efficiency was 3.09% (luminescence wavelength: 447 nm, chromaticity: (x=0.151, y=0.096)), and the time in which a luminance of 85% (1020 cd/m²) or more is retained when driven under a constant current at a current density at which a luminance of 1200 cd/m² is obtained was 201 hours.

Comparative Example 2

Element Using Compound (F) in Dopant Material of Luminescent Layer

An organic EL element was obtained by a process according to Example 3, except that the compound (1-22) that was used in the dopant of the luminescent layer in Example 3 was changed to the compound (F). When the properties at the time of luminescence at 700 cd/m² were measured by using the ITO electrode as an anode and the Liq/aluminum electrode as a cathode, the voltage was 3.98 V, the current density was 36.21 mA/cm², the luminescence efficiency was 1.52 (lm/W), the current efficiency was 1.93 cd/A, the outer quantum efficiency was 2.34% (luminescence wavelength: 449 nm, chromaticity: (x=0.152, y 0.107)), and the time in which a luminance of 85% (1020 cd/m²) or more is retained when driven under a constant current at a current density at which a luminance of 1200 cd/m² is obtained was 137 hours.

The above-mentioned results are summarized in Table 4.

TABLE 4

| | Properties @ luminescence of 700 cd/m² | | | | | | |
|---|---|---|---|---|---|---|---|
| | Voltage (V) | Current Density (mA/cm²) | Luminescence Efficiency (lm/W) | Current Efficiency (cd/A) | EL (nm) | Outer Quantum Efficiency % | Time in which a luminance of 85% or more of initial is retained |
| Example 3 | 4.27 | 30.96 | 1.66 | 2.26 | 447 | 3.09 | 201 |
| Comparative Example 2 | 3.98 | 36.21 | 1.52 | 1.93 | 449 | 2.34 | 137 |

Properties in Case of Use in Electroluminescent Device (3)

Firstly, the electroluminescent devices of Example 4 and Comparative Example 3 were respectively prepared, and the luminescences were confirmed, and the times (hr) in which the luminance retains 90% or more of the initial value when driven at a constant current of 30 mA/cm² were measured.

The material constitutions of the respective layers in the prepared electroluminescent devices of Example 4 and Comparative Example 3 are shown in the following Table 5. The cathode was constituted by a co-deposited product of 8-quinolinollithium (Liq)/magnesium and silver in all of the devices.

TABLE 5

| | Hole Injection Layer (40 nm) | Hole Transport Layer (30 nm) | Luminescent Layer (20 nm) | | Electron Transport Layer (30 nm) | Cathode (1 nm/100 nm) |
|---|---|---|---|---|---|---|
| | | | Host (95%) | Dopant (5%) | | |
| Example 4 | HI | HT | Compound (A) | Compound (1-20) | Compound (E) + Liq | Mg/Ag |
| Comparative Example 3 | HI | HT | Compound (A) | Compound (G) | Compound (E) + Liq | Mg/Ag |

In Table 5, HT is N-([1,1'-biphenyl]-4-yl)-9,9-dimethyl-N-(4-(9-phenyl-9H-carbazol-3-yl)phenyl)-9H-fluorene-2-amine, and the compound (G) is 7,7-dimethyl-$N^5,N^9$-diphenyl-$N^5,N^9$-bis(4-(trimethylsilyl)phenyl)-7H-benzo[c]fluorene-5,9-diamine. The chemical structures are shown below.

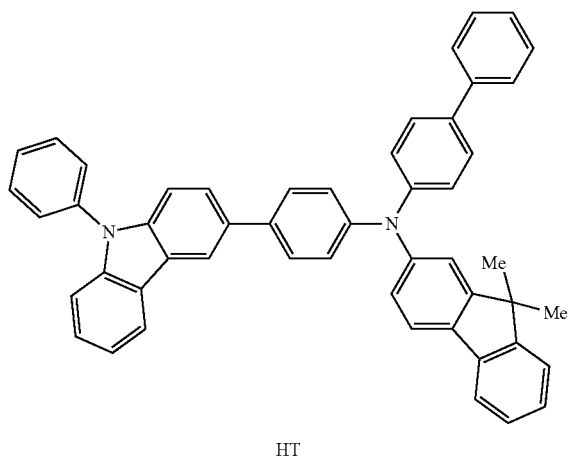

HT

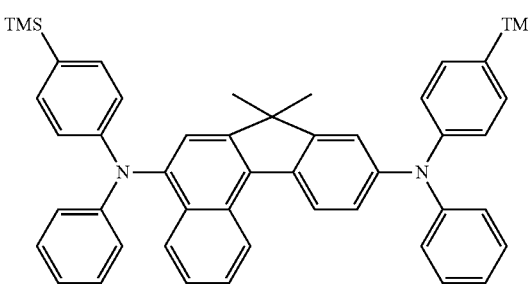

Compound (G)

Example 4

Element Using Compound (1-20) in Dopant of Luminescent Layer

A glass substrate of 26 mm×28 mm×0.7 mm with ITO that had been formed into a film having a thickness of 180 nm by sputtering and then polished up to 150 nm (manufactured by Opto Science, Inc.) was used as a transparent support substrate. This transparent support substrate was fixed on a substrate holder of a commercially available deposition apparatus (manufactured by Showa Shinku Co., Ltd.), and a molybdenum deposition boat containing HI, a molybdenum deposition boat containing HT, a molybdenum deposition boat containing the compound (A), a molybdenum deposition boat containing the compound (1-20), a molybdenum deposition boat containing the compound (E), a molybdenum deposition boat containing Liq, a molybdenum deposition boat containing magnesium and a tungsten deposition boat containing silver were attached.

The following respective layers were successively formed on the ITO film of the transparent support substrate. The pressure in a vacuum bath was reduced to 5×10⁻⁴ Pa, the deposition boat containing HI was first heated to conduct deposition so as to give a film thickness of 40 nm to thereby form a hole injection layer, and the deposition boat containing HT was then heated to conduct deposition so as to give a film thickness of 30 nm to thereby form a hole transport layer. Subsequently, the deposition boat containing the compound (A) and the deposition boat containing the compound (1-20) were simultaneously heated to conduct deposition so as to give a film thickness of 20 nm to thereby form a luminescent layer. The deposition velocity was controlled so that the weight ratio of the compound (A) to the compound (1-20) became approximately 95 to 5. Subsequently, the deposition boat containing the compound (E) and the deposition boat containing Liq were simultaneously heated to conduct deposition so as to give a film thickness of 30 nm to thereby form an electron transport layer. The deposition velocity was controlled so that the weight ratio of the compound (E) and Liq became approximately 1 to 1. The deposition velocities of the respective layers were 0.01 to 1 nm/sec.

Thereafter, the deposition boat containing Liq was heated to conduct deposition so as to give a film thickness of 1 nm at a deposition velocity of 0.01 to 0.1 nm/sec. Subsequently, the boat containing magnesium and the boat containing silver were simultaneously heated so as to give a film thickness of 100 nm to form a cathode. At this time, the deposition velocity was controlled so that the atom number ratio of magnesium to silver became 10 to 1, and the cathode was formed so that the deposition velocity became 0.1 to 10 nm/sec to give an organic electroluminescent device.

When a direct current voltage was applied by using the ITO electrode as an anode and the electrode formed of the co-deposited product of Lig/magnesium and silver as the cathode, blue luminescence at a wavelength of about 453 nm was obtained. Furthermore, when a driving test at a constant current of 30 mA/cm² was conducted, the time in which a luminance of 900 or more of the initial value is retained was 105 hours.

Comparative Example 3

Element Using Compound (G) in Dopant of Luminescent Layer

An organic EL element was obtained by a process according to Example 4, except that the compound (1-20) was changed to the compound (G). When a direct current was applied by using the ITO electrode as an anode and the magnesium/silver electrode as a cathode, blue luminescence at a wavelength of about 455 nm was obtained. Furthermore, when a driving test at a constant current of 30 mA/cm² was conducted, the time in which luminance of 90% or more of the initial value was retained was 78 hours.

As is understood from the evaluation of the performances of the electroluminescent devices according to the above-mentioned Examples and Comparative Examples, it is understood that the electroluminescent devices of Examples have more excellent device lifetimes than that of the electroluminescent devices of Comparative Examples while the electroluminescent devices maintain their low driving voltages and excellent color purities, and are more excellent in driving voltage and color purity than the luminescent devices described in the conventional patent documents.

INDUSTRIAL APPLICABILITY

According to the preferable embodiments of the present invention, an organic electroluminescent device having excellent device lifetime while maintaining a low driving voltage and an excellent color purity, a display device equipped with the organic electroluminescent device and a lighting device equipped with the organic electroluminescent device, and the like can be provided.

REFERENCE SIGNS LIST

100 Organic electroluminescent device
101 Substrate
102 Anode
103 Hole injection layer
104 Hole transport layer
105 Luminescent layer
106 Electron transport layer
107 Electron injection layer
108 Cathode

The invention claimed is:

1. A benzofluorene compound represented by the following formula (1):

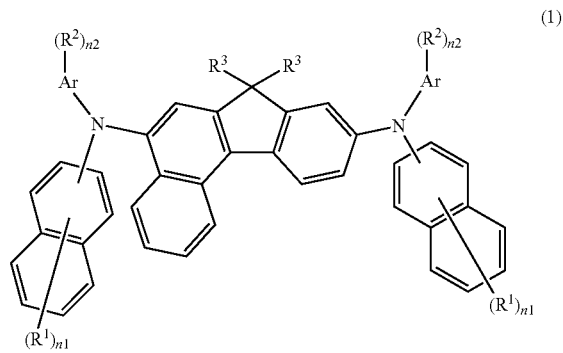

wherein
Ar is each independently phenyl, naphthyl or a heteroaryl,
$R^1$ is each independently, an aryl, a cycloalkyl, fluorine, cyano, an alkyl substituted by fluorine, an alkoxy optionally substituted by fluorine, a substituted silyl or a substituted germyl,
$R^2$ is each independently, an aryl, fluorine, cyano, an alkyl substituted by fluorine, an alkoxy optionally substituted by fluorine, a substituted silyl or a substituted germyl,
n1 and n2 are each independently an integer of 0 to 5, and in the case when one naphthyl group is substituted with two or more adjacent $R^1$s or in the case when one Ar group is substituted with two or more adjacent $R^2$s, these may bind to form an aliphatic ring,
$R^3$ is each independently an alkyl or an aryl, wherein two $R^a$s may bind to each other to form a ring, and
at least one hydrogen in the compound represented by the formula (1) may be substituted with deuterium.

2. The benzofluorene compound according to claim 1, wherein
Ar is each independently phenyl or pyridyl,
$R^1$ is each independently an aryl with a carbon number of 6 to 12, a cycloalkyl with a carbon number of 3 to 6, fluorine, cyano, an alkyl with a carbon number of 1 to 6 substituted by fluorine, an alkoxy with a carbon number of 1 to 4 optionally substituted by fluorine, an alkyl-substituted silyl or an alkyl-substituted germyl,
$R^2$ is each independently an aryl with a carbon number of 6 to 12, fluorine, cyano, an alkyl with a carbon number of 1 to 6 substituted by fluorine, an alkoxy with a carbon number of 1 to 4 optionally substituted by fluorine, an alkyl-substituted silyl or an alkyl-substituted germyl, n1 and n2 are each independently an integer of 0 to 3, and in the case when one naphthyl group is substituted with two or more adjacent $R^1$s or in the case when one Ar group is substituted with two or more adjacent $R^2$s, they may bind to form an aliphatic ring with a carbon number of 3 to 6, $R^3$ is each independently an alkyl with a carbon number of 1 to 6 or an aryl with a carbon number of 6 to 12, wherein two $R^a$s may bind to each other to form a ring, and at least one hydrogen in the Ar and naphthyl groups in the compound represented by the formula (1) may be substituted with deuterium.

3. The benzofluorene compound according to claim 1, wherein

Ar is each independently phenyl or pyridyl, $R^1$ is each independently phenyl, cyclopropyl, cyclobutyl, cyclopentyl, cyclohexyl, methylcyclopentyl, fluorine, cyano, methyl fluoride, ethyl fluoride, methoxy, ethoxy, propoxy, isopropoxy, n-butoxy, isobutoxy, s-butoxy, t-butoxy, methoxy fluoride, ethoxy fluoride, trimethylsilyl, triethylsilyl, t-butyldimethylsilyl, trimethylgermyl, triethylgermyl or t-butyldimethylgermyl, $R^2$ is each independently phenyl, fluorine, cyano, methyl fluoride, ethyl fluoride, methoxy, ethoxy, propoxy, isopropoxy, n-butoxy, isobutoxy, s-butoxy, t-butoxy, methoxy fluoride, ethoxy fluoride, trimethylsilyl, triethylsilyl, t-butyldimethylsilyl, trimethylgermyl, triethylgermyl or t-butyldimethylgermyl, n1 and n2 are each independently an integer of 0 to 2, and in the case when one naphthyl group is substituted with two or more adjacent $R^1$s or in the case when one Ar group is substituted with two or more adjacent $R^2$s, these may bind to form an aliphatic ring with a carbon number of 5 to 6, $R^3$ is each independently methyl, ethyl, n-propyl, isopropyl, n-butyl, s-butyl, t-butyl or phenyl, and in the case when n1 and n2 are 0, at least one hydrogen in the Ar and naphthyl groups in the compound represented by the formula (1) may be substituted with deuterium.

4. The benzofluorene compound according to claim 1, wherein

Ar is each independently phenyl or pyridyl, $R^1$ is each independently phenyl, cyclopentyl, cyclohexyl, methylcyclopentyl, fluorine, cyano, methyl fluoride, methoxy, ethoxy, methoxy fluoride, trimethylsilyl, triethylsilyl, trimethylgermyl or triethylgermyl, $R^2$ is each independently phenyl, fluorine, cyano, methyl fluoride, methoxy, ethoxy, methoxy fluoride, trimethylsilyl, triethylsilyl, trimethylgermyl or triethylgermyl, n1 and n2 are each independently an integer of 0 to 2, and in the case when one naphthyl group is substituted with two or more adjacent $R^1$s or in the case when one Ar group is substituted with two or more adjacent $R^2$s, these may bind to form a cyclohexane ring, and $R^3$s are each independently methyl, ethyl or phenyl.

5. The benzofluorene compound according to claim 1, which is represented by the following formula (1-1):

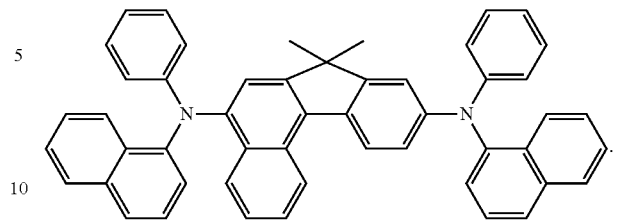

(1-1)

6. The benzofluorene compound according to claim 1, which is represented by the following formula (1-51):

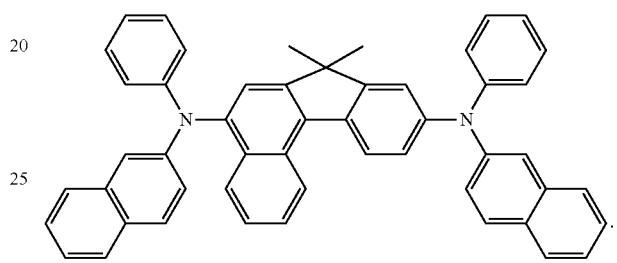

(1-51)

7. The benzofluorene compound according to claim 1, which is represented by the following formula (1-22):

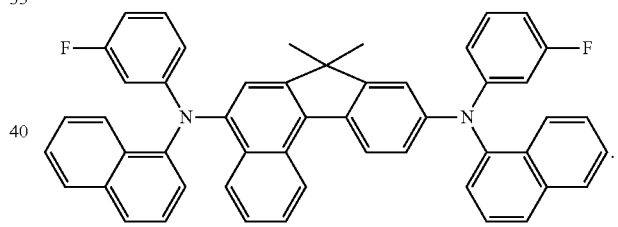

(1-22)

8. The benzofluorene compound according to claim 1, which is represented by the following formula (1-20):

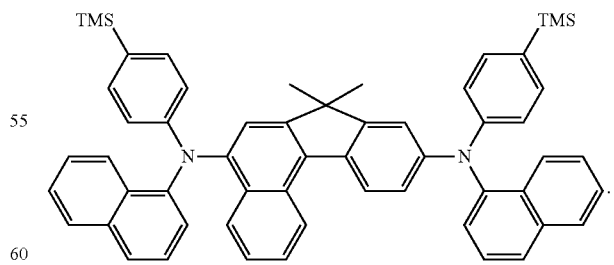

(1-20)

9. A material for a luminescent layer of a luminescent device, which comprises the benzofluorene compound according to claim 1.

10. An organic electroluminescent device comprising a pair of electrodes of an anode and a cathode, and a luminescent layer containing the material for a luminescent layer according to claim 9, which is disposed between the pair of electrodes.

11. The organic electroluminescent device according to claim 10, which further comprises an electron transport layer and/or an electron injection layer that is/are disposed between the cathode and the luminescent layer, wherein at least one of the electron transport layer and electron injection layer comprises at least one compound selected from the group consisting of a quinolinol-based metal complex, a pyridine derivative, a phenanthroline derivative, a borane derivative, and a benzimidazole derivative.

12. The organic electroluminescent device according to claim 11, wherein the electron transport layer and/or electron injection layer further comprise(s) at least one compound selected from the group consisting of an alkali metal, an alkaline earth metal, a rare earth metal, an oxide of an alkali metal, a halide of an alkali metal, an oxide of an alkaline earth metal, a halide of an alkaline earth metal, an oxide of a rare earth metal, a halide of a rare earth metal, an organic complex of an alkali metal, an organic complex of an alkaline earth metal and an organic complex of a rare earth metal.

13. A display device comprising the organic electroluminescent device according to claim 10.

14. A lighting device comprising the organic electroluminescent device according to claim 10.

* * * * *